(12) United States Patent
Wallach et al.

(10) Patent No.: US 6,579,697 B1
(45) Date of Patent: *Jun. 17, 2003

(54) MODULATOR OF TNF/NGF SUPERFAMILY RECEPTORS AND SOLUBLE OLIGOMERIC TNF/NGF SUPERFAMILY RECEPTORS

(75) Inventors: David Wallach, Rehovot (IL); Mark Boldin, Moscow (RU); Igor Mett, Rehovot (IL); Eugene Varfolomeev, Rehovot (IL)

(73) Assignee: Yeda Research and Development Co. Ltd., Rehovot (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/747,562

(22) Filed: Nov. 12, 1996

Related U.S. Application Data

(63) Continuation-in-part of application No. PCT/US95/05854, filed on May 11, 1995.

(51) Int. Cl.$^7$ .............................................. C12N 15/00
(52) U.S. Cl. ....................... 435/69.1; 435/6; 435/320.1; 435/325; 435/252.3
(58) Field of Search ............................ 435/69.1, 320.1, 435/325, 252.3, 254.11; 536/23.5

(56) References Cited

U.S. PATENT DOCUMENTS

| | | | | |
|---|---|---|---|---|
| 5,563,039 A | * | 10/1996 | Goeddel et al. | 435/7.1 |
| 5,610,279 A | * | 3/1997 | Brockhaus et al. | 530/387.3 |
| 5,632,994 A | * | 5/1997 | Reed et al. | 424/198.1 |
| 5,674,734 A | * | 10/1997 | Leder et al. | 435/252.3 |

FOREIGN PATENT DOCUMENTS

| | | | | |
|---|---|---|---|---|
| EP | 393438 | * | 10/1990 | C12N/15/12 |
| EP | 0 417 563 A2 | | 3/1991 | |
| EP | 0 418 014 A1 | | 3/1991 | |
| EP | 0 510 691 A1 | | 10/1992 | |

OTHER PUBLICATIONS

Song, et al. J. Biol. Chem. vol. 269(36): pp. 22492–22495, Sep. 1994.*
Rothe, et al. Cell vol. 78(4): pp. 681–692, Aug. 1994.*
Tartaglia et al, "Tumor Necrosis Factor Receptor Signaling", *The Journal of Biological Chemistry*, vol. 267, No. 7, Issue of Mar. 5, pp. 4304–4307 (1992).
Banner et al, "Crystal structure of the soluble human 55 kd TNF receptor–human TNF beta complex: implications for TNF receptor activation", *Cell* 73(3):432–445 (1993).
Boldin et al, "A Novel Protein That Interacts with the Death Domain of Fas/APO1 Contains a Sequence Motif Related to the Death Domain", *J Biol Chem* 270(14):7794–7798 (1995).
Chinnaiyan et al, "FADD, a Novel Death Domain–Containing Protein, Interacts with the Death Domain of Fas and Initiates Apoptosis", *Cell* 81:505–512 (1995).
Clement et al, "Fas and Tumor Necrosis Factor Receptor–mediated Cell Death: Similarities and Distinctions", *J Exp Med* 180:557–567 (1994).
Darnay et al, "Physical and Functional Association of a Serine–Threonine Protein Kinase to the Cytoplasmic Domain of the p80 Form of the Human Tumor Necrosis Factor Receptor in Human Histiocytic Lymphoma U–937 Cells", *J Biol Chem* 269(31):19687–19690 (1994).
Evans et al, "Protective Effect of 55–but not 75–kD Soluble Tumor Necrosis Factor Receptor–Immunoglobulin G Fusion Proteins in an Animal Model of Gram–negative Sepsis" *J Exp Med* 180:2173–2179 (1994).
Hsu et al, "Differential Expression and Ligand Binding Properties of Tumor Necrosis Factor Receptor Chimeric Mutants", *J Biol Chem* 268(22):16430–16436 (1993).
Hsu et al, "The TNF Receptor 1–Associated Protein TRADD Signals Cell Death and NF–kB Activation", *Cell* 81:495–504 (1995).
Itoh et al, "A novel protein domain required for apoptosis. Mutational analysis of human Fas antigen", *J Biol Chem* 268(15):10932–10937 (1993).
Lewis et al, "Cloning and expression of cDNAs for two distinct murine tumor necrosis factor receptors demonstrate one receptor is specifies specific", *Proc Natl Acad Sci USA* 88:2830–2834 (1991).
Morimoto et al, "Overcoming Tumor Necrosis Factor and Drug Resistance of Human Tumor Cell Lines by Combination Treatment with Anti–Fas Antibody and Drugs or Toxins", *Cancer Res* 53:2591–2596 (1993).
Song et al, "Identification of a Protein with Homology to hsp90 That Binds the Type 1 Tumor Necrosis Factor Receptor", *J Biol Chem* 270(8)3574–3581 (1995(.
Stanger et al, "RIP: A Novel Protein Containing a Death Domain That Interacts with Fas/APO–1 (CD95) in Yeast and Causes Cell Death", *Cell* 81:513–523 (1995).
Suda et al, "Molecular Cloning and Expression of the Fas Ligand, a Novel Member of the tumor Necrosis Factor Family", *Cell* 75:1169–1178 (1993).
Tartaglia et al, "Tumor Necrosis Factor Receptor Signaling: A Dominant Negative Mutation Suppresses the Activation of the 55–KDA Tumor Necrosis Factor Receptor", *J Biol Chem* 267(7):4304–4307 (1992).
Tartaglia et al, "A novel domain with the 55 kd TNF receptor signals cell death", *Cell* 74(5):845–853 (1993).
Van Aelst et al, "Complex formation between RAS and RAF and other protein kinases", *Proc Natl Acad Sci USA* 90:6213–6217 (1993).

* cited by examiner

Primary Examiner—Lorraine Spector
Assistant Examiner—Dong Jiang
(74) Attorney, Agent, or Firm—Browdy and Neimark, P.L.L.C.

(57) ABSTRACT

The present invention generally concerns novel proteins which bind to the intracellular domains of the p55 and p75 TNF-Rs and the FAS-R, which are capable of modulating the function of the p55 and p75 TNF-Rs and the FAS-R, and the DNA sequences which encode them. The present invention also concerns new soluble oligomeric TNF-Rs, oligomeric FAS-Rs and oligomeric receptors having a mixture of TNF-Rs and FAS-Rs. In addition, the present invention concerns methods of preparation and uses of all of the aforementioned.

14 Claims, 19 Drawing Sheets

5'GAATTCGGCACGAGCGGCACGAGGACAGAGTGAGACTCTGTCTCTTAAAATAATAATA
AAATAAAAATAAAATGTGGGGCCGGGCAAGGTGGCTCATGCCTGTAATCCCAGCACCTT
GGGAGGCTGAGGCAGGAGGATTGCCTAAGCCCAGGAGTTTGACATCAGCCTGGGCAACAT
GGTGAAACCCCATCTCTACAAAAAATGCAAAAATTAGCCAGGTGTGGTGGGTGTGCTCCT
ATAGTCTCAGCTACTCAGGAGGCTGAGGTAGAGGGGATCACCTGAGCCCAGGAAGTTTGG
AGGCTATAGTGAGCTGAAGACCCGCACCATTGCACGCCAGCCTGGAGCAAGAGACNCTGT
CTCCACATAAATAAATAAATAAATAAAAGTGGGGAACTTCTGTGTTAAGTCAGAAGGCAC
CACACAATTTGNATAGCCANCAACCATATTCAATACCCAATCTCTTTATTGCAATATAAG
TATTTGTAAACCCCTACACAAATATTCCCAAGAATAAGTTGGAATATAAATTACTATATC
AATCANCCAATAAAAATAAACACATACAGTATTTATTTCCTGTTGCTCCATATAAAGCTT
TGCTATTTCAATATAAAGCTTACCTAGTATGGTCATTTGAGCCTGAGCAGAGAATATGCC
CAAGCTCGTGCCGAATTC....GGCGNTCTGACTCTCTACTGAACCAAGACTGAATCAGA
GAGACTCGAGTGCNCTTATTTGATTAANCCCAAATTATTGAAACCTNTGATTTTTTCTGG
AGGNGGATGATAAAGATGTGAAAGTGTGATGAACAGTGTGTATCCCTACTCTTGATCCTG
GAACCAGACAAGCAAGAAGCTTTGATTGAAAGCCTATGTGAAAAGCTGGTCAAATTTCGC
GAAGGTGAACGCCCGTCTCTGAGACTGCAGTTGTTAAGCAACCTTTTCCACGGGATGGAT
AAGAATACTCCTGTAAGATACACAGTGTATTGCAGCCTTATTAAAGTGGCAGCATCTTGT
GGGGCCATCCAGTACATCCCAACTGAGCTGGATCAAGTTAGAAAATGGATTTCTGACTGG
AATCTCACCACTGAAAAAAAGCACACCCTTTTAAGACTACTTTATGAGGCACTTGTGGAT
TGTAAGAAGAGTGATGCTGCTTCAAAAGTCATGGTGGAATTGCTCGGAAGTTACACAGAG
GACAATGCTTCCCAGGCTCGAGTTGATGCCCACAGGTGTATTGTACGAGCATTGAAAGAT
CCAAATGCATTTCTTTGTGACCACCTTCTTACTTTAAAACCAGTCAAGTTTGTGGAAGGC
GAGCTTATTCATGATCTTTTAACCATTTGTGTGAGTGCTAAATTGGCATCATATGTCAAG
TTTTATCAGAATAATAAAGACTTCATTGATTCACTTGGCCTGTTACATGAACAGAATATG
GCAAAAATGAGACTACTTACTTTTATGGGAATGGCAGTAGAAAATAAGGAAATTTCTTTT
GACACAATGCAGCAAGAACTTCAGATTGGAGCTGATGATGTTGAAGCATTTGTTATTGAC
GCCGTAAGAACTAAAATGGTCTACTGCAAAATTGATCAGACCCAGAGAAAAGTAGTTGTC
AGTCATAGCACACATCGGACATTTGGAAAACAGCAGTGGCAACAACTGTATGACACACTT
AATGCCTGGAAACAAAATCTGAACAAAGTGAAAAACAGCCTTTTGAGTCTTTCTGATACC
TGAGTTTTTATGCTTATAATTTTTGTTCTTTGAAAAAAAGCCCTAAATCATAGTAAAAC
ATTATAAACTAAAAAAAAAAAAAAAAAAACTCGAG 3'

FIG. 1C (c) <u>75.16</u>

5' GTCCGGTTTACTTTAACTTAGTTTTGCATAGTTCTAGTGCACGTGAAATTGAAAAGTTA
TTTCCCTTTAGCTGTGTTATTATAGAGCAGAAATTCTGTTTTTAAAAATTAGCCTAAGATA
TACTTGTTTTTGTAAAGAAAAATATTTAATGCTTGAACAAAATAAATTGGAGTTGGAGTAG
AATGTAGTTTGAGGAAATTTGCAGCTTCCAATGCCTCTG.....CAGAGGCATTGGAAGCT
GCAAATTTCCTCAAACTACATTCTACTCCAACTCCAATTTATTTTGTTCAAGCATTAAATA
TTTTTCTTTACAAAAACAAGTATATCTTAGGCTAATTTTTAAAAACAGAATTTCTGCTCTA
TAATAACACAGCTAAAGGGAAATAACTTTTCAATTTCACGTGCACTAGAACTATGCAAAAC
TAAGTTAAAGTAAACCGGAC 3'

FIG. 1D

```
55.11pep  Length: 900  March 10, 1995  19:08  Type: P  Check:
9498  ..

1  RVQPQQSPAA  APGGTDEKPS  GKERRDAGDK  DKEQELSEED  KQLQDELEML
  51  VERLGEKDTS  LYRPALEELR  RQIRSSTTSM  TSVPKPLKFL  RPHYGKLKEI
 101  YENMAPGENK  RFAADIISVL  AMTMSGEREC  LKYRLVGSQE  ELASWGHEYV
 151  RHLAGEVAKE  WQELDDAEKV  QREPLLTLVK  EIVPYNMAHN  AEHEACDLLM
 201  EIEQVDMLEK  DIDENAYAKV  CLYLTSCVNY  VPEPENSALL  RCALGVFRKF
 251  TRFPEALRLA  LMLNDMELVE  DIFTSCKDVV  VQKQMAFMLG  RHGVFLELSE
 301  DVEEYEDL*TE  IMSNVQLNSN  FLALARELDI  MEPKVPDDIY  KTHLENNRFG
 351  GSGSQVDSAR  MNLASSFVNG  FVNAAFGQDK  LLTDDGNKWL  YKNKDHGMLS
 401  AAASLGMILL  WDVDGGLTQI  DKYLYSSEDY  IKSGALLACG  IVNSGVRNEC
 451  DPALALLSDY  VLHNSNTMRL  GSIFGLGLAY  AGSNREDVLT  LLLPVMGDSK
 501  SSMEVAGVTA  LACGMIAVGS  CNGDVTSTIL  QTIMEKSETE  LKDTYARWLP
 551  LGLGLNHLGK  GEAIEAILAA  LEVVSEPFRS  FANTLVDVCA  YAGSGNVLKV
 601  QQLLHICSEH  FDSKEKEEDK  DKKEKKDKDK  KEAPADMGAH  QGVAVLGIAL
 651  IAMGEEIGAE  MALRTFGHLL  RYGEPTLRRA  VPLALALISV  SNPRLNILDT
 701  LSKFSHDADP  EVSYNSIFAM  GMVGSGTNNA  RLAAMLRQLA  QYHAKDPNNL
 751  FMVRLAQGLT  HLGKGTLTLC  PYHSDRQLMS  QVAVAGLLTV  LVSFLDVRNI
 801  ILGKSHYVLY  GLVAAMQPRM  LVTFDEELRP  LPVSVRVGQA  VDVVGQAGKP
 851  KTITGFQTHT  TPVLLAHGER  AELATEEFLP  VTPILEGFVI  FGRTPIMISK
```

Underlined: Homolgy to SEN3
BOLD – Basic cluster, nuclear localisation signal
* end of head

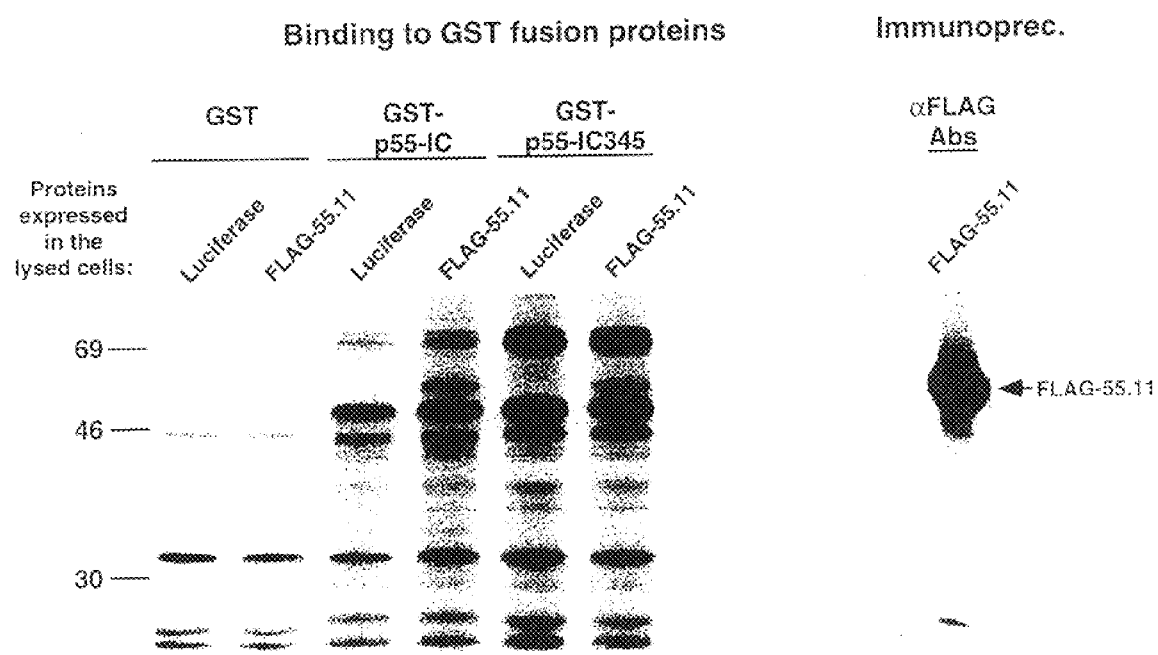

FIG. 4A

```
55.11(human)   ..RVQPQQSPAAAPGTDEKPSGKERRDAGDKDKEQE..LSEEDKQLQDELEMIVERLGE     56
YHR027C(yeast) KKMVDESDKKQQTIDEQSQISPEKQTPNKKDKKKEEEQLSEEDAKLKTDLELIVERLKE    60
SEN3(yeast)    ..........................................MSLTTAAPLLALLRE    15

55.11(human)   KDTSLYRPALEELRRQIRSSTTSMTSVPKPLKFLRPHYGKLKEIYENMAPGENKRFAADI  116
YHR027C(yeast) DDSSIYEASLNALKESIKNSTSSMTAVPKPLKFLRPTYPDLCSIYDKWTDPNLKSSLADV  120
SEN3(yeast)    NQDSVKTYALESINNVVD...........QLWSEISNELPDIEALYDDDTFSDREMAA    62

55.11(human)   ISVLAMTMS..GERECLKYRLVGSQEELASWGHEYVRHLAGEVAKEWQELDDAEKVQ...  171
YHR027C(yeast) LSILAMTYSENGKHDSLRYRLLSDVSDFEGWGHEYIRHLALEIGEVYNDQVEKDAEDETS  180
SEN3(yeast)    LIASKVYYNLGEYESAVKYALAAKDRFDIDEKSQFVETIVSKSIEMYVQEASKQYTKDEQ  122

55.11(human)   .........REPLLTLVKEIVPYNMAHNAEHEACDLLMEIEQVDMLEKDID            213
YHR027C(yeast) SDGSKSDGSAATSGFEFSKEDTLRLCLDIVPYFLKHNGEEDAVDLLLEIESIDKLPQFVD  240
SEN3(yeast)    FYTKDIIDPKLTSIFERMIEKCLKASELKLALGIALEGYRLDIIESALKSKLDQDSTSEN  182

55.11(human)   ENAYAKVCLYLTSCVNYVPEPENSALLRCALGVFRKFTRFPEALRLALMLNDMELVEDIF  273
YHR027C(yeast) ENTFQRVCQIMVACVPLLPPPEDVAFLKTAYSIYLSQNELTDAIALAVRLGEEDMIRSVF  300
SEN3(yeast)    VKINYLLTLAITTVTNSKFRSSILRKSFDFLMNMPNCDYLTLNKVVVNLNDAGLALQLF    242

55.11(human)   TSCKDVVVQKQMAFMLGRHGVFLELSEDVEEYEDLTEIMSNVQLNSNFIALARELDIMEP  333
YHR027C(yeast) DATSDPVMHKQLAYILAAQKTSF......EYEGVQDIIGNGKLSEHFLYLAKELNLTGP  353
SEN3(yeast)    KKLKE....ENDEGLSAQIAFDLVSSASQQLLEIIVTELTAQGYDPALLNILSGLPTCDY  298

55.11(human)   KVPDDIYKTHLENNRFGGSGSQVDS..ARMNLASSFVNGFVNAAFGQDKLLTDDGNKWLY  391
YHR027C(yeast) KVPEDIYKSHLDNSKSVFSSAGLDS..AQQNLASSFVNGFLNLGYCNDKLIVDNDN.WVI  410
SEN3(yeast)    YNTFLLNNKNIDIGLLNKSKSSLDGKFSLFHTAVRLANGFMHAGTTDNSFIKAN.LPWLG  357

55.11(human)   KNKDHGMLSAAASLGMILLMDVDGGLTQIDKYL...YSSEDYIKSGALLACGIVNSGVRN  448
YHR027C(yeast) KTKGDGMTSAVASIGSIYQWNLD.GLQQLDKYL...YVDEPEVKAGALLGIGISASGVHD  466
SEN3(yeast)    KAQNWAKFTATASLGVIHKGNLLEGKKVMAPYLPGSRASSRFIKGGSLYGLGLIYAGFGR  417

55.11(human)   .ECDPALALISDIYVLHNSNT....MRLGSIFGLGLAYAGSNREDVLTILLPVMGDSKSSM  503
YHR027C(yeast) GEVEPALLLLQDIVTNPDTK....ISSAAILGLGIAFAGSKNDEVLGLLLPIAASTDLPI  522
SEN3(yeast)    DTTDYLKNIIVENSGTSGDEDVDVLLHGASLGIGLAAMGSANIEVYEALKEVLYNDSATS  477

55.11(human)   EVAGVTALACGMIAVGSCNGDVTSTILQTIMEKSETELKDTYARWLPLGLGLNHLGKGEA  563
YHR027C(yeast) ETAAMASLALAHVFVGTCNGDITTSIMDNFLERTAIELKTDWVRFLALALGILMGQGEQ  582
SEN3(yeast)    GENAALGMGLCMLGTGKPEA......IHDMFTYSQETQHGNITRGLAVGLALINYGRQEL  531
```

FIG. 4B

```
55.11(human)     IEAILAALEVVSEPFRSFANTLVDVCAYAGSGNVLKVQQLLH........................  605
YHRO27C(yeast)   VDDVLETISAIEHPMTSAIEVLVGSCAYTGTGDVLLIQDLLHRLTPKNVKGEEDAD.........  638
SEN3(yeast)      ADDLITKMLASDESLLRYGGAFTIALAYAGTGNNSAVKRLLHVAVSDSNDDVRRAAVIAL......  591

55.11(human)     ................EEETAEGQTNSISDFLGEQVNEPTKNEEAEIEVDEMEVDAEGEEVE    605
YHRO27C(yeast)   ...............................................................  684
SEN3(yeast)      GFVLLRDYTTVPRIVQLLSKSHNAHVRCGTAFALGIACAGKGLQSAIDVLDPLTKDPVDF     651

55.11(human)     ............ICSEHFDSKEKEEDKDKKEKKDKDKKEAPADMGAHQGVAVLG           647
YHRO27C(yeast)   VKAEITEKKNGESLEGEEIKSEEKKGKSSDKDATTDGKNDDEEEEKEAGIVDELAYAVLG       744
SEN3(yeast)      VRQAAMIALSMILIQQTEKLNPQVADINKNFLSVITNKHQEGLAKFGACVAQGIMNAGGR       711

55.11(human)     IALIAMGEEIGAEMALRTFGHLLRYGEPTLRRAVPLALALISVSNPRLNIL...DTLSKF      704
YHRO27C(yeast)   IALIALGEDIGKEMSLRHFGHLMHYGNEHIRRMVPLAMGIVSVSDPQMKVF...DTLTRF      801
SEN3(yeast)      NVTIQLENADTGTLDTKSVVGLVMFSQFWYWFPLAHFLSLSFTPTTVIGIRGSDQAIPKF      771
A.thaliana(plant) WXIRSDERVLQYGEQNIRRAVPLALGLLCISNPKVTVM...DTLSRL                  44
C.elegans(nematode) ..............................................................    0

55.11(human)     SHDADPEVSYNSIFAMGMVGSGTNNARLAAMLRQLAQYHAKDPNNLFMVRLAQGLTHLGK      764
YHRO27C(yeast)   SHDADLEVSMNSIFAMGLCGAGTNNARLAQLLRQLASYYSREQDALFITRLAQGLLHLGK      861
SEN3(yeast)      QMNCYAKEDAFSYPRMYEEASGKEVEKVATAV.......LSTTARAKARAKKTK            818
A.thaliana(plant) SHDRFRSCNGSNYLPWIDRRWNQQCKDSWHA*KSLQLLLQGCPXFFSVCASLKGFXHMGK    103
C.elegans(nematode) ..............................................................    0

55.11(human)     GTLTLCPYHSDRQLMSQVAVAGLLITVLVSFLDVRNIILGKSHYVLYGLVAAMQPRMLVTF     824
YHRO27C(yeast)   GTMTMDVFN.DAHVLNKVTLASILTTAVGL..VSPSFMLKHHQLFYMLNAGIRPKFILAL      918
SEN3(yeast)      KEKGPNEEEKKKEHEEREKEKERETNKKGIKETKENDEEFYKNKYSSKPYKVDNMTRILPQQ    878
A.thaliana(plant) GLLTLNPFHSERAXFLXXNPDFPWV*GXNFLQXXXFXIET................         142
C.elegans(nematode) .............................................MQPRMLTTL            9

55.11(human)     DEE......LRPLPVSVRVGQAVDVGQAGKPKTITGFQTHTTPVLLAHGERAELATEEF      878
YHRO27C(yeast)   NDEG......EPIKVNVRVGQAVETVGQAGRPKKITGWITQSTPVLLNHGERAELETDEY      972
SEN3(yeast)      SRYISFIKDDRFVPVRKFKGNNGVVVLRDREPKE.........PVALIETVRQMKDVNAP    929
A.thaliana(plant) ................................................                142
C.elegans(nematode) VEDEMKPGSLKQINVSVRVGQPVDVVAQAGKPKTITGFQTHTTPVLLAHGERAELANDEY    69

55.11(human)     LPVTPILEGFVIFGRT...PIMISK..900
YHRO27C(yeast)   ISYTSHIEGVVILKKNPDYREEE....995
SEN3(yeast)      LPTPFKVDDNVDFPSA...........945
A.thaliana(plant) ...........................142
C.elegans(nematode) LSVTPHLEGLVILKKNPDYQPVVVSTKK97
```

FIG. 10

F2 clone

ATCAGTGTCACTACGGA TAGTGATGACACTC ACAGGAGGGCTGGGGTATCTgGAATGATGATT
GGCTGATGCTGGTCTTGGACAGGAACTAGGGAA TTATAAGAAGATGTGGTACGAAGAGGACTAC
TCCCANCCAGAGAATAAACTTGAGAAGGCAGGACTTCCAGAGAGGATTTGGATGAAACTGGAGC
AGACTGC TTAT TCTACTT TGAAGGGAGGGAACTAGACTGTTGTTCTGACAACATGGGCAACA
CCAACATTCAGAGGCTGAGCAGTNGCCAAGGNCACATGGTTGGTCAGCAAAGATGGCTGCTGCA
TAATAGTGCTGCTACTGGTCGNCATGAGAGAGTGGGGCATTCCCCAGTCAGCTAGCTGGGCTGCT
CCCCAT......

NNNNNNNNNNNNNNNNNNNNN......

cctctcagtt atctctgttggagtagtcctcttcg taccacatcttcttataattccctagttcc tgtccaagaccagcatcagcCAA
TCATCAT TCCAGATACCCCCAGCCCTCCTGTGAGTGTCATCACT ATcCG TAGTGACACTGAT
GAaGAaGAGGACAACAACAAATACAAGCCCAATAGCTCGAGCCTGAAGGcGAGGTCT AATGTCAT
CAGTTATG TCACTGTCAATGAT TCT CCAGACTCTGACTCCTCCCTGAGCAGCCCACATTCCA
CAGCCACTCTGAGTGCTCTGcGGGG CAACAGTGGGACCCTTCTGGAGGGACCTGGCAGACC
TGCAGCAGATGGcAT TGGCACCCGT ACTATCATTGTACCTGAGCGGCCGC..........

FIG. 11

F9 clone

GGGAGCCTGTGCACCCGATGTCACCATGAAGCCACTGCCCT TCTAT GAAGTCTATGGGGAGCTCATCCGAC
CCACCACCCTTGGCTCCACCTCCAGCCAGAGGTTCGAGGAAGCCCAC TTCACCTTCGCGCTCACTCCCAGC
AGCTGCAGCAGAT TCTCACGTCCAGGGAGGTTATGCCAGGAGCCAAG TGTGATTACACCATACAAGTGCAGC
TCAGA TTC TGTCTCTGTGAGACCAGCTGCCCTCAGGAGGACTATTTCCCCCCTAACCTCTT TGT TA AGGTTA
ATGGGAAACTCTGCCCCCTGCCGCGGGTTACCTCCCTCCAACCCAAGAATGGAGCTGAGCCCAAGAGGCCCAGC
CGTCCGATCAACATCAC ACCCTTGGCTCGACTCTCAGCCACTGTCCCCAACACCATCG TAGTT AAT TGGGTC
ATC TTGAAGTT T ..........................
NNNNNNNNNNNNNNNNNNNNNNNNNNNNNNNNNN
tCC AACACCATGCGTAGA T AAATTGgTC ATCTGAGTT TGGaCCGGAATTACTCC tTGTC CGTGT ACCCTGGTG
AGGCAATTGACTGCAGGG ACCCTTCTACACAAACTCAGAGCCAAGGGGATCCGGAATCCAGACCATTCCCGG
GCACTGATCAAGGAGAA ACTGACTGCTGAACCCCGACAGTGAAGTGGCTACTAC AAGTCTCCGGGTGTCACTC
ATGTGCCCGCTAGGGAAGATGCGCCTG ACTGTCCCGTCGTGCCCTCACCTGTGCCCAT CTGCAGAGTTC
GATGCTG cCCTTT ATCT AcAGA Tg aaT GAGAagAAGCCGACATGGACGTGTCCTGTGCGTGACAAGAAGGCT
CCCTATG AGTCGcTGAT TAT TGAT GGTTT AT TCATGGAAAT TCT TAATTCCT GTTCGGATTGTGATGAGATC
CAGTTCA TGGAAGATGGATCCTGG TGTCCGATGAAACCCAAGGAGGAGCATCAGAGGTTTGCCCCCGCCA
GGGTATGGGCTGGaTGGTCTCCA GTACAGCGCAGtCCAGGGAATTCAGCCAGGAGTAAGAAGAGGGTC
GA aGTCAT TGACTTGACCATCGA AAGCTCATCAGATGAGGag gAT TTgCCCCCACCAAGAAGAACTGCCCT
GT CACCTCAGCGCCCTG CAATGGCACACTGGGCAGAGCCCTGAcCTCTGGTCACCAGcCATCCTCG
GT GCTGCGGAGCCCTG CAATGGCACACTGGGCAGAGCCCTGACTGACTTCCTGTCTAGTCTCCGCTACCA
CC TGCCT TCCCACTGGGGG tT GACATCCAAGGTT TAGATTT TATTT TCTTT TCTTCAGACTGAGAGTCAGAA
T TACGGGC CTTCAGT T T ATCAT TCG...................
NNNNNNNNNNNNNNNNNNNNNNNNNNNNNNN
CCACT TCC TGGCCCAC TGCCCCCAAACTGGGACTCTCACCGcAAGCTCACCGcCCCCCTCCTGGT
CGTGTC AGCAGC ATTG TGGCTCCTGGGAGC TCCTTGAGGGAAGGGCATGGAGGACC CCTGCCTTCAGGTC
CCTCT T TGACTGG CTG TCGGTCAGACGTCA T TTCCTTGGACT GAGCTT TTT GGATT ATGAAATCAATCTCC
A TTGGCCCCAGCA CTG AGCAGGATCACGTTG T GGGTTCCGAACCCCTGGCTCTG ATCCCTCAGGGGTC
A TTGGCCAAAGGC CAG GCCAAGCTTCATGG A TACCTGCT TTGGCCT TATCGCTGCCTAACAGGCCAGT
AC TCACAGGGTTA AC A TT TAAC CTTTTATGGTGGCCCG

FIG. 12

DD11 clone

```
......AATTCGGCACGAGGTTG TGCTGTGGGGAAGGGAGAAGGAGAAGGATTTGTAAACCCCGGAGGCGAGGTTCTGCTTACCC
GAGGCCGCTGCTGTGCGGAGACCCCGGGTGAAGCCACCGTCATCATGTCTGACCAGGAAGCCAAAACCTTCc
AAC TGAGGACTTGGGGGAT AAGAAGGAAGGTGAA TATA TTAAACTCAAAGTCATTGGACAGGATAGCAGTGA
GA TTCAC TTCAAAG TGAAA ATGACAACACA TCTC AAGAAACTCAAAGAATCATACTGTCAAAGACAGGTGT
TCC AATG AATTCAC TCAGG TT TCTCT TTGAGGGTC AGAGAATTGCTGATAATCATACTCCAAAAGAACTGGG
AAT GGAGAAGAAAGA TTGT GA TT tGA aGTTT TATCAGGAACAAACGGGGGTCATTCAACAGcTT......
......
```

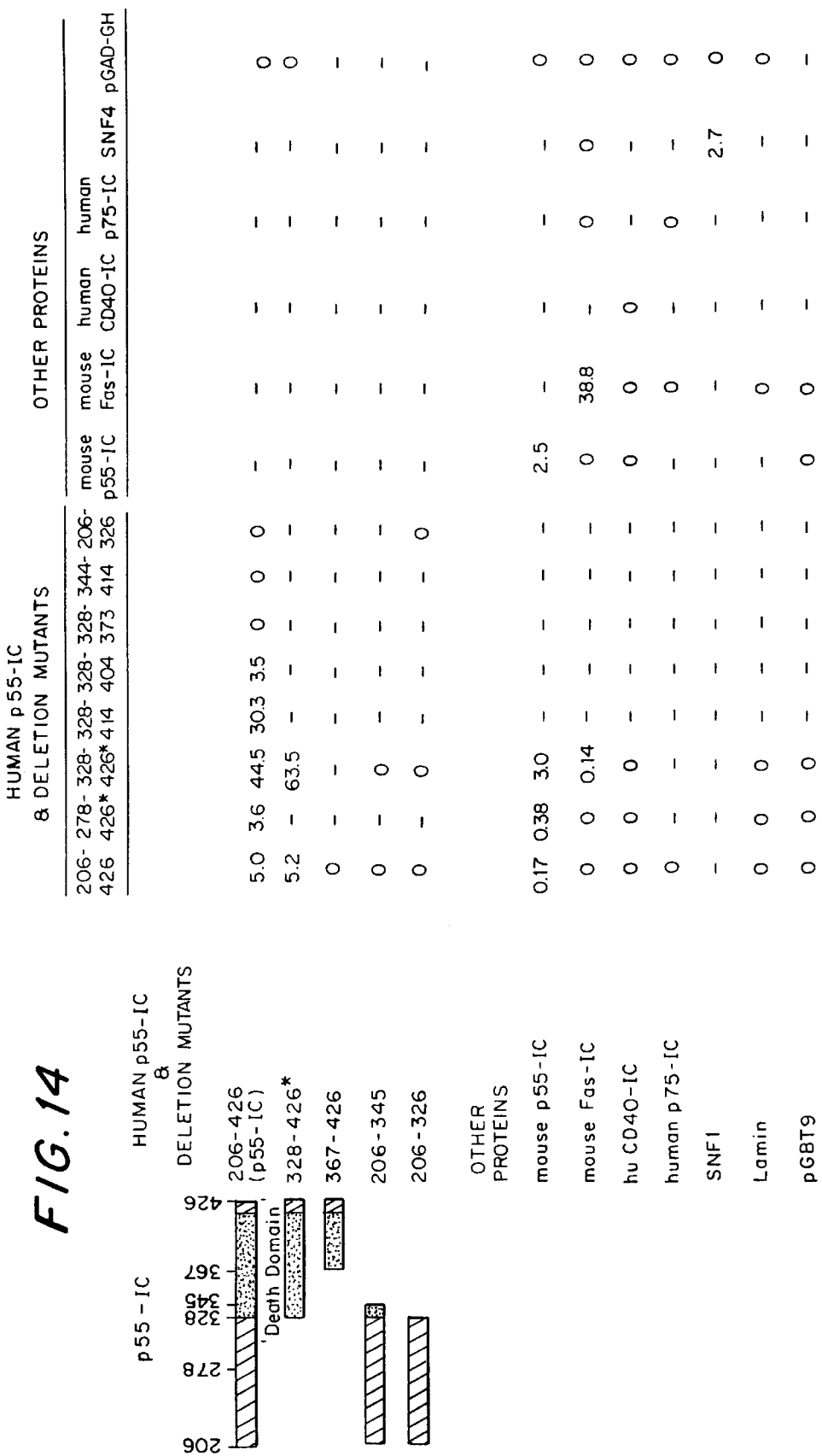

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO: 1:

ACCATGGGCC TCTCCACCGT G                                              21

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

ACGCGTCGAC TGTGGTGCCT GAGTCCTC                                       28

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

ACGCGTCGAC CGCTACCAAC GGTGGAAG                                       28

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

TCATCTGAGA AGACTGGG                                                  18

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

ACGCGTCGAC AAGAGAAAGG AAGTACAG                                       28

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CTAGACCAAG CTTTGGAT                                                      18

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

ACGCGTCGAC CCCGCGACGC TGTACGCC                                           28

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

ACGCGTCGAC GATGTTGACT TGAGTAAA                                           28

(2) INFORMATION FOR SEQ ID NO: 9:

(i) SEQUENCE CHARACTERISTICS:
        (A) LENGTH: 2866 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
ATTCGGGTGC AGCCCCAGCA GTCTCCAGCG GCGGCCCCCG GCGGCACGGA CGAGAAGCCG      60

AGCGGCAAGG AGCGGCGGGA TGCCGGGGAC AAGGACAAAG AACAGGAGCT GTCTGAAGAG     120

GATAAACAGC TTCAAGATGA ACTGGAGATG CTCGTGGAAC GACTAGGGGA GAAGGATACA     180

TCCCTGTATC GACCAGCGCT GGAGGAATTG CGAAGGCAGA TTCGTTCTTC TACAACTTCC     240

ATGACTTCAG TGCCCAAGCC TCTCAAATTT CTGCGTCCAC ACTATGGCAA ACTGAAGGAA     300

ATCTATGAGA ACATGGCCCC TGGGGAGAAT AAGCGTTTTG CTGCTGACAT CATCTCCGTT     360

TTGGCCATGA CCATGAGTGG GGAGCGTGAG TGCCTCAAGT ATCGGCTAGT GGGCTCCCAG     420

GAGGAATTGG CATCATGGGG TCATGAGTAT GTCAGGCATC TGGCAGGAGA AGTGGCTAAG     480

GAGTGGCAGG AGCTGGATGA CGCAGAGAAG GTCCAGCGGG AGCCTCTGCT CACTCTGGTG     540

AAGGAAATCG TCCCCTATAA CATGGCCCAC AATGCAGAGC ATGAGGCTTG CGACCTGCTT     600

ATGGAAATTG AGCAGGTGGA CATGCTGGAG AAGGACATTG ATGAAAATGC ATATGCAAAG     660

GTCTGCCTTT ATCTCACCAG TTGTGTGAAT TACGTGCCTG AGCCTGAGAA CTCAGCCCTA     720

CTGCGTTGTG CCCTGGGTGT GTTCCGAAAG TTTACCCGCT TCCCTGAAGC TCTGAGATTG     780

GCATTGATGC TCAATGACAT GGAGTTGGTA AAGACATCT TCACCTCCTG CAAGGATGTG      840

GTAGTACAGA AACAGATGGC ATTCATGCTA GGCCGGCATG GGGTGTTCCT GGAGCTGAGT     900

GAAGATGTCG AGGAGTATGA GGACCTGACA GAGATCATGT CCAATGTACA GCTCAACAGC     960
```

```
AACTTCTTGG CCTTAGCTCG GGAGCTGGAC ATCATGGAGC CCAAGGTGCC TGATGACATC    1020

TACAAAACCC ACCTAGAGAA CAACAGGTTT GGGGGCAGTG GCTCTCAGGT GGACTCTGCC    1080

CGCATGAACC TGGCCTCCTC TTTTGTGAAT GGCTTYGTGA ATGCAGCTTT TGGCCAAGAC    1140

AAGCTGCTAA CAGATGATGG CAACAAATGG CTTTACAAGA ACAAGGACCA CGGAATGTTG    1200

AGTGCAGCTG CATCTCTTGG GATGATTCTG CTGTGGGATG TGGATGGTGG CCTCACCCAG    1260

ATTGACAAGT ACCTGTACTC CTCTGAGGAC TACATTAAGT CAGGAGCTCT TCTTGCCTGT    1320

GGCATAGTGA ACTCTGGGGT CCGGAATGAG TGTGACCCTG CTCTGGCACT GCTCTCAGAC    1380

TATGTTCTCC ACAACAGCAA CACCATGAGA CTTGGTTCCA TCTTTGGGCT AGGCTTGGCT    1440

TATGCTGGCT CAAATCGTGA AGATGTCCTA ACACTGCTGC TGCCTGTGAT GGGAGATTCA    1500

AAGTCCAGCA TGGAGGTGGC AGGTGTCACA GCTTTAGCCT GTGGAATGAT AGCAGTAGGG    1560

TCCTGCAATG GAGATGTAAC TTCCACTATC CTTCAGACCA TCATGGAGAA GTCAGAGACT    1620

GAGCTCAAGG ATACTTATGC TCGTTGGCTT CCTCTTGGAC TGGGTCTCAA CCACCTGGGG    1680

AAGGGTGAGG CCATCGAGGC AATCCTGGCT GCACTGGAGG TTGTGTCAGA GCCATTCCGC    1740

AGTTTTGCCA ACACACTGGT GGATGTGTGT GCATATGCAG GCTCTGGGAA TGTGCTGAAG    1800

GTGCAGCAGC TGCTCCACAT TTGTAGCGAA CACTTTGACT CCAAAGAGAA GGAGGAAGAC    1860

AAAGACAAGA AGGAAAAGAA AGACAAGGAC AAGAAGGAAG CCCCTGCTGA CATGGGAGCA    1920

CATCAGGGAG TGGCTGTTCT GGGGATTGCC CTTATTGCTA TGGGGGAGGA GATTGGTGCA    1980

GAGATGGCAT TACGAACCTT TGGCCACTTG CTGAGATATG GGGAGCCTAC ACTCCGGAGG    2040

GCTGTACCTT TAGCACTGGC CCTCATCTCT GTTTCAAATC CACGACTCAA CATCCTGGAT    2100

ACCCTAAGCA AATTCTCTCA TGATGCTGAT CCAGAAGTTT CCTATAACTC CATTTTTGCC    2160

ATGGGCATGG TGGGCAGTGG TACCAATAAT GCCCGTCTGG CTGCAATGCT GCGCCAGTTA    2220

GCTCAATATC ATGCCAAGGA CCCAAACAAC CTCTTCATGG TGCGCTTGGC ACAGGGCCTG    2280

ACACATTTAG GGAAGGGCAC CCTTACCCTC TGCCCCTACC ACAGCGACCG GCAGCTTATG    2340

AGCCAGGTGG CCGTGGCTGG ACTGCTCACT GTGCTTGTCT CTTTCCTGGA TGTTCGAAAC    2400

ATTATTCTAG GCAAATCACA CTATGTATTG TATGGGCTGG TGGCTGCCAT GCAGCCCCGA    2460

ATGCTGGTTA CGTTTGATGA GGAGCTGCGG CCATTGCCAG TGTCTGTCCG TGTGGGCCAG    2520

GCAGTGGATG TGGTGGGCCA GGCTGGCAAG CCGAAGACTA TCACAGGGTT CCAGACGCAT    2580

ACAACCCCAG TGTTGTTGGC CCACGGGGAA CGGGCAGAAT TGGCCACTGA GGAGTTTCTT    2640

CCTGTTACCC CCATTCTGGA AGGTTTTGTT ATCTTCGGAA GAACCCCAAT TATGATCTCT    2700

AAGTGACCAC CAGGGGCTCT GAACTGCAGC TGATGTTATC AGCAGGACAT GCATCCTGCT    2760

GCCAAGGGTG GACACGGCTG CAGACTTCTG GGGGAATTGT CGCCTCCTGC TCTTTTGTTA    2820

CTGAGTGAGA TAAGGTTGTT CAATAAAGAC TTTTATCCCC AAGGTC                   2866
```

(2) INFORMATION FOR SEQ ID NO: 10:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
GAATTCGGCA CGAGCGGCAC GAGGACAGAG TGAGACTCTG TCTCTTAAAA TAATAATAAA    60
```

```
AATAAAAATA AAATGTGGGG CCGGGCAAGG TGGCTCATGC CTGTAATCCC AGCACCTTGG      120

GAGGCTGAGG CAGGAGGATT GCCTAAGCCC AGGAGTTTGA CATCAGCCTG GGCAACATGG      180

TGAAACCCCA TCTCTACAAA AAATGCAAAA ATTAGCCAGG TGTGGTGGGT GTGCTCCTAT      240

AGTCTCAGCT ACTCAGGAGG CTGAGGTAGA GGGGATCACC TGAGCCCAGG AAGTTTGGAG      300

GCTATAGTGA GCTGAAGACC CGCACCATTG CACGCCAGCC TGGAGCAAGA GACNCTGTCT      360

CCACATAAAT AAATAAATAA ATAAAAGTGG GGAACTTCTG TGTTAAGTCA GAAGGCACCA      420

CACAATTTGN ATAGCCANCA ACCATATTCA ATACCCAATC TCTTTATTGC AATATAAGTA      480

TTTGTAAACC CCTACACAAA TATTCCCAAG AATAAGTTGG AATATAAATT ACTATATCAA      540

TCANCCAATA AAAATAAACA CATACAGTAT TTATTTCCTG TTGCTCCATA TAAAGCTTTG      600

CTATTTCAAT ATAAAGCTTA CCTAGTATGG TCATTTGAGC CTGAGCAGAG AATATGCCCA      660

AGCTCGTGCC GAATTC                                                     676
```

(2) INFORMATION FOR SEQ ID NO: 11:

(i) SEQUENCE CHARACTERISTICS:
        (A) LENGTH: 1153 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
GGCGNTCTGA CTCTCTACTG AACCAAGACT GAATCAGAGA GACTCGAGTG CNCTTATTTG       60

ATTAANCCCA AATTATTGAA ACCTNTGATT TTTTCTGGAG GNGGATGATA AAGATGTGAA      120

AGTGTGATGA ACAGTGTGTA TCCCTACTCT TGATCCTGGA ACCAGACAAG CAAGAAGCTT      180

TGATTGAAAG CCTATGTGAA AAGCTGGTCA AATTTCGCGA AGGTGAACGC CGTCTCTGA       240

GACTGCAGTT GTTAAGCAAC CTTTTCCACG GGATGGATAA GAATACTCCT GTAAGATACA      300

CAGTGTATTG CAGCCTTATT AAAGTGGCAG CATCTTGTGG GGCCATCCAG TACATCCCAA      360

CTGAGCTGGA TCAAGTTAGA AAATGGATTT CTGACTGGAA TCTCACCACT GAAAAAAAGC      420

ACACCCTTTT AAGACTACTT TATGAGGCAC TTGTGGATTG TAAGAAGAGT GATGCTGCTT      480

CAAAAGTCAT GGTGGAATTG CTCGGAAGTT ACACAGAGGA CAATGCTTCC CAGGCTCGAG      540

TTGATGCCCA CAGGTGTATT GTACGAGCAT TGAAAGATCC AAATGCATTT CTTTGTGACC      600

ACCTTCTTAC TTTAAAACCA GTCAAGTTTG TGGAAGGCGA GCTTATTCAT GATCTTTTAA      660

CCATTTGTGT GAGTGCTAAA TTGGCATCAT ATGTCAAGTT TTATCAGAAT AATAAAGACT      720

TCATTGATTC ACTTGGCCTG TTACATGAAC AGAATATGGC AAAAATGAGA CTACTTACTT      780

TTATGGGAAT GGCAGTAGAA AATAAGGAAA TTTCTTTTGA CACAATGCAG CAAGAACTTC      840

AGATTGGAGC TGATGATGTT GAAGCATTTG TTATTGACGC CGTAAGAACT AAAATGGTCT      900

ACTGCAAAAT TGATCAGACC CAGAGAAAAG TAGTTGTCAG TCATAGCACA CATCGGACAT      960

TTGGAAAACA GCAGTGGCAA CAACTGTATG ACACACTTAA TGCCTGGAAA CAAAATCTGA     1020

ACAAAGTGAA AAACAGCCTT TTGAGTCTTT CTGATACCTG AGTTTTTATG CTTATAATTT     1080

TTGTTCTTTG AAAAAAAAGC CCTAAATCAT AGTAAAACAT TATAAACTAA AAAAAAAAA      1140

AAAAAACTC GAG                                                        1153
```

(2) INFORMATION FOR SEQ ID NO: 12:

(i) SEQUENCE CHARACTERISTICS:

(A) LENGTH: 220 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTCCGGTTTA CTTTAACTTA GTTTTGCATA GTTCTAGTGC ACGTGAAATT GAAAAGTTAT        60

TTCCCTTTAG CTGTGTTATT ATAGAGCAGA AATTCTGTTT TTAAAAATTA GCCTAAGATA       120

TACTTGTTTT TGTAAAGAAA AATATTTAAT GCTTGAACAA AATAAATTGG AGTTGGAGTA       180

GAATGTAGTT TGAGGAAATT TGCAGCTTCC AATGCCTCTG                             220

(2) INFORMATION FOR SEQ ID NO: 13:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

CAGAGGCATT GGAAGCTGCA AATTTCCTCA AACTACATTC TACTCCAACT CCAATTTATT        60

TTGTTCAAGC ATTAAATATT TTTCTTTACA AAAACAAGTA TATCTTAGGC TAATTTTTAA       120

AAACAGAATT TCTGCTCTAT AATAACACAG CTAAAGGGAA ATAACTTTTC AATTTCACGT       180

GCACTAGAAC TATGCAAAAC TAAGTTAAAG TAAACCGGAC                             220

(2) INFORMATION FOR SEQ ID NO: 14:

(i) SEQUENCE CHARACTERISTICS:
        (A) LENGTH: 900 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Arg Val Gln Pro Gln Gln Ser Pro Ala Ala Ala Pro Gly Gly Thr Asp
1               5                   10                  15

Glu Lys Pro Ser Gly Lys Glu Arg Arg Asp Ala Gly Asp Lys Asp Lys
            20                  25                  30

Glu Gln Glu Leu Ser Glu Glu Asp Lys Gln Leu Gln Asp Glu Leu Glu
        35                  40                  45

Met Leu Val Glu Arg Leu Gly Glu Lys Asp Thr Ser Leu Tyr Arg Pro
50                  55                  60

Ala Leu Glu Glu Leu Arg Arg Gln Ile Arg Ser Ser Thr Thr Ser Met
65                  70                  75                  80

Thr Ser Val Pro Lys Pro Leu Lys Phe Leu Arg Pro His Tyr Gly Lys
                85                  90                  95

Leu Lys Glu Ile Tyr Glu Asn Met Ala Pro Gly Glu Asn Lys Arg Phe
            100                 105                 110

Ala Ala Asp Ile Ile Ser Val Leu Ala Met Thr Met Ser Gly Glu Arg
        115                 120                 125

Glu Cys Leu Lys Tyr Arg Leu Val Gly Ser Gln Glu Glu Leu Ala Ser
    130                 135                 140

Trp Gly His Glu Tyr Val Arg His Leu Ala Gly Glu Val Ala Lys Glu

```
                145                 150                 155                 160
Trp Gln Glu Leu Asp Asp Ala Glu Lys Val Gln Arg Glu Pro Leu Leu
                    165                 170                 175

Thr Leu Val Lys Glu Ile Val Pro Tyr Asn Met Ala His Asn Ala Glu
                180                 185                 190

His Glu Ala Cys Asp Leu Leu Met Glu Ile Glu Gln Val Asp Met Leu
            195                 200                 205

Glu Lys Asp Ile Asp Glu Asn Ala Tyr Ala Lys Val Cys Leu Tyr Leu
        210                 215                 220

Thr Ser Cys Val Asn Tyr Val Pro Glu Pro Glu Asn Ser Ala Leu Leu
225                 230                 235                 240

Arg Cys Ala Leu Gly Val Phe Arg Lys Phe Thr Arg Phe Pro Glu Ala
                245                 250                 255

Leu Arg Leu Ala Leu Met Leu Asn Asp Met Glu Leu Val Glu Asp Ile
                260                 265                 270

Phe Thr Ser Cys Lys Asp Val Val Gln Lys Gln Met Ala Phe Met
            275                 280                 285

Leu Gly Arg His Gly Val Phe Leu Glu Leu Ser Glu Asp Val Glu Glu
        290                 295                 300

Tyr Glu Asp Leu Thr Glu Ile Met Ser Asn Val Gln Leu Asn Ser Asn
305                 310                 315                 320

Phe Leu Ala Leu Ala Arg Glu Leu Asp Ile Met Glu Pro Lys Val Pro
                325                 330                 335

Asp Asp Ile Tyr Lys Thr His Leu Glu Asn Asn Arg Phe Gly Gly Ser
                340                 345                 350

Gly Ser Gln Val Asp Ser Ala Arg Met Asn Leu Ala Ser Ser Phe Val
            355                 360                 365

Asn Gly Phe Val Asn Ala Ala Phe Gly Gln Asp Lys Leu Leu Thr Asp
370                 375                 380

Asp Gly Asn Lys Trp Leu Tyr Lys Asn Lys Asp His Gly Met Leu Ser
385                 390                 395                 400

Ala Ala Ala Ser Leu Gly Met Ile Leu Leu Trp Asp Val Asp Gly Gly
                405                 410                 415

Leu Thr Gln Ile Asp Lys Tyr Leu Tyr Ser Ser Glu Asp Tyr Ile Lys
                420                 425                 430

Ser Gly Ala Leu Leu Ala Cys Gly Ile Val Asn Ser Gly Val Arg Asn
            435                 440                 445

Glu Cys Asp Pro Ala Leu Ala Leu Leu Ser Asp Tyr Val Leu His Asn
        450                 455                 460

Ser Asn Thr Met Arg Leu Gly Ser Ile Phe Gly Leu Gly Leu Ala Tyr
465                 470                 475                 480

Ala Gly Ser Asn Arg Glu Asp Val Leu Thr Leu Leu Pro Val Met
                485                 490                 495

Gly Asp Ser Lys Ser Ser Met Glu Val Ala Gly Val Thr Ala Leu Ala
            500                 505                 510

Cys Gly Met Ile Ala Val Gly Ser Cys Asn Gly Asp Val Thr Ser Thr
        515                 520                 525

Ile Leu Gln Thr Ile Met Glu Lys Ser Glu Thr Glu Leu Lys Asp Thr
    530                 535                 540

Tyr Ala Arg Trp Leu Pro Leu Gly Leu Gly Leu Asn His Leu Gly Lys
545                 550                 555                 560

Gly Glu Ala Ile Glu Ala Ile Leu Ala Ala Leu Glu Val Val Ser Glu
                565                 570                 575
```

```
Pro Phe Arg Ser Phe Ala Asn Thr Leu Val Asp Val Cys Ala Tyr Ala
            580                 585                 590

Gly Ser Gly Asn Val Leu Lys Val Gln Gln Leu Leu His Ile Cys Ser
            595                 600                 605

Glu His Phe Asp Ser Lys Glu Lys Glu Asp Lys Asp Lys Lys Glu
            610                 615                 620

Lys Lys Asp Lys Asp Lys Lys Glu Ala Pro Ala Asp Met Gly Ala His
625                 630                 635                 640

Gln Gly Val Ala Val Leu Gly Ile Ala Leu Ile Ala Met Gly Glu Glu
                645                 650                 655

Ile Gly Ala Glu Met Ala Leu Arg Thr Phe Gly His Leu Leu Arg Tyr
            660                 665                 670

Gly Glu Pro Thr Leu Arg Arg Ala Val Pro Leu Ala Leu Ala Leu Ile
            675                 680                 685

Ser Val Ser Asn Pro Arg Leu Asn Ile Leu Asp Thr Leu Ser Lys Phe
            690                 695                 700

Ser His Asp Ala Asp Pro Glu Val Ser Tyr Asn Ser Ile Phe Ala Met
705                 710                 715                 720

Gly Met Val Gly Ser Gly Thr Asn Asn Ala Arg Leu Ala Ala Met Leu
                725                 730                 735

Arg Gln Leu Ala Gln Tyr His Ala Lys Asp Pro Asn Asn Leu Phe Met
                740                 745                 750

Val Arg Leu Ala Gln Gly Leu Thr His Leu Gly Lys Gly Thr Leu Thr
            755                 760                 765

Leu Cys Pro Tyr His Ser Asp Arg Gln Leu Met Ser Gln Val Ala Val
            770                 775                 780

Ala Gly Leu Leu Thr Val Leu Val Ser Phe Leu Asp Val Arg Asn Ile
785                 790                 795                 800

Ile Leu Gly Lys Ser His Tyr Val Leu Tyr Gly Leu Val Ala Ala Met
                805                 810                 815

Gln Pro Arg Met Leu Val Thr Phe Asp Glu Glu Leu Arg Pro Leu Pro
            820                 825                 830

Val Ser Val Arg Val Gly Gln Ala Val Asp Val Val Gly Gln Ala Gly
            835                 840                 845

Lys Pro Lys Thr Ile Thr Gly Phe Gln Thr His Thr Thr Pro Val Leu
            850                 855                 860

Leu Ala His Gly Glu Arg Ala Glu Leu Ala Thr Glu Phe Leu Pro
865                 870                 875                 880

Val Thr Pro Ile Leu Glu Gly Phe Val Ile Phe Gly Arg Thr Pro Ile
                885                 890                 895

Met Ile Ser Lys
            900

(2) INFORMATION FOR SEQ ID NO: 15:

(i) SEQUENCE CHARACTERISTICS:
        (A) LENGTH: 995 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Lys Lys Met Val Asp Glu Ser Asp Lys Lys Gln Gln Thr Ile Asp Glu
1               5                   10                  15
```

```
Gln Ser Gln Ile Ser Pro Glu Lys Gln Thr Pro Asn Lys Lys Asp Lys
                 20                  25                  30
Lys Lys Glu Glu Glu Gln Leu Ser Glu Asp Ala Lys Leu Lys
             35                  40                  45
Thr Asp Leu Glu Leu Leu Val Glu Arg Leu Lys Glu Asp Ser Ser
 50                  55                  60
Leu Tyr Glu Ala Ser Leu Asn Ala Leu Lys Glu Ser Ile Lys Asn Ser
 65                  70                  75                  80
Thr Ser Ser Met Thr Ala Val Pro Lys Pro Leu Lys Phe Leu Arg Pro
                 85                  90                  95
Thr Tyr Pro Asp Leu Cys Ser Ile Tyr Asp Lys Trp Thr Asp Pro Asn
                100                 105                 110
Leu Lys Ser Ser Leu Ala Asp Val Leu Ser Ile Leu Ala Met Thr Tyr
                115                 120                 125
Ser Glu Asn Gly Lys His Asp Ser Leu Arg Tyr Arg Leu Leu Ser Asp
                130                 135                 140
Val Ser Asp Phe Glu Gly Trp Gly His Glu Tyr Ile Arg His Leu Ala
145                 150                 155                 160
Leu Glu Ile Gly Glu Val Tyr Asn Asp Gln Val Glu Lys Asp Ala Glu
                165                 170                 175
Asp Glu Thr Ser Ser Asp Gly Ser Lys Ser Asp Gly Ser Ala Ala Thr
                180                 185                 190
Ser Gly Phe Glu Phe Ser Lys Glu Asp Thr Leu Arg Leu Cys Leu Asp
                195                 200                 205
Ile Val Pro Tyr Phe Leu Lys His Asn Gly Glu Glu Asp Ala Val Asp
                210                 215                 220
Leu Leu Leu Glu Ile Glu Ser Ile Asp Lys Leu Pro Gln Phe Val Asp
225                 230                 235                 240
Glu Asn Thr Phe Gln Arg Val Cys Gln Tyr Met Val Ala Cys Val Pro
                245                 250                 255
Leu Leu Pro Pro Pro Glu Asp Val Ala Phe Leu Lys Thr Ala Tyr Ser
                260                 265                 270
Ile Tyr Leu Ser Gln Asn Glu Leu Thr Asp Ala Ile Ala Leu Ala Val
                275                 280                 285
Arg Leu Gly Glu Glu Asp Met Ile Arg Ser Val Phe Asp Ala Thr Ser
290                 295                 300
Asp Pro Val Met His Lys Gln Leu Ala Tyr Ile Leu Ala Ala Gln Lys
305                 310                 315                 320
Thr Ser Phe Glu Tyr Glu Gly Val Gln Asp Ile Ile Gly Asn Gly Lys
                325                 330                 335
Leu Ser Glu His Phe Leu Tyr Leu Ala Lys Glu Leu Asn Leu Thr Gly
                340                 345                 350
Pro Lys Val Pro Glu Asp Ile Tyr Lys Ser His Leu Asp Asn Ser Lys
                355                 360                 365
Ser Val Phe Ser Ser Ala Gly Leu Asp Ser Ala Gln Gln Asn Leu Ala
                370                 375                 380
Ser Ser Phe Val Asn Gly Phe Leu Asn Leu Gly Tyr Cys Asn Asp Lys
385                 390                 395                 400
Leu Ile Val Asp Asn Asp Asn Trp Val Tyr Lys Thr Lys Gly Asp Gly
                405                 410                 415
Met Thr Ser Ala Val Ala Ser Ile Gly Ser Ile Tyr Gln Trp Asn Leu
                420                 425                 430
```

-continued

```
Asp Gly Leu Gln Gln Leu Asp Lys Tyr Leu Tyr Val Asp Glu Pro Glu
        435                 440                 445

Val Lys Ala Gly Ala Leu Leu Gly Ile Gly Ile Ser Ala Ser Gly Val
    450                 455                 460

His Asp Gly Glu Val Glu Pro Ala Leu Leu Leu Gln Asp Tyr Val
465                 470                 475                 480

Thr Asn Pro Asp Thr Lys Ile Ser Ser Ala Ala Ile Leu Gly Leu Gly
                485                 490                 495

Ile Ala Phe Ala Gly Ser Lys Asn Asp Glu Val Leu Gly Leu Leu Leu
            500                 505                 510

Pro Ile Ala Ala Ser Thr Asp Leu Pro Ile Glu Thr Ala Ala Met Ala
        515                 520                 525

Ser Leu Ala Leu Ala His Val Phe Val Gly Thr Cys Asn Gly Asp Ile
    530                 535                 540

Thr Thr Ser Ile Met Asp Asn Phe Leu Glu Arg Thr Ala Ile Glu Leu
545                 550                 555                 560

Lys Thr Asp Trp Val Arg Phe Leu Ala Leu Ala Leu Gly Ile Leu Tyr
                565                 570                 575

Met Gly Gln Gly Glu Gln Val Asp Asp Val Leu Glu Thr Ile Ser Ala
            580                 585                 590

Ile Glu His Pro Met Thr Ser Ala Ile Glu Val Leu Val Gly Ser Cys
        595                 600                 605

Ala Tyr Thr Gly Thr Gly Asp Val Leu Leu Ile Gln Asp Leu Leu His
    610                 615                 620

Arg Leu Thr Pro Lys Asn Val Lys Gly Glu Glu Asp Ala Asp Glu Glu
625                 630                 635                 640

Glu Thr Ala Glu Gly Gln Thr Asn Ser Ile Ser Asp Phe Leu Gly Glu
                645                 650                 655

Gln Val Asn Glu Pro Thr Lys Asn Glu Glu Ala Glu Ile Glu Val Asp
            660                 665                 670

Glu Met Glu Val Asp Ala Glu Gly Glu Glu Val Glu Val Lys Ala Glu
        675                 680                 685

Ile Thr Glu Lys Lys Asn Gly Glu Ser Leu Glu Gly Glu Glu Ile Lys
    690                 695                 700

Ser Glu Glu Lys Lys Gly Lys Ser Ser Asp Lys Asp Ala Thr Thr Asp
705                 710                 715                 720

Gly Lys Asn Asp Asp Glu Glu Glu Lys Glu Ala Gly Ile Val Asp
                725                 730                 735

Glu Leu Ala Tyr Ala Val Leu Gly Ile Ala Leu Ile Ala Leu Gly Glu
            740                 745                 750

Asp Ile Gly Lys Glu Met Ser Leu Arg His Phe Gly His Leu Met His
        755                 760                 765

Tyr Gly Asn Glu His Ile Arg Arg Met Val Pro Leu Ala Met Gly Ile
    770                 775                 780

Val Ser Val Ser Asp Pro Gln Met Lys Val Phe Asp Thr Leu Thr Arg
785                 790                 795                 800

Phe Ser His Asp Ala Asp Leu Glu Val Ser Met Asn Ser Ile Phe Ala
                805                 810                 815

Met Gly Leu Cys Gly Ala Gly Thr Asn Asn Ala Arg Leu Ala Gln Leu
            820                 825                 830

Leu Arg Gln Leu Ala Ser Tyr Tyr Ser Arg Glu Gln Asp Ala Leu Phe
        835                 840                 845

Ile Thr Arg Leu Ala Gln Gly Leu Leu His Leu Gly Lys Gly Thr Met
```

-continued

```
                 850                 855                 860
Thr Met Asp Val Phe Asn Asp Ala His Val Leu Asn Lys Val Thr Leu
865                 870                 875                 880

Ala Ser Ile Leu Thr Thr Ala Val Gly Leu Val Ser Pro Ser Phe Met
                885                 890                 895

Leu Lys His His Gln Leu Phe Tyr Met Leu Asn Ala Gly Ile Arg Pro
                900                 905                 910

Lys Phe Ile Leu Ala Leu Asn Asp Glu Gly Glu Pro Ile Lys Val Asn
                915                 920                 925

Val Arg Val Gly Gln Ala Val Glu Thr Val Gly Gln Ala Gly Arg Pro
            930                 935                 940

Lys Lys Ile Thr Gly Trp Ile Thr Gln Ser Thr Pro Val Leu Leu Asn
945                 950                 955                 960

His Gly Glu Arg Ala Glu Leu Glu Thr Asp Glu Tyr Ile Ser Tyr Thr
                965                 970                 975

Ser His Ile Glu Gly Val Val Ile Leu Lys Lys Asn Pro Asp Tyr Arg
                980                 985                 990

Glu Glu Glu
        995
```

(2) INFORMATION FOR SEQ ID NO: 16:

(i) SEQUENCE CHARACTERISTICS:
        (A) LENGTH: 945 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

```
Met Ser Leu Thr Thr Ala Ala Pro Leu Leu Ala Leu Leu Arg Glu Asn
1               5                   10                  15

Gln Asp Ser Val Lys Thr Tyr Ala Leu Glu Ser Ile Asn Asn Val Val
            20                  25                  30

Asp Gln Leu Trp Ser Glu Ile Ser Asn Glu Leu Pro Asp Ile Glu Ala
            35                  40                  45

Leu Tyr Asp Asp Asp Thr Phe Ser Asp Arg Glu Met Ala Ala Leu Ile
50                  55                  60

Ala Ser Lys Val Tyr Tyr Asn Leu Gly Glu Tyr Glu Ser Ala Val Lys
65                  70                  75                  80

Tyr Ala Leu Ala Ala Lys Asp Arg Phe Asp Ile Asp Glu Lys Ser Gln
                85                  90                  95

Phe Val Glu Thr Ile Val Ser Lys Ser Ile Glu Met Tyr Val Gln Glu
                100                 105                 110

Ala Ser Lys Gln Tyr Thr Lys Asp Glu Gln Phe Tyr Thr Lys Asp Ile
                115                 120                 125

Ile Asp Pro Lys Leu Thr Ser Ile Phe Glu Arg Met Ile Glu Lys Cys
            130                 135                 140

Leu Lys Ala Ser Glu Leu Lys Leu Ala Leu Gly Ile Ala Leu Glu Gly
145                 150                 155                 160

Tyr Arg Leu Asp Ile Ile Glu Ser Ala Leu Lys Ser Lys Leu Asp Gln
                165                 170                 175

Asp Ser Thr Ser Glu Asn Val Lys Ile Ile Asn Tyr Leu Leu Thr Leu
                180                 185                 190

Ala Ile Thr Thr Val Thr Asn Ser Lys Phe Arg Ser Ser Ile Leu Arg
```

-continued

```
                195                 200                 205
Lys Ser Phe Asp Phe Leu Met Asn Met Pro Asn Cys Asp Tyr Leu Thr
            210                 215                 220
Leu Asn Lys Val Val Asn Leu Asn Asp Ala Gly Leu Ala Leu Gln
225                 230                 235                 240
Leu Phe Lys Lys Leu Lys Glu Glu Asn Asp Glu Gly Leu Ser Ala Gln
                245                 250                 255
Ile Ala Phe Asp Leu Val Ser Ala Ser Gln Gln Leu Leu Glu Ile
            260                 265                 270
Leu Val Thr Glu Leu Thr Ala Gln Gly Tyr Asp Pro Ala Leu Leu Asn
            275                 280                 285
Ile Leu Ser Gly Leu Pro Thr Cys Asp Tyr Tyr Asn Thr Phe Leu Leu
            290                 295                 300
Asn Asn Lys Asn Ile Asp Ile Gly Leu Leu Asn Lys Ser Lys Ser Ser
305                 310                 315                 320
Leu Asp Gly Lys Phe Ser Leu Phe His Thr Ala Val Arg Leu Ala Asn
                325                 330                 335
Gly Phe Met His Ala Gly Thr Thr Asp Asn Ser Phe Ile Lys Ala Asn
            340                 345                 350
Leu Pro Trp Leu Gly Lys Ala Gln Asn Trp Ala Lys Phe Thr Ala Thr
            355                 360                 365
Ala Ser Leu Gly Val Ile His Lys Gly Asn Leu Leu Glu Gly Lys Lys
            370                 375                 380
Val Met Ala Pro Tyr Leu Pro Gly Ser Arg Ala Ser Ser Arg Phe Ile
385                 390                 395                 400
Lys Gly Gly Ser Leu Tyr Gly Leu Gly Leu Ile Tyr Ala Gly Phe Gly
                405                 410                 415
Arg Asp Thr Thr Asp Tyr Leu Lys Asn Ile Ile Val Glu Asn Ser Gly
            420                 425                 430
Thr Ser Gly Asp Glu Asp Val Asp Val Leu Leu His Gly Ala Ser Leu
            435                 440                 445
Gly Ile Gly Leu Ala Ala Met Gly Ser Ala Asn Ile Glu Val Tyr Glu
            450                 455                 460
Ala Leu Lys Glu Val Leu Tyr Asn Asp Ser Ala Thr Ser Gly Glu Ala
465                 470                 475                 480
Ala Ala Leu Gly Met Gly Leu Cys Met Leu Gly Thr Gly Lys Pro Glu
                485                 490                 495
Ala Ile His Asp Met Phe Thr Tyr Ser Gln Glu Thr Gln His Gly Asn
            500                 505                 510
Ile Thr Arg Gly Leu Ala Val Gly Leu Ala Leu Ile Asn Tyr Gly Arg
            515                 520                 525
Gln Glu Leu Ala Asp Asp Leu Ile Thr Lys Met Leu Ala Ser Asp Glu
            530                 535                 540
Ser Leu Leu Arg Tyr Gly Gly Ala Phe Thr Ile Ala Leu Ala Tyr Ala
545                 550                 555                 560
Gly Thr Gly Asn Asn Ser Ala Val Lys Arg Leu Leu His Val Ala Val
                565                 570                 575
Ser Asp Ser Asn Asp Asp Val Arg Arg Ala Val Ile Ala Leu Gly
            580                 585                 590
Phe Val Leu Leu Arg Asp Tyr Thr Thr Val Pro Arg Ile Val Gln Leu
            595                 600                 605
Leu Ser Lys Ser His Asn Ala His Val Arg Cys Gly Thr Ala Phe Ala
            610                 615                 620
```

```
Leu Gly Ile Ala Cys Ala Gly Lys Gly Leu Gln Ser Ala Ile Asp Val
625                 630                 635                 640

Leu Asp Pro Leu Thr Lys Asp Pro Val Asp Phe Val Arg Gln Ala Ala
            645                 650                 655

Met Ile Ala Leu Ser Met Ile Leu Ile Gln Gln Thr Glu Lys Leu Asn
            660                 665                 670

Pro Gln Val Ala Asp Ile Asn Lys Asn Phe Leu Ser Val Ile Thr Asn
            675                 680                 685

Lys His Gln Glu Gly Leu Ala Lys Phe Gly Ala Cys Val Ala Gln Gly
690                 695                 700

Ile Met Asn Ala Gly Gly Arg Asn Val Thr Ile Gln Leu Glu Asn Ala
705                 710                 715                 720

Asp Thr Gly Thr Leu Asp Thr Lys Ser Val Val Gly Leu Val Met Phe
            725                 730                 735

Ser Gln Phe Trp Tyr Trp Phe Pro Leu Ala His Phe Leu Ser Leu Ser
            740                 745                 750

Phe Thr Pro Thr Thr Val Ile Gly Ile Arg Gly Ser Asp Gln Ala Ile
            755                 760                 765

Pro Lys Phe Gln Met Asn Cys Tyr Ala Lys Glu Asp Ala Phe Ser Tyr
770                 775                 780

Pro Arg Met Tyr Glu Glu Ala Ser Gly Lys Glu Val Glu Lys Val Ala
785                 790                 795                 800

Thr Ala Val Leu Ser Thr Thr Ala Arg Ala Lys Ala Arg Ala Lys Lys
            805                 810                 815

Thr Lys Lys Glu Lys Gly Pro Asn Glu Glu Lys Lys Lys Glu His
            820                 825                 830

Glu Glu Lys Glu Lys Glu Arg Glu Thr Asn Lys Lys Gly Ile Lys Glu
            835                 840                 845

Thr Lys Glu Asn Asp Glu Glu Phe Tyr Lys Asn Lys Tyr Ser Ser Lys
850                 855                 860

Pro Tyr Lys Val Asp Asn Met Thr Arg Ile Leu Pro Gln Gln Ser Arg
865                 870                 875                 880

Tyr Ile Ser Phe Ile Lys Asp Asp Arg Phe Val Pro Val Arg Lys Phe
            885                 890                 895

Lys Gly Asn Asn Gly Val Val Val Leu Arg Asp Arg Glu Pro Lys Glu
            900                 905                 910

Pro Val Ala Leu Ile Glu Thr Val Arg Gln Met Lys Asp Val Asn Ala
            915                 920                 925

Pro Leu Pro Thr Pro Phe Lys Val Asp Asp Asn Val Asp Phe Pro Ser
    930                 935                 940

Ala
945

(2) INFORMATION FOR SEQ ID NO: 17:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Trp Xaa Ile Arg Ser Asp Glu Arg Val Leu Gln Tyr Gly Glu Gln Asn
1               5                   10                  15
```

```
Ile Arg Arg Ala Val Pro Leu Ala Leu Gly Leu Leu Cys Ile Ser Asn
             20                  25                  30

Pro Lys Val Thr Val Met Asp Thr Leu Ser Arg Leu Ser His Asp Arg
             35                  40                  45

Phe Arg Ser Cys Asn Gly Ser Asn Tyr Leu Pro Trp Ile Asp Arg Arg
             50                  55                  60

Trp Asn Gln Gln Cys Lys Asp Ser Trp His Ala Lys Ser Leu Gln Leu
 65                  70                  75                  80

Leu Leu Gln Gly Cys Pro Xaa Phe Phe Ser Val Cys Ala Ser Leu Lys
                 85                  90                  95

Gly Phe Xaa His Met Gly Lys Gly Leu Leu Thr Leu Asn Pro Phe His
                100                 105                 110

Ser Glu Arg Ala Xaa Phe Leu Xaa Xaa Asn Pro Asp Phe Pro Trp Val
            115                 120                 125

Gly Xaa Asn Phe Leu Gln Xaa Xaa Xaa Phe Xaa Ile Glu Thr
        130                 135                 140

(2) INFORMATION FOR SEQ ID NO: 18:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 18:

MRMTTVDMKG SKNVSVRVGV DVVAAGKKTT GTHTTVAHGR AANDYSVTHG VKKNDYVVVS      60

TKK                                                                   63

(2) INFORMATION FOR SEQ ID NO: 19:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

ATCAGTGTCA CTACGGATAG TGATGACACT CACAGGAGGG CTGGGGGTAT CTGGAATGAT      60

GATTGGCTGA TGCTGGTCTT GGACAGGAAC TAGGGAATTA TAAGAAGATG TGGTACGAAG     120

AGGACTACTC CCANCCAGAG AATAAACTTG AGAAGGCAGG ACTTCCAGAG AGGATTTGGA     180

TGAAACTGGA GCAGACTGCT TATTCTACTT TGAAGGGAGG GAACTAGACT GTTGTTGTCT     240

GACAACATGG GCAACACCAA CATTCAGAGG CTGAGCAGTN GCCAAGGNCA CATGGTTGGT     300

CAGCAAAGAT GGCTGCTGCA TAATAGTGCT GTACTGGTCG NCATGAGAGT GGGCATTCCC     360

CAGTCAGCTA GCTGGTGGGC TGCTCCCCAT                                     390

(2) INFORMATION FOR SEQ ID NO: 20:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 20:

```
CCTCTCAGTT ATCTCTGTTG GAGTAGTCCT CTTCGTACCA CATCTTCTTA TAATTCCCTA      60

GTTCCTGTCC AAGACCAGCA TCAGCCAATC ATCATTCCAG ATACCCCAG CCCTCCTGTG       120

AGTGTCATCA CTATCCGTAG TGACACTGAT GAAGAAGAGG ACAACAAATA CAAGCCCAAT     180

AGCTCGAGCC TGAAGGCGAG GTCTAATGTC ATCAGTTATG TCACTGTCAA TGATTCTCCA     240

GACTCTGACT CCTCCCTGAG CAGCCCACAT TCCACAGCCA CTCTGAGTGC TCTGCGGGGC     300

AACAGTGGGA CCCTTCTGGA GGGACCTGGC AGACCTGCAG CAGATGGCAT TGGCACCCGT     360

ACTATCATTG TACCTGAGCG GCCGC                                           385
```

(2) INFORMATION FOR SEQ ID NO: 21:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

```
GGGAGCCTGT GCACCCCGAT GTCACCATGA AGCCACTGCC CTTCTATGAA GTCTATGGGG     60

AGCTCATCCG ACCCACCACC CTTGCGTCCA CCTCCAGCCA GAGGTTCGAG GAAGCCCACT     120

TCACCTTCGC GCTCACTCCC CAGCAGCTGC AGCAGATTCT CACGTCCAGG GAGGTTATGC     180

CAGGAGCCAA GTGTGATTAC ACCATACAAG TGCAGCTCAG ATTCTGTCTC TGTGAGACCA     240

GCTGCCCTCA GGAGGACTAT TTCCCCCCTA ACCTCTTTGT TAAGGTTAAT GGGAAACTCT     300

GCCCCCTGCC GGGTTACCTC CCTCCAACCC AAGAATGGAG CTGAGCCCAA GAGGCCCAGC     360

CGTCCGATCA ACATCACACC CTTGGCTCGA CTCTCAGCCA CTGTCCCCAA CACCATCGTA     420

GTTAATTGGG TCATCTTGAA GTTT                                            444
```

(2) INFORMATION FOR SEQ ID NO: 22:

(i) SEQUENCE CHARACTERISTICS:
        (A) LENGTH: 888 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

```
TCCAACACCA TCGTAGATAA ATTGGTCATC TGAGTTTGGA CCGGAATTAC TCCTTGTCCG     60

TGTACCCTGG TGAGGCAATT GACTGCAGGG ACCCTTCTAC ACAAACTCAG AGCCAAGGGG     120

ATCCGGAATC CAGACCATTC CCGGGCACTG ATCAAGGAGA AACTGACTGC TGACCCCGAC     180

AGTGAAGTGG CTACTACAAG TCTCCGGGTG TCACTCATGT GCCCGCTAGG AAGATGCGC     240

CTGACTGTCC CGTGTCGTGC CCTCACCTGT GCCCATCTGC AGAGTTTCGA TGCTGCCCTT     300

TATCTACAGA TGAATGAGAA GAAGCCGACA TGGACGTGTC CTGTGCGTGA CAAGAAGGCT     360

CCCTATGAGT CGCTGATTAT TGATGGTTTA TTCATGGAAA TTCTTAATTC CTGTTCGGAT     420

TGTGATGAGA TCCAGTTCAT GGAAGATGGA TCCTGGTGTC CGATGAAACC CAAGAAGGAG     480

GCATCAGAGG TTTGCCCCCC GCCAGGGTAT GGGCTGGATG GTCTCCAGTA CAGCGCAGTC     540

CAGGAGGGAA TTCAGCCAGA GAGTAAGAAG AGGGTCGAAG TCATTGACTT GACCATCGAA     600
```

```
AGCTCATCAG ATGAGGAGGA TTTGCCCCCC ACCAAGAAGC ACTGCCCTGT CACCTCAGCG      660

GTCATTCCAG CCCTTCCTGG AAGCAAAGGA GCCCTGACCT CTGGTCACCA GCCATCCTCG      720

GTGCTGCGGA GCCCTGCAAT GGGCACACTG GGCAGTGACT TCCTGTCTAG TCTCCCGCTA      780

CATGAGTACC CACCTGCCTT CCCACTGGGG GTTGACATCC AAGGTTTAGA TTTTATTTTC      840

TTTTCTTCAG ACTGAGAGTC AGAATTACGG GCCTTCAGTT ATCATTCG                  888

(2) INFORMATION FOR SEQ ID NO: 23:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

CCACTTCCTG GCCCACTGCC CCAAACTGG GGACTCTCAC CGCAAGCTCC AACTCCAGCG       60

CCCCCTCCTG GTCGTGTCAG CAGCATTGTG GCTCCTGGGA GCTCCTTGAG GGAAGGGCAT     120

GGAGGACCCC TGCCTTCAGG TCCCTCTTTG ACTGGCTGTC GGTCAGACGT CATTTCCTTG     180

GACTGAGCTT TTTGGATTAT GAAATCAATC TCCATTGGCC CCAGCACTGA GCAGATCACG     240

TTGTGGGTTC CGAACCCCTG GCTGCTCTGA TCCCTCAGGG GTCATTGGCC AAAGGCCAGG     300

CCAGAGCTTC ATGGATACCT GCTTTTGGCC TTATCGCTGC CTAACAGGCC AGTACTCACA     360

GGGTTAACAT TTAACCTTTT TATGGTGGCC CG                                   392

(2) INFORMATION FOR SEQ ID NO: 24:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

AATTCGGCAC GAGGTTGTGC TGTGGGGAAG GGAGAAGGAT TTGTAAACCC CGGAGCGAGG      60

TTCTGCTTAC CCGAGGCCGC TGCTGTGCGG AGACCCCCGG GTGAAGCCAC CGTCATCATG     120

TCTGACCAGG AGGCAAAACC TTCCAACTGA GGACTTGGGG GATAAGAAGG AAGGTGAATA     180

TATTAAACTC AAAGTCATTG ACAGGATAG CAGTGAGATT CACTTCAAAG TGAAAATGAC      240

AACACATCTC AAGAAACTCA AAGAATCATA CTGTCAAAGA CAGGGTGTTC CAATGAATTC     300

ACTCAGGTTT CTCTTTGAGG GTCAGAGAAT TGCTGATAAT CATACTCCAA AGAACTGGG     360

AATGGAGAAG AAAGATTGTG ATTTGAAGTT TTATCAGGAA CAAACGGGGG GTCATTCAAC    420

AGCTT                                                                 425

(2) INFORMATION FOR SEQ ID NO:25:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:
```

-continued

```
ACCTTCAAGA TCCGCATGGA GCCTGACGAG ACGGTGAAGG TGCTAAAGGA GAAGATAGAA    60

GCTGAGAAGG GTCGTGATGC CTTCCCCGTG GCTGGACAGA AACTCATCTA TGCCGGCAAG   120

ATCTTGAGTG ACGATGTCCC TATCAGGGAC TATCGCATCG ATGAGAAGAA CTTTGTGGTC   180

GTCATGGTGA CCAAGACCAA AGCCGGCCAG GGTACCTCAG CACCCCCAGA GGCCTCACCC   240

ACAGCTGCCC CAGAGTCCTC TACATCCTTC CCGCCTGCCC CCACCTCAGG AATGTCCCAT   300

CCCCCACCTG CCGCCAGAGA GGACAAGAGC CCATCAGAGG AATCCACCCC CACCCCAGAA   360

CAGGAACCGT GTCTCTGATA AAGGTTTGGA AGTGAATTAA AGTTTTAAAA              410
```

(2) INFORMATION FOR SEQ ID NO:26:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Thr Phe Lys Ile Arg Met Glu Pro Asp Glu Thr Val Lys Val Leu Lys
1               5                  10                  15

Glu Lys Ile Glu Ala Glu Lys Gly Arg Asp Ala Phe Pro Val Ala Gly
            20                  25                  30

Gln Lys Leu Ile Tyr Ala Gly Lys Ile Leu Ser Asp Asp Val Pro Ile
        35                  40                  45

Arg Asp Tyr Arg Ile Asp Glu Lys Asn Phe Val Val Met Val Thr
    50                  55                  60

Lys Thr Lys Ala Gly Gln Gly Thr Ser Ala Pro Pro Glu Ala Ser Pro
65                  70                  75                  80

Thr Ala Ala Pro Glu Ser Ser Thr Ser Phe Pro Pro Ala Pro Thr Ser
                85                  90                  95

Gly Met Ser His Pro Pro Pro Ala Ala Arg Glu Asp Lys Ser Pro Ser
            100                 105                 110

Glu Glu Ser Thr Pro Thr Pro Glu Gln Glu Pro Cys Leu Glx
        115                 120                 125
```

(2) INFORMATION FOR SEQ ID NO:27:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
GACACCTCTG TCCTGGCGGG TGTGTACGGG CCGGCCGAGG TGAAGGTCAG CAAAGAGATT    60

TTCAACAAGG CCACACTCGA AGTGATCCTG AGGCCGAAGA TTGGGCTGCC TGGTGTTGCA   120

GAGAAGAGCC GGGAGCGGCT GATCAGGAAC ACGTGCGAGG CGGTGGTGCT GGGCACGTTG   180

CACCCCCGCA CCTCCATCAC CGTGGTGCTG CAGGTTGTCA GCGATGCCGG CTCTCTCCTG   240

GCCTGTTGTC TGAATGCCGC CTGCATGGCA TTGGTGGATG CAGGTGTGCC CATGCGGGCT   300

CTCTTCTGTG GGGTCGCCTG CGCCCTGGAC TCTGATGGGA CCCTCGTGCT GGATCCTACA   360

TCCAAGCAAG AAAAGGAGGC CCGGGCAGTC CTGACCTTTC TCCTGGACAG CGTGGAACGG   420

AAGCTGCTGA TGTCCAGCAC CAAGGGGCTC TACTCAGACA CTGAGCTCCA GCAGTGCCTG   480
```

```
GCTGCGGCCC AGGCCGCTTC GCAACACGTC TTCCGTTTCT ACCGGGAATC GCTGCAGAGG    540

CGTTACTCCA AGAGCTGAGG CAAGCTGGGG CAAGGGGCCG CTCCCATTGC CTCCACCCAC    600

TCACCCCCTA CAGCCTGAAG CAAACCAGCA GCCCAGCCTT GCCTCTCTGA CCCATGGGCT    660

CCTTGAGCCT GCAGCTCTGT AAGCACAGGG CTCCTGTGGG GAGGCCTTGG CCTGTGACAG    720

CCCCCAGGCC TGGGGGCACA GATCCCCCCA GCAAGGATAA CATTCAAAGG AGCTCACATT    780

TATGGAATGG ATGAATCAAT AAATTAATTC ACTTTAACAA AAAAAAAAAA AAA           833
```

(2) INFORMATION FOR SEQ ID NO:28:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Met Glu Glu Met His Thr Asp Ala Lys Ile Arg Ala Glu Asn Gly
 1               5                  10                  15

Thr Gly Ser Ser Pro Arg Gly Pro Gly Cys Ser Leu Arg His Phe Ala
                20                  25                  30

Cys Glu Gln Asn Leu Leu Ser Arg Pro Asp Gly Ser Ala Ser Phe Leu
                35                  40                  45

Gln Gly Asp Thr Ser Val Leu Ala Gly Val Tyr Gly Pro Ala Glu Val
            50                  55                  60

Lys Val Ser Lys Glu Ile Phe Asn Lys Ala Thr Leu Glu Val Ile Leu
65                  70                  75                  80

Arg Pro Lys Ile Gly Leu Pro Gly Val Ala Glu Lys Ser Arg Glu Arg
                    85                  90                  95

Leu Ile Arg Asn Thr Cys Glu Ala Val Val Leu Gly Thr Leu His Pro
                100                 105                 110

Arg Thr Ser Ile Thr Val Val Leu Gln Val Val Ser Asp Ala Gly Ser
            115                 120                 125

Leu Leu Ala Cys Cys Leu Asn Ala Ala Cys Met Ala Leu Val Asp Ala
        130                 135                 140

Gly Val Pro Met Arg Ala Leu Phe Cys Gly Val Ala Cys Ala Leu Asp
145                 150                 155                 160

Ser Asp Gly Thr Leu Val Leu Asp Pro Thr Ser Lys Gln Glu Lys Glu
                    165                 170                 175

Ala Arg Ala Val Leu Thr Phe Val Leu Asp Ser Val Glu Arg Lys Leu
                180                 185                 190

Leu Met Ser Ser Thr Lys Gly Leu Tyr Ser Asp Thr Glu Leu Gln Gln
            195                 200                 205

Cys Leu Ala Ala Ala Gln Ala Ala Ser Gln His Val Phe Arg Phe Tyr
        210                 215                 220

Arg Glu Ser Leu Gln Arg Arg Tyr Ser Lys Ser
225                 230                 235
```

(2) INFORMATION FOR SEQ ID NO:29:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..477

(xi) SEQUENCE DESCRIPTION: SEQ ID NO:29:

```
GAG GCT GCT GGC AGA GAG AGA GAG AGG ACT CTG GAG TAT GCC GAA GCA        48
Glu Ala Ala Gly Arg Glu Arg Glu Arg Thr Leu Glu Tyr Ala Glu Ala
  1               5                  10                  15

CAC GCC TTC AAG AGT CCC AGC AAA GAA AAT AAA AAG AAA GAC AAA GAT        96
His Ala Phe Lys Ser Pro Ser Lys Glu Asn Lys Lys Lys Asp Lys Asp
                 20                  25                  30

ATG CTT GAA GAT AAG TTT AAA AGC AAT AAT TTA GAG AGA GAG CAG GAG       144
Met Leu Glu Asp Lys Phe Lys Ser Asn Asn Leu Glu Arg Glu Gln Glu
             35                  40                  45

CAG CTT GAC CGC ATC GTG AAG GAA TCT GGA GGA AAG CTG ACC AGG CGG       192
Gln Leu Asp Arg Ile Val Lys Glu Ser Gly Gly Lys Leu Thr Arg Arg
     50                  55                  60

CTT GTG AAC AGT CAG TGC GAA TTT GAA AGA AGA AAA CCA GAT GGA ACA       240
Leu Val Asn Ser Gln Cys Glu Phe Glu Arg Arg Lys Pro Asp Gly Thr
 65                  70                  75                  80

ACG ACG TTG GGA CTT CTC CAT CCT GTG GAT CCC ATT GTA GGA GAG CCA       288
Thr Thr Leu Gly Leu Leu His Pro Val Asp Pro Ile Val Gly Glu Pro
                 85                  90                  95

GGC TAC TGC CCT GTG AGA CTG GGA ATG ACA ACT GGA AGA CTT CAG TCT       336
Gly Tyr Cys Pro Val Arg Leu Gly Met Thr Thr Gly Arg Leu Gln Ser
                100                 105                 110

GGA GTG AAT ACT TTG CAG GGG TTC AAA GAG GAT AAA AGG AAC AAA GTC       384
Gly Val Asn Thr Leu Gln Gly Phe Lys Glu Asp Lys Arg Asn Lys Val
            115                 120                 125

ACT CCA GTG TTA TAT TTG GAA TTA TGG GCC CCT ACA GTT CTT TAT GCA       432
Thr Pro Val Leu Tyr Leu Glu Leu Trp Ala Pro Thr Val Leu Tyr Ala
        130                 135                 140

CCG CAT TAT GAC TCC ACA TTT GCA AAT TAT CAG CAA GGA TTG ATC           477
Pro His Tyr Asp Ser Thr Phe Ala Asn Tyr Gln Gln Gly Leu Ile
145                 150                 155
```

(2) INFORMATION FOR SEQ ID NO:30:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:30:

```
Glu Ala Ala Gly Arg Glu Arg Glu Arg Thr Leu Glu Tyr Ala Glu Ala
  1               5                  10                  15

His Ala Phe Lys Ser Pro Ser Lys Glu Asn Lys Lys Lys Asp Lys Asp
                 20                  25                  30

Met Leu Glu Asp Lys Phe Lys Ser Asn Asn Leu Glu Arg Glu Gln Glu
             35                  40                  45

Gln Leu Asp Arg Ile Val Lys Glu Ser Gly Gly Lys Leu Thr Arg Arg
     50                  55                  60

Leu Val Asn Ser Gln Cys Glu Phe Glu Arg Arg Lys Pro Asp Gly Thr
 65                  70                  75                  80

Thr Thr Leu Gly Leu Leu His Pro Val Asp Pro Ile Val Gly Glu Pro
                 85                  90                  95
```

```
Gly Tyr Cys Pro Val Arg Leu Gly Met Thr Thr Gly Arg Leu Gln Ser
            100                 105                 110

Gly Val Asn Thr Leu Gln Gly Phe Lys Glu Asp Lys Arg Asn Lys Val
        115                 120                 125

Thr Pro Val Leu Tyr Leu Glu Leu Trp Ala Pro Thr Val Leu Tyr Ala
    130                 135                 140

Pro His Tyr Asp Ser Thr Phe Ala Asn Tyr Gln Gln Gly Leu Ile
145                 150                 155
```

(2) INFORMATION FOR SEQ ID NO:31:

(i) SEQUENCE CHARACTERISTICS:
       (A) LENGTH: 342 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..342

(xi) SEQUENCE DESCRIPTION: SEQ ID NO:31:

```
GGA CCG ATT CGA GAA GCT GGG CTG GCT GGC TGG CTG GCG CTG GGC TGT     48
Gly Pro Ile Arg Glu Ala Gly Leu Ala Gly Trp Leu Ala Leu Gly Cys
1               5                   10                  15

AGT GGG CCC CCA GCG GAG GCC GCC GGA GGA GCG GGC GAG CCC TGG CCG     96
Ser Gly Pro Pro Ala Glu Ala Ala Gly Gly Ala Gly Glu Pro Trp Pro
            20                  25                  30

CAG CAC TCC GGG AAA GGG CAG TTG GCT GGC AGA AAC GCT TGG GTG AAA    144
Gln His Ser Gly Lys Gly Gln Leu Ala Gly Arg Asn Ala Trp Val Lys
        35                  40                  45

AAG CGG AAA GCG CCA CGT GAG AAC AGC CCC GGC GTG CGG TCC TGC AGG    192
Lys Arg Lys Ala Pro Arg Glu Asn Ser Pro Gly Val Arg Ser Cys Arg
    50                  55                  60

GCC TCA GGG CGG GCA TCA AGG CCC CAT GGG GAT CCA TTC CTC CTC ACG    240
Ala Ser Gly Arg Ala Ser Arg Pro His Gly Asp Pro Phe Leu Leu Thr
65                  70                  75                  80

CTT CCT CGT GCC AGG CAT CCG GTT ACA CTA AAC GTG ACC ATA CAA GTC    288
Leu Pro Arg Ala Arg His Pro Val Thr Leu Asn Val Thr Ile Gln Val
                85                  90                  95

TCC CTC AAA CAG CGG AAC GTG AGG TTC AAT ACT CCA TTT CGC AGA GGA    336
Ser Leu Lys Gln Arg Asn Val Arg Phe Asn Thr Pro Phe Arg Arg Gly
            100                 105                 110

GAA AAC                                                            342
Glu Asn
```

(2) INFORMATION FOR SEQ ID NO:32:

(i) SEQUENCE CHARACTERISTICS:
       (A) LENGTH: 114 amino acids
       (B) TYPE: amino acid
       (D) TOPOLOGY: linear (ii) MOLECULE TYPE: protein (xi) SEQUENCE DESCRIPTION: SEQ ID NO:32:

```
Gly Pro Ile Arg Glu Ala Gly Leu Ala Gly Trp Leu Ala Leu Gly Cys
1               5                   10                  15

Ser Gly Pro Pro Ala Glu Ala Ala Gly Gly Ala Gly Glu Pro Trp Pro
            20                  25                  30

Gln His Ser Gly Lys Gly Gln Leu Ala Gly Arg Asn Ala Trp Val Lys
```

```
                35                   40                     45
Lys Arg Lys Ala Pro Arg Glu Asn Ser Pro Gly Val Arg Ser Cys Arg
        50                  55                  60

Ala Ser Gly Arg Ala Ser Arg Pro His Gly Asp Pro Phe Leu Leu Thr
65                  70                  75                  80

Leu Pro Arg Ala Arg His Pro Val Thr Leu Asn Val Thr Ile Gln Val
                85                  90                  95

Ser Leu Lys Gln Arg Asn Val Arg Phe Asn Thr Pro Phe Arg Arg Gly
            100                 105                 110

Glu Asn
```

(2) INFORMATION FOR SEQ ID NO:33:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
GAAGACAGAA CTTCAGAAGA AAACTACCTG ACACACAGTG ACACAGCCAG AATTCAGCAA      60
GCATTTCCTA TGCACAGGGA GATAGCAGTG GATTTTGGTT TGGAATCAAG ACGTGATCAG     120
AGTTCCAGCG TGGCAGAAGA ACAAATTGGC CC                                   152
```

(2) INFORMATION FOR SEQ ID NO:34:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
CTAGTCGGAA TTCGGCACGA GGCCTCGTGC CGAATTCGGC ACGAGGGCAA GAAGGTGAGG      60
CGCCTAATGG GAAAGTCGCA CATTGGGCTT GTGTACAGCC AGCAAATCAA TGAGGTGCTT     120
GATCAGCTGG CGAACCTGAA TGGACGCGAT CTCTCTATCT GGTCCAGTGG CAGCCGGCAC     180
ATGAAGAAGC AGACATTTGT GGTACATGCA GGGACAGATA CAAACGGAGA TTTCTTTTTC     240
ATGGAGGTGT GCGATGACTG TGTGGTGTTG CGTAGTAACA TCGGAACAGT GTATGAGCGC     300
TGGTGGTACG AGAAGCTCAT CAACATGACC TACTGTCCCA AGACGAAGGT GTTGTGCTTG     360
TGGCGTAGGA AATGGTTC                                                   378
```

(2) INFORMATION FOR SEQ ID NO:35:

(i) SEQUENCE CHARACTERISTICS:
        (A) LENGTH: 532 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

```
ATTCGGCACG AGGCGGGGCC TCGGCCTACA GCGACCCCGT GCGGCTGCGT TAAGCCGGCT      60
CTGGAGACAG GGAATCTTTT AACTGAGCCA GTCGGCTACT TGGAATCTTG TTTCTCGGCC     120
```

```
AAGAATGGTA CTCCAAGACA GCCATCCATT TGTAGCTATT CTCGAGCCTG TTTGAGGATT     180

AGAAAGAGGA TCTTTAATAA TCCTGAACAT TCCTTGATGG GCCTAGAACA GTTTTCTCAT     240

GTTTGGATTT TGTTTGTTTT TCACAAAAAT GGTCATTTGA GCTGTAAGGC AAAAGTGCAG     300

CCTCCTAGGC TGAATGGTGC AAAGACTGGA GTTTTTTCCA CAAGGAGCCC TCATCGTCCC     360

AATGCAATAG GACTGACCCT GGCCAAGCTG GAAAAGGTAG TAGGTGGGGA GGCTTATATA     420

CCTTTCTGGA ATTTGACATG ATACATGGCA CACCCGTACT AGACATCAAG CCCTACATAG     480

CTGAGTTTTG ACTCACCGCA AAATGTGATG GCAGCCCTTT AGCAGACTTT TA            532

(2) INFORMATION FOR SEQ ID NO:36:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

ATTCGGCACG AGGCTGGGAG GATGACATGC AGAGGAACTG AGATCGACAG TGACTAGTGA      60

CCCCTTGTTG AGGGGTAAGC CAGGCTAGGG GACTGCACAA TTATACACTA TTTATTTATT     120

TATTCTCCTT GGGGTTGGTG TCAGGGGCGA GCCAACCCCA CCTCTATGCC CTGAGCCCTG     180

GTAGTCCAGA GACCCCAACT CTGCCCTGGC TTCTCTGGTT CTTCCCTGTG GAAAGCCCAT     240

CCTGAGACAT CTTGCTGGAA CCAAGGCAAT CCTGGATGTC CTGGTACTGA CCCACCCGCC     300

TGTGAATGTG TCCACTCTCT TCTGCCCCCA GCCATATTTG GGGAGGATGG GTCAACTACA     360

ATAGGTAAGA AAATGCAGCC GGAGCCTCAG TCCCCAGCAA GGAGCCTGTG TCTCACCCCC     420

TCACAGGACA GAGCTGTATC TTGCATAGAG CTGGGTCTCA CTGTTGGCGC AGG           473

(2) INFORMATION FOR SEQ ID NO:37:

(i) SEQUENCE CHARACTERISTICS:
        (A) LENGTH: 426 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

Asp Thr Asp Cys Arg Glu Cys Glu Ser Gly Ser Phe Thr Ala Ser Glu
    50                  55                  60

Asn His Leu Arg His Cys Leu Ser Cys Ser Lys Cys Arg Lys Glu Met
65                  70                  75                  80

Gly Gln Val Glu Ile Ser Ser Cys Thr Val Asp Arg Asp Thr Val Cys
                85                  90                  95

Gly Cys Arg Lys Asn Gln Tyr Arg His Tyr Trp Ser Glu Asn Leu Phe
            100                 105                 110

Gln Cys Phe Asn Cys Ser Leu Cys Leu Asn Gly Thr Val His Leu Ser
        115                 120                 125
```

―continued

```
Cys Gln Glu Lys Gln Asn Thr Val Cys Thr Cys His Ala Gly Phe Phe
    130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn Val Lys Gly Thr
            165                 170                 175

Glu Asp Ser Gly Thr Thr Val Leu Leu Pro Leu Val Ile Phe Phe Gly
                180                 185                 190

Leu Cys Leu Leu Ser Leu Leu Phe Ile Gly Leu Met Tyr Arg Tyr Gln
        195                 200                 205

Arg Trp Lys Ser Lys Leu Tyr Ser Ile Val Cys Gly Lys Ser Thr Pro
    210                 215                 220

Glu Lys Glu Gly Glu Leu Glu Gly Thr Thr Thr Lys Pro Leu Ala Pro
225                 230                 235                 240

Asn Pro Ser Phe Ser Pro Thr Pro Gly Phe Thr Pro Thr Leu Gly Phe
            245                 250                 255

Ser Pro Val Pro Ser Ser Thr Phe Thr Ser Ser Ser Thr Tyr Thr Pro
                260                 265                 270

Gly Asp Cys Pro Asn Phe Ala Ala Pro Arg Arg Glu Val Ala Pro Pro
        275                 280                 285

Tyr Gln Gly Ala Asp Pro Ile Leu Ala Thr Ala Leu Ala Ser Asp Pro
    290                 295                 300

Ile Pro Asn Pro Leu Gln Lys Trp Glu Asp Ser Ala His Lys Pro Gln
305                 310                 315                 320

Ser Leu Asp Thr Asp Asp Pro Ala Thr Leu Tyr Ala Val Val Glu Asn
            325                 330                 335

Val Pro Pro Leu Arg Trp Lys Glu Phe Val Arg Arg Leu Gly Leu Ser
                340                 345                 350

Asp His Glu Ile Asp Arg Leu Glu Leu Gln Asn Gly Arg Cys Leu Arg
        355                 360                 365

Glu Ala Gln Tyr Ser Met Leu Ala Thr Trp Arg Arg Arg Thr Pro Arg
    370                 375                 380

Arg Glu Ala Thr Leu Glu Leu Leu Gly Arg Val Leu Arg Asp Met Asp
385                 390                 395                 400

Leu Leu Gly Cys Leu Glu Asp Ile Glu Glu Ala Leu Cys Gly Pro Ala
            405                 410                 415

Ala Leu Pro Pro Ala Pro Ser Leu Leu Arg
                420                 425
```

MODULATOR OF TNF/NGF SUPERFAMILY RECEPTORS AND SOLUBLE OLIGOMERIC TNF/NGF SUPERFAMILY RECEPTORS

CROSS-REFERENCE TO RELATED APPLICATIONS

This application is a continuation-in-part of PCT/US95/05854, filed May 11, 1995, the entire contents of which are hereby incorporated by reference.

FIELD OF THE INVENTION

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs) and the FAS ligand receptor (also called FAS/APO1 or FAS-R and hereinafter will be called FAS-R) and others. More specifically, the present invention concerns novel proteins which bind to the intracellular domains (IC) of the p55 and p75 TNF-Rs and the FAS-R, (these intracellular domains designated p55IC, p75IC and FAS-IC, respectively) and which novel proteins are capable of modulating the function of the p55 and p75 TNF-Rs and the FAS-R. One of the proteins capable of binding the p55IC of the intact p55-TNF-R is the p55IC itself in the form of a p55IC molecule or a portion thereof, such as for example, the so-called "death domain" (DD) of the p55IC. Thus, the present invention also concerns new TNF-associated effects that can be induced in cells in a ligand (TNF)-independent fashion by the intracellular domain of the p55 TNF-R (p55IC) or portions thereof. The present invention also concerns the preparation and uses of these novel p55 and p75 TNF-R-binding proteins, and FAS-R binding proteins, referred to herein as p55IC-, p75IC- and FAS-IC-binding proteins.

In another aspect, the present invention also concerns new soluble oligomeric TNF-Rs, oligomeric FAS-Rs and oligomeric receptors having a mixture of TNF-Rs and FAS-Rs, their uses, and methods for the production thereof.

BACKGROUND OF THE INVENTION

Tumor Necrosis Factor (TNF-α) and Lymphotoxin (TNF-β) (hereinafter, TNF refers to both TNF-α and TNF-β) are multifunctional pro-inflammatory cytokines formed mainly by mononuclear phagocytes, which have many effects on cells (Wallach, D. (1986) in: Interferon 7 (Ion Gresser, ed.), pp. 83–122, Academic Press, London; and Beutler and Cerami (1987)). Both TNF-α and TNF-β initiate their effects by binding to specific cell surface receptors. Some of the effects are likely to be beneficial to the organism: they may destroy, for example tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that over-production of TNF-α can play a major pathogenic role in several diseases. Thus, effects of TNF-α, primarily on the vasculature, are now known to be a major cause for symptoms of septic shock (Tracey et al., 1986). In some diseases, TNF may cause excessive loss of weight (cachexia) by suppressing activities of adipocytes and by causing anorexia, and TNF-α was thus called cachectin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Leotscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 an p75 TNF-Rs have yet to be elucidated (as set forth herein below, there is described for the first time, new proteins capable of binding to the p75IC and p55 IC). It is this intracellular signaling, which occurs usually after the binding of the ligand, i.e. TNF (α or β), to the receptor, that is responsible for the commencement of the cascade of reactions that ultimately result in the observed response of the cell to TNF.

As regards the above mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer and as such has been suggested to induce intracellular signaling via the p55 TNF-R by way of its ability to bind to and to cross-link the receptor molecules, i.e. cause receptor aggregation. Herein below there is described how the p55IC and p55DD can self-associate and induce, in a ligand-independent fashion, TNF-associated effects in cells.

Another member of the TNF/NGF superfamily of receptors is the FAS receptor (FAS-R) which has also been called the FAS antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e. during maturation of T cells, FAS-R mediates the apoptotic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptotic cell death of the FAS-R-carrying cells. Further, a monoclonal antibody has been prepared that is specific for FAS-R, this monoclonal antibody being capable of inducing apoptotic cell death in cells carrying FAS-R, including mouse cells transformed by cDNA encoding human FAS-R (Itoh et al., 1991).

It has also been found that various other normal cells, besides T lymphocytes, express the FAS-R on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of FAS-R may have therapeutic potential.

Conversely, since it has also been found that certain malignant cells and HIV-infected cells carry the FAS-R on their surface, antibodies against FAS-R, or the FAS-R ligand, may be used to trigger the FAS-R mediated cytotoxic effects in these and thereby provide a means for combating such malignant cells or HIV-infected cells (see Itoh et al., 1991). Finding yet other ways for enhancing the cytotoxic activity of FAS-R may therefore also have therapeutic potential.

It has been a long felt need to provide a way for modulating the cellular response to TNF ($\alpha$ or $\beta$) and FAS-R ligand, for example, in pathological situations as mentioned above, where TNF or FAS-R ligand is over-expressed it is desirable to inhibit the TNF- or FAS-R ligand-induced cytocidal effects, while in other situations, e.g. wound healing applications, it is desirable to enhance the TNF effect, or in the case of FAS-R, in tumor cells or HIV-infected cells it is desirable to enhance the FAS-R mediated effect.

A number of approaches have been made by the present inventors (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by the present inventors (see for example EPO 568925) have been made to modulate the TNF effect by modulating the activity of the TNF-Rs. Briefly, EPO 568925 relates to a method of modulating signal transduction and/or cleavage in TNF-Rs whereby peptides or other molecules may interact either with the receptor itself or with effector proteins interacting with the receptor, thus modulating the normal functioning of the TNF-Rs. In EPO 568925 there is described the construction and characterization of various mutant p55 TNF-Rs, having mutations in the extracellular, transmembranal, and intracellular domains of the p55 TNF-R. In this way regions within the above domains of the p55 TNF-R were identified as being essential to the functioning of the receptor, i.e. the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EPO 568925. However, no description is made in EPO 568925 of the actual proteins and peptides which bind to the intracellular domains of the TNF-Rs (e.g. p55 TNF-R), nor is any description made of the yeast two-hybrid approach to isolate and identify such proteins or peptides which bind to the intracellular domains of TNF-Rs. Similarly, heretofore there has been no disclosure of proteins or peptides capable of binding the intracellular domain of FAS-R.

Thus, when it is desired to inhibit the effect of TNF, or the FAS-R ligand, it would be desirable to decrease the amount or the activity of TNF-Rs or FAS-R at the cell surface, while an increase in the amount or the activity of TNF-Rs or FAS-R would be desired when an enhanced TNF or FAS-R ligand effect is sought. To this end the promoters of both the p55 TNF-R and the p75 TNF-R have recently been sequenced and analyzed by the present inventors and a number of key sequence motifs have been found that are specific to various transcription regulating factors, and as such the expression of these TNF-Rs can be controlled at their promoter level, i.e. inhibition of transcription from the promoters for a decrease in the number of receptors, and an enhancement of transcription from the promoters for an increase in the number of receptors (see WO 95/31206 and U.S. Ser. No. 08/600,203). Corresponding studies concerning the control of FAS-R at the level of the promoter of the FAS-R gene have yet to be reported.

Further, it should also be mentioned that, while it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the "death domains") have sequence similarity. The "death domains" of both FAS-R and p55-R tend to self-associate. Their self-association apparently promotes that receptor aggregation which is necessary for initiation of signaling (as set forth herein below, as well as Song et al., 1994; Wallach et al., 1994; Boldin et al., 1995) and at high levels of receptor expression can result in triggering of ligand-independent signaling (as set forth herein below, and Boldin et al., 1995).

Thus, prior to the present invention, there have not been provided proteins which may regulate the effect of ligands belonging to the TNF/NGF superfamily, such as the TNF or FAS-R ligand effect on cells, by mediation of the intracellular signaling process, which signaling is probably governed to a large extent by the intracellular domains (ICs) of the receptors belonging to the TNF/NGF superfamily of receptors, such as those of the TNF-Rs, i.e. the p55 and p75 TNF-R intracellular domains (p55IC and p75IC, respectively), as well as the FAS-IC.

Accordingly, it is one aim of the invention to provide proteins which are capable of binding to the intracellular domains of the TNF-Rs and FAS-R, which proteins are presently believed to be involved in the intracellular signaling process initiated by the binding of TNF to its receptors, or the binding of FAS ligand to its receptor.

Another aim of the invention is to provide antagonists (e.g. antibodies) to these intracellular domain-binding proteins (IC-binding proteins) which may be used to inhibit the signaling process, when desired, when such IC-binding proteins are positive signal effectors (i.e. induce signaling), or to enhance the signaling process, when desired, when such IC-binding proteins are negative signal effectors (i.e. inhibit signaling).

Yet another aim of the invention is to use such IC-binding proteins to isolate and characterize additional proteins or factors, which may, for example, be involved further downstream in the signaling process, and/or to isolate and identify other receptors further upstream in the signaling process to which these IC-binding proteins bind (e.g. other TNF-Rs or related receptors), and hence, in whose function the IC-binding proteins are also involved.

Moreover, it is an aim of the present invention to use the above-mentioned IC-binding proteins as antigens for the preparation of polyclonal and/or monoclonal antibodies thereto. The antibodies, in turn, may be used for the purification of the new IC-binding proteins from different sources, such as cell extracts or transformed cell lines.

Furthermore, these antibodies may be used for diagnostic purposes, e.g. for identifying disorders related to abnormal functioning of cellular effects mediated by receptors belonging to the TNF/NGF receptor superfamily.

A further aim of the invention is to provide pharmaceutical compositions comprising the above IC-binding proteins, and pharmaceutical compositions comprising the IC-binding protein antagonists, for the treatment or prophylaxis of TNF-induced or FAS ligand-induced conditions, for example, such compositions can be used to enhance the TNF or FAS ligand effect or to inhibit the TNF or FAS ligand effect depending on the above noted nature of the IC-binding protein or antagonist thereof contained in the composition.

Moreover, in accordance with another aim of the present invention, there is disclosed other ways for eliminating or antagonizing endogenously formed or exogenously administered TNF or FAS-R ligand, by the use of soluble oligomeric TNF-Rs, oligomeric FAS-Rs, or oligomers being a mixture of TNF-Rs and FAS-Rs. In this respect it should be mentioned that one attempt in this direction was the isolation and recombinant production of a TNF Binding Protein called TBP-I which was shown to be able to antagonize the effects of TNF. This antagonism was determined both by measuring reduction of the cytotoxic activity of TNF, as well as by measuring interference of TNF binding to its receptors (EP 308 378). TBP-I was shown to protect cells from TNF toxicity at concentrations of a few nanograms per ml and to interfere with the binding of both TNF-α and TNF-β to cells, when applied simultaneously with these cytokines. Further examination of the mechanism by which TBP-I functions revealed that TBP-I does not interact with the target cell, but rather blocks the function of TNF by binding TNF specifically, thus competing for TNF with the TNF receptor.

Consequently, with a different purification technique, the presence of two active components was found: one, TBP-I, and also a second TNF-binding protein which we called TBP-II (first described in EP 398327). Both proteins provide protection against the in vitro cytocidal effect of TNF and both bind TNF-β less effectively than TNF-α. Although in SDS PAGE analysis the two proteins, TBP-I and TBP-II, appeared to have a very similar molecular size, they could clearly be distinguished from each other by lack of immunological cross reactivity, differing N-terminal amino acid sequences and differing amino acid composition.

However, the above noted earlier soluble TNF binding proteins are monomeric and being capable of binding only one monomer of the TNF homotrimer, the natural ligand, which still permits TNF activity (i.e. incomplete neutralization) by virtue of the TNF still having two active monomers unbound by the TNF binding proteins. Further, heretofore there has been no disclosure of soluble FAS-Rs (soluble FAS-R ligand binding proteins) capable of binding to FAS-R ligand which is known to be a homotrimeric, cell-surface associated molecule.

A so-called "death domain" of the p55-IC (Tartaglia et al., 1993) has been disclosed, but did not show, in accordance with the present invention, that the p55-IC and the "death domain" thereof self-associates, this self-association being primarily responsible for the signaling leading to induction of cell cytotoxis. Moreover, this publication is silent on the possibility of producing the soluble, oligomeric TNF-Rs, or the soluble, oligomeric FAS-Rs, or mixed oligomeric thereof, nor does it disclose other TNF-associated effects induced by the p55-IC or portions thereof, e.g. IL-8 gene expression induction, all of the present invention. Likewise, another publication, published after the date of the present invention, disclosed the aggregation (i.e. self-association) ability of the p55-IC, but did not relate, as noted above, to the usage thereof to prepare soluble, oligomeric TNF-Rs or FAS-Rs nor to the other TNF-associated effects induced in a ligand-independent manner by the p55-IC or portions thereof according to the invention.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

In accordance with the present invention, we have found novel proteins which are capable of binding to either the intracellular domain of the p55 TNF-R (the p55IC-binding proteins), of the p75 TNF-R (the p75IC-binding proteins), and of the FAS-R (the FAS-IC-binding proteins). These p55IC-, p75IC- and FAS-IC-binding proteins may act as mediators or modulators of the TNF or FAS-R ligand effect on cells by way of mediating or modulating the intracellular signaling process which usually occurs following the binding of TNF to the p55 and/or p75 TNF-R, or the binding of the FAS-R ligand at the cell surface. Further, it has been surprisingly and unexpectedly found that the p55IC and FAS-IC are capable of self association and that fragments of the p55IC and FAS-IC are similarly capable of binding to the p55 IC, particularly the so-called "death domains" (DD) within the ICs of these receptors, i.e. the p55DD and FAS-DD. Thus, p55 IC and FAS-IC and their fragments also represent proteins capable of binding to the p55IC and FAS-IC and hence may be modulators of the TNF or FAS-R ligand effect on cells.

Furthermore, the nature of the binding of one of the novel proteins of the invention, the herein designated 55.11 protein, to the intracellular domain of p55-TNF-R has been more fully elucidated (see Example 1).

Moreover, in another aspect, the present invention is based on the finding that the intracellular domain of the p55 TNF receptor (p55-IC), a region contained therein, the so-called p55-IC "death domain", the intracellular domain of the FAS/APO1 receptor (FAS-IC), and a region contained therein, the so-called FAS-IC "death domain" are capable of self-association. Accordingly, it is possible to construct by standard recombinant DNA techniques, a soluble, oligomeric TNF receptor being a fusion product, containing at least two extracellular domains of a TNF receptor at its one end, and at its other end at least two of the above noted self-associating intracellular domains or portions thereof, which self-associate to provide an oligomer having at least two such fusion products linked together. Such a soluble, oligomeric TNF-R is thus capable of binding two monomers of the naturally-occurring TNF homotrimer, and as such effectively neutralizes TNF activity. The neutralization of TNF activity being desirable in all of the above mentioned conditions wherein TNF is overproduced endogenously or is administered exogenously in high doses resulting in undesirable side effects. Further, the effective binding of TNF by the soluble, oligomeric receptors of the invention may also serve to allow for the binding of exogenously added TNF and its subsequent desired slow-release in conditions where TNF is administered for its beneficial effects, e.g. in tumor therapy. Likewise, it is also possible to construct by standard recombinant DNA techniques an oligomeric FAS-R being a fusion product, containing at least two extracellular domains of a FAS-R at its one end, and at its other end at least two of the above noted self-associating intracellular domains or portions thereof, which self-associate to provide an oligomer having at least two such fusion products linked together. Such an oligomeric FAS-R is thus capable of binding two monomers of the naturally occurring FAS-R ligand homotrimer, and as such effectively neutralizes FAS-R ligand activity. The neutralization of FAS-R ligand activity being desirable in all of the above mentioned conditions where excess amounts thereof are associated with undesirable side effects. In a similar fashion, and in view of recent reports indicating a possible associating between TNF and FAS-R ligand-induced effects on cells and hence also a possible association, geographically at the cell surface where they attach to their receptors, it is also possible to construct by standard recombinant DNA techniques a mixed oligomeric receptor having specificity for both TNF and FAS-R ligand. Such a mixed oligomer would be a mixture of the above noted fusion products containing at least one extracellular domain of a TNF-R and at least one extracellular domain of a FAS-R at its one end, and at its other end at least two of the above mentioned self-associating intracellular domains or portions thereof, which self-associate to provide a mixed oligomer having at least two such fusion products linked together. Such a mixed oligomer is thus capable of binding at least one monomer of TNF and one monomer of FAS-R ligand at the same time, thereby reducing or effectively neutralizing the TNF and FAS-R ligand activities at the cell surface in conditions, as noted above where excess amounts of these two cytokines are associated with undesirable cellular effects. As noted above, the FAS-R ligand is usually cell-surface-associated, and recent reports also describe cell-surface-associated forms of TNF. Hence, these mixed TNF-R/FAS-R oligomers are especially useful for neutralization of TNF and FAS-R ligand activities at the cell surface.

Accordingly, the present invention provides a DNA sequence encoding a protein capable of binding to one or more of the intracellular domains of one or more receptors belonging to the tumor necrosis factor/nerve growth factor (TNF/NGF) superfamily of receptors.

In particular, the present invention provides a DNA sequence selected from the group consisting of:
  (a) a cDNA sequence derived from the coding region of a native TNF-R intracellular domain-binding protein;
  (b) DNA sequences capable of hybridization to a DNA of (a) under moderately stringent conditions and which encode a biologically active TNF-R intracellular domain-binding protein; and
  (c) DNA sequences which are degenerate as a result of the genetic code to the DNA sequences defined in (a) and (b) and which encode a biologically active TNF-R intracellular domain-binding protein.

The present invention also provides a DNA sequence selected from the group consisting of:
  (a) a cDNA sequence derived from the coding region of a native FAS-R intracellular domain-binding protein;
  (b) DNA sequences capable of hybridization to a cDNA of (a) under moderately stringent conditions and which encode a biologically active FAS-R intracellular domain-binding protein; and
  (c) DNA sequences which are degenerate as a result of the genetic code to the DNA sequences defined in (a) and (b) and which encode a biologically active FAS-R intracellular domain-binding protein.

In embodiments of the present invention the DNA sequences encode p55 TNF-R, p75 TNF-R and FAS-R intracellular domain-binding proteins, such as those encoding the herein designated proteins 55.1, 55.3, 55.11, 75.3, 75.16, F2, F9, DD11, E3, E15, E19, 230, 4, 65, 14v1 and 16v1.

The present invention also provides a protein or analogs or derivatives thereof encoded by any of the above sequences of the invention, said proteins, analogs and derivatives being capable of binding to one or more of the intracellular domains of one or more TNF-Rs or FAS-R. Embodiments of this aspect of the invention include the herein designated proteins 55.1, 55.3, 55.11, 75.3, 75.16, F2, F9, DD11, E3, E15, E19 and 230, their analogs and their derivatives as well as the p55IC-binding proteins encoded by the clones designated 4, 65, 14v1 and 16v1.

Also provided by the present invention are vectors encoding the above proteins of the invention, which contain the above DNA sequences of the invention, these vectors being capable of being expressed in suitable eukaryotic or prokaryotic host cells; transformed eukaryotic or prokaryotic host cells containing such vectors; and a method for producing the proteins, analogs or derivatives of the invention by growing such transformed host cells under conditions suitable for the expression of said protein, analogs or derivatives, effecting post-translational modifications of said protein as necessary for obtention of said protein and extracting said expressed protein, analogs or derivatives from the culture medium of said transformed cells or from cell extracts of said transformed cells.

In another aspect, the present invention also provides antibodies or active derivatives or fragments thereof specific to the proteins, analogs and derivatives thereof, of the invention.

By yet another aspect of the invention, there are provided various uses of the above DNA sequences or the proteins which they encode, according to the invention, which uses include amongst others:
  (i) a method for the modulation of the TNF or FAS-R ligand effect on cells carrying a TNF-R or a FAS-R, comprising treating said cells with one or more proteins, analogs or derivatives selected from the group consisting of the proteins, analogs and derivatives, according to the invention, and a protein being the p55IC, p55DD, FAS-IC or FAS-DD, analogs or derivatives thereof, all of said proteins being capable of binding to the intracellular domain and modulating the activity of said TNF-R or FAS-R, wherein said treating of the cells comprises introducing into said cells said one or more proteins, analogs or derivatives in a form suitable for intracellular administration or introducing into said cells, in the form of a suitable expression vector, the DNA sequence encoding said one or more proteins, analogs or derivatives;

(ii) a method for modulating the TNF or FAS-R ligand effect on cells carrying a TNF-R or a FAS-R comprising treating said cells with antibodies or active derivatives or fragments thereof according to the invention;

(iii) a method for modulating the TNF or FAS-R ligand effect on cells carrying a TNF-R or FAS-R comprising treating said cells with an oligonucleotide sequence encoding an antisense sequence of at least part of the sequence according to the invention, or encoding an antisense sequence of the p55IC, p55DD, FAS-IC, or FAS-DD sequence, said oligonucleotide sequence being capable of blocking the expression of at least one of the TNF-R or FAS-R intracellular domain binding proteins;

(iv) a method for modulating the TNF or FAS-R ligand effect on cells carrying a TNF-R or FAS-R comprising:
(a) constructing a recombinant animal virus vector carrying a sequence encoding a viral surface protein that is capable of binding to a specific cell surface receptor and a sequence selected from an oligonucleotide sequence encoding an antisense sequence of at least part of the sequence according to the invention and an oligonucleotide sequence encoding an antisense sequence of the p55IC, p55DD, FAS-IC, or FAS-DD sequence, said oligonucleotide sequence being capable of blocking the expression of at least one of the TNF-R or FAS-R intracellular domain binding proteins when introduced into said cells by said virus; and
(b) infecting said cells with said vector of (a).

(v) a method for modulating the TNF or FAS-R ligand effect on cells carrying a TNF-R or a FAS-R, comprising treating said cells with a suitable vector encoding a ribozyme having a sequence specific to a sequence selected from an mRNA sequence encoding a protein, analog or derivative of the invention and an mRNA sequence encoding the p55IC, p55DD, FAS-IC or FAS-DD, said ribozyme sequence capable of interacting with said mRNA sequence and capable of cleaving said mRNA sequence resulting in the inhibition of the expression of the protein, analog or derivative of the invention or of the expression of the p55IC, p55DD, FAS-IC or FAS-DD;

(vi) a method for treating tumor cells or HIV-infected cells, or other diseased cells, comprising:
(a) constructing a recombinant animal virus vector carrying a sequence encoding a viral surface protein that is capable of binding to a tumor cell surface receptor or HIV-infected cell surface receptor or is capable of binding to another cell surface receptor of other diseased cells and a sequence selected from a sequence according to the invention encoding a protein, analog or derivative of the invention and a sequence encoding the p55IC, p55DD, FAS-IC, FAS-DD, or a biologically active analog or derivative thereof, said protein, analog or derivative of the invention, p55IC, p55DD, FAS-IC, FAS-DD, analog or derivative, when expressed in said tumor cell or HIV-infected cell, or other diseased cell being capable of killing said cell; and
(b) infecting said tumor cells or HIV-infected cells or other infected cells with said vector of (a);

(vii) a method for isolating and identifying proteins, factors or receptors capable of binding to the intracellular domain binding proteins according to the invention, comprising applying the procedure of affinity chromatography in which said protein according to the invention is attached to the affinity chromatography matrix, said attached protein is brought into contact with a cell extract and proteins, factors or receptors from cell extract which bound to said attached protein are then eluted, isolated analyzed;

(viii) a method for isolating and identifying proteins, capable of binding to the intracellular domain binding proteins according to the invention, comprising applying the yeast two-hybrid procedure in which a sequence encoding said intracellular domain binding protein is carried by one hybrid vector and a sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said intracellular domain binding protein; and (ix) a method for isolating and identifying a protein capable of binding to the intracellular domains of TNF-Rs or FAS-R comprising applying the procedure of non-stringent southern hybridization followed by PCR cloning, in which a sequence or parts thereof according to the invention is used as a probe to bind sequences from a cDNA or genomic DNA library, having at least partial homology thereto, said bound sequences then amplified and cloned by the PCR procedure to yield clones encoding proteins having at least partial homology to said sequences according to the invention.

The present invention also provides a pharmaceutical composition for the modulation of the TNF- or FAS ligand-effect on cells comprising, as active ingredient, any one of the following: (i) a protein according to the invention, or the protein p55IC, p55DD, FAS-IC or FAS-DD, its biologically active fragments, analogs, derivatives or mixtures thereof; (ii) a recombinant animal virus vector encoding a viral surface protein capable of binding to a TNF-R or FAS-R—carrying cell—or tumor cell-specific receptor and a sequence encoding a protein, analog or derivative of the invention or encoding the p55IC, p55DD, FAS-IC or FAS-DD; (iii) a recombinant animal virus vector encoding a viral surface protein as in (ii) above and an oligonucleotide sequence encoding an antisense sequence of the p55IC, p55DD, FAS-IC or FAS-DD sequence; and (iv) a vector encoding a ribozyme of sequence capable of interacting with a mRNA sequence encoding a protein, analog or derivative of the invention or a mRNA sequence encoding the p55IC, p55DD, FAS-IC or FAS-DD.

A specific embodiment of the above aspects of the invention is the use of the p55-IC or DNA encoding therefor. This embodiment is based on the discovery that the p55-IC may in a ligand (TNF)-independent fashion induce other TNF-associated effects in cells. Accordingly, there is provided a method for inducing TNF-associated effects in cells or tissues comprising treating said cells with one or more proteins, analogs or derivatives thereof, said one or more proteins being selected from a protein being essentially all of the self-associating intracellular domain of the p55 TNF-R (p55-IC) or portions thereof capable of self-associating and inducing, in a ligand (TNF)-independent manner, said TNF effect in the cells, wherein said treating of the cells comprises introducing into said cells said one or more proteins, analogs or derivatives in a form suitable for intracellular introduction thereof, or introducing into said cells a DNA sequence encoding said one or more proteins, analogs or derivatives in the form of a suitable vector carrying said sequence, said vector being capable of effecting the insertion of said sequence into said cells in a way that said sequence is expressed in said cells.

Embodiments of the above method of the invention include:

(i) a method wherein said treating of cells is by transfection of said cells with a recombinant animal virus vector comprising the steps of:
  (a) constructing a recombinant animal virus vector carrying a sequence encoding a viral surface protein (ligand) that is capable of binding to a specific cell surface receptor on the surface of said cells to be treated, and a second sequence encoding a protein being the p55-IC, portions thereof, analogs and derivatives of all of the foregoing, said protein when expressed in said cells being capable of self-association and induction of said one or more TNF-associated effects; and
  (b) infecting said cells with the vector of (a).

(ii) a method wherein said TNF effect to be induced in said cells is the induction of IL-8 gene expression, said vector carrying a sequence encoding essentially all of said p55-IC, portions thereof, analogs and derivatives of all of the foregoing, which are capable, when expressed in the cells of self-association and signaling for the induction of said IL-8 gene expression.

(iii) a method for treating tumor cells or virally-infected cells, or for augmenting the antibacterial effect of granulocytes, wherein said viral vector carries a sequence encoding a viral ligand capable of binding a specific cell surface receptor on the surface of said tumor cells, virally-infected cells or granulocytes and a sequence encoding said p55-IC portions thereof, analogs and derivatives thereof, which when expressed in said tumor, virally-infected or granulocyte cells induces TNF-associated effects leading to the death of these cells.

(iv) a method for treating tumor cells, wherein said p55-IC, portions thereof, analogs or derivatives thereof, when expressed in the tumor cells, induce the expression of IL-8 which leads to the killing of said tumor cells by its chemotactic activity which attracts granulocytes and other lymphocytes to the tumor cells resulting in the death of the tumor cells.

In this aspect of the invention, there is thus also provided the intracellular domain of the p55-R (p55-IC), portions, analogs and derivatives of all of the aforegoing for use in the treatment of cells by induction therein of TNF-associated effects; and the following embodiments thereof:

(i) the p55-IC, portions, analogs and derivatives for use in the treatment of cells by induction therein of IL-8 gene expression;

(ii) the p55-IC, portions, analogs and derivatives for use in the treatment of tumor cells by induction therein of IL-8 gene expression resulting in the killing of the tumor cells.

Moreover, in this aspect of the invention there is provided a pharmaceutical composition for treating cells by induction therein of TNF-associated effects, comprising, as active ingredient, p55-IC, portions thereof, analogs and derivatives of all of the aforegoing, and a pharmaceutically acceptable carrier; and the following embodiments thereof:

(i) a pharmaceutical composition for treating cells by induction therein of TNF-associated effects, comprising, as active ingredient a recombinant animal virus vector encoding p55-IC, portions thereof, analogs and derivatives of all of the aforegoing, and a protein capable of binding a cell surface protein on the cells to be treated;

(ii) a pharmaceutical composition for the treatment of tumor cells, administration of said composition leading to the induction of IL-8 expression, and subsequent killing of the tumor cells.

As yet another aspect, the present invention provides a soluble, oligomeric tumor necrosis factor receptor (TNF-R) comprising at least two self-associated fusion proteins, each fusion protein having (a) at its one end, a TNF binding domain selected from the extracellular domain of a TNF-R, analogs or derivatives thereof, said extracellular domain, analogs or derivatives thereof being incapable of deleterious self-association and being able to bind TNF; and (b) at its other end, a self-associating domain selected from (i) essentially all of the intracellular domain of the p55 TNF-R (p55-IC), extending from about amino acid residue 206 to about amino acid residue 426 of the native p55 TNF-R molecule (p55-R, SEQ ID NO:37); (ii) the death domain of the p55-IC extending from about amino acid residue 328 to about amino acid residue 426 of the native p55-R (SEQ ID NO:37); (iii) essentially all of the intracellular domain of the FAS/APO1 receptor (FAS-IC); (iv) the death domain of FAS-IC; and (v) analogs, fractions or derivatives of any one of (i)–(iv) being capable of self-association, wherein said at least two self-associated proteins self-associate only at said ends (b) having said ends (a) capable of binding to at least two TNF monomers, each end (a) capable of binding one TNF monomer; and salts and functional derivatives of said soluble, oligomeric TNF-R.

Embodiments of this aspect of the invention include all of the above combinations of ends (a) with ends (b) as defined above, for example, a soluble, oligomeric TNF-R comprising as extracellular domain, the p55-R extracellular domain and as self-associating intracellular domain, the p55-IC.

Moreover, there is also provided a process for producing the soluble oligomeric TNF-R of the invention comprising:

(a) the construction of an expression vector encoding any one of said fusion proteins, the DNA sequence of each of said ends of the fusion protein being obtained from cloned DNA sequences encoding essentially all of said extracellular domain of the TNF-R, analogs or derivatives thereof; and from cloned DNA sequences encoding essentially all of said p55-IC, p55-IC death domain, FAS-IC, FAS-IC death domain, analogs or derivatives of all of the aforegoing, said ends being ligated together to form a fusion protein sequence, and said fusion protein sequence being inserted into said vector under the control of transcriptional and translational regulatory sequences;

(b) introduction of the vector of (a) into a suitable host cell in which said fusion protein is expressed; and (c) purification of the fusion protein expressed in said host cells, said fusion protein self-associating prior to, during, or following the purification process to yield a soluble, oligomeric TNF-R.

Furthermore, there is also provided a vector encoding the above fusion proteins, useful in the above method of the invention; host cells containing the vector; as well as a pharmaceutical composition comprising the soluble, oligomeric TNF-R, salts or functional derivatives thereof and mixtures of any of the aforegoing according to the invention, as active ingredient, together with a pharmaceutically acceptable carrier. Similarly, the soluble, oligomeric TNF-R, salts, functional derivatives thereof and mixtures of any of the aforegoing, according to the invention, are provided for use in antagonizing the deleterious effect of TNF in mammals, especially in the treatment of conditions wherein an excess of TNF is formed endogenously or is exogenously administered; or alternatively, for use in maintaining prolonged beneficial effects of TNF in mammals when used with TNF exogenously administered.

Along the lines set forth concerning the above aspect of the invention, it has also been discovered that it is possible to construct a soluble, oligomeric FAS/APO1 receptor (FAS-R) which is useful for antagonizing the deleterious effects of the FAS ligand. Accordingly, in a further aspect, the present invention provides a soluble, oligomeric FAS/APO1 receptor (FAS-R) comprising at least two self-associated fusion proteins, each fusion protein having (a) at its one end, a FAS ligand binding domain selected from the extracellular domain of a FAS-R, analogs or derivatives thereof being incapable of self-associating and being able to bind FAS ligand; and (b) at its other end, a self-associating domain selected from (i) essentially all of the intracellular domain of the p55 TNF-R (p55-IC), extending from about amino acid residue 206 to about amino acid residue 426 of the native p55 TNF-R molecule (p55-R; SEQ ID NO:37); (ii) the death domain of the p55-IC extending from about amino acid residue 328 to about amino acid residue 426 of the native p55-R (SEQ ID NO:37); (iii) essentially all of the intracellular domain of the FAS/APO1 receptor (FAS-IC); (iv) the death domain of FAS-IC; and (v) analogs or derivatives of any one of (i)–(iv) being capable of self-association, wherein said at least two self-associated proteins only self-associate at said ends (b) having said ends (a) capable of binding to at least two FAS ligand monomers, each end (a) capable of binding one FAS ligand monomer; and salts and functional derivatives of said soluble, oligomeric FAS-R.

In accordance with this aspect of the invention, there is also provided a process for the production of the soluble, oligomeric FAS-R comprising:

(a) the construction of an expression vector encoding any one of said fusion proteins, the DNA sequence of each of said ends of the fusion protein being obtained from cloned DNA sequences encoding essentially all of said extracellular domain of the FAS-R, analogs or derivatives thereof; and from cloned DNA sequences encoding essentially all of said p55-IC, p55-IC death domain, FAS-IC, FAS-IC death domain, analogs or derivatives thereof of all the aforegoing, said ends being ligated together to form a fusion protein sequence, and said fusion protein sequence being inserted into said vector under the control of transcriptional and translational regulatory sequences;

(b) introduction of the vector of (a) into a suitable host cell in which said fusion protein is expressed; and (c) purification of the fusion protein expressed in the host cells, said fusion protein self-associating prior to, during, or following the purification process to yield a soluble, oligomeric FAS-R.

Moreover, also provided are an expression vector containing the fusion protein sequence encoding the soluble oligomeric FAS-R, useful in the above process; host cells containing the vector; and pharmaceutical compositions comprising the soluble, oligomeric FAS-R, salts or functional derivatives thereof or mixtures of any of the aforegoing as active ingredient together with a pharmaceutically acceptable carrier. Similarly, there is provided a soluble, oligomeric FAS-R, salts or functional derivatives thereof or mixtures of any of the aforegoing, for use in antagonizing the deleterious effect of FAS ligand in mammals, especially in the treatment of conditions wherein an excess of the FAS ligand is formed endogenously or is exogenously administered.

In a similar fashion to that noted above concerning the oligomeric TNF-Rs and oligomeric FAS-Rs, it is also possible to prepare mixed oligomers having binding specificity for both TNF and FAS-R ligand. Thus, the present invention also provides a mixed oligomeric TNF-R/FAS-R comprising at least two self-associated fusion proteins, one of which fusion proteins is selected from any one of the above mentioned TNF-specific fusion proteins, and the other fusion protein is selected from any one of the above mentioned FAS-R ligand-specific fusion proteins, to provide a mixed oligomer having at least one TNF-R extracellular domain and at least one FAS-R extracellular domain associated by virtue of the self-association between the intracellular domains or portions thereof fused to each of these extracellular domains. These mixed oligomeric receptors are prepared by preparing, as noted above, the oligomeric TNF-Rs and the oligomeric FAS-Rs and then mixing these together and subsequently selecting, by standard procedures, those oligomers having binding specificity for both FAS-R ligand and TNF. Another way for preparing the mixed oligomeric receptors is by co-transfecting suitable host cells with vectors, as noted above, encoding any of the TNF-specific fusion proteins (soluble TNF-Rs) and encoding any of the FAS-R ligand-specific fusion proteins (soluble FAS-Rs), purifying the expressed fusion proteins which self-associate prior to, during, or following the purification to yield oligomeric receptors, and then selecting by standard procedures, those oligomeric receptors which are capable of binding to both TNF and FAS-R ligand.

Likewise, there is also provided pharmaceutical compositions comprising the mixed oligomeric receptors, salts or functional derivatives thereof or mixtures of any of the aforegoing as active ingredient together with a pharmaceutically acceptable carrier. In addition, there is provided the mixed oligomeric receptors, salts or functional derivatives thereof or mixtures of any of the aforegoing, for use in antagonizing the deleterious effects of both TNF and FAS-R ligand in mammals, especially in the treatment of conditions wherein an excess of TNF and FAS-R ligand is formed endogenously or is exogenously administered; or alternatively, for use in maintaining prolonged (slow-release) beneficial effects of TNF and/or FAS-R ligand in mammals when used with TNF and/or FAS-R ligand (in soluble form) exogenously administered.

Other aspects and embodiments of the present invention are also provided as arising from the following detailed description of the invention.

It should be noted that, where used throughout, the following terms: "Modulation of the TNF-effect on cells" and "Modulation of the FAS-ligand effect on cells" are understood to encompass in vitro as well as in vivo treatment.

BRIEF DESCRIPTION OF THE DRAWINGS

FIGS. 1a–d depict schematically the partial and preliminary nucleotide sequence of cDNA clones encoding the p55IC and p75IC-binding proteins, and the deduced amino acid sequence of protein 55.1 wherein FIG. 1(a) is the sequence (SEQ ID NO:9) of clone 55.11 encoding the p55IC-binding protein 55.11; FIG. 1(b) is the partial and preliminary sequence (SEQ ID NOs:10 and 11) of clone 75.3 encoding the p75IC-binding protein 75.3; and FIG. 1(c) is the partial and preliminary sequence (SEQ ID NOs:12 and 13) of clone 75.16 encoding the p75IC-binding protein 75.16; all as described in Example 1; and FIG. 1(d) depicts the deduced amino acid sequence of protein 55.11 (SEQ ID NO:14), deduced from the nucleotide sequence of FIG. 1(a), as also described in Example 1.

FIG. 4 shows schematically a comparison of the deduced amino acid sequence of human 55.11 (SEQ ID NO:14) to related protein sequences derived from lower organisms, YHR027c (yeast; SEQ ID NO:15), SEN3 (yeast; SEQ ID NO:16), *A. thaliana* (plant; SEQ ID NO:17), and *C. elegans* (nematode, SEQ ID NO:18), as described in Example 1.

Figure 7:
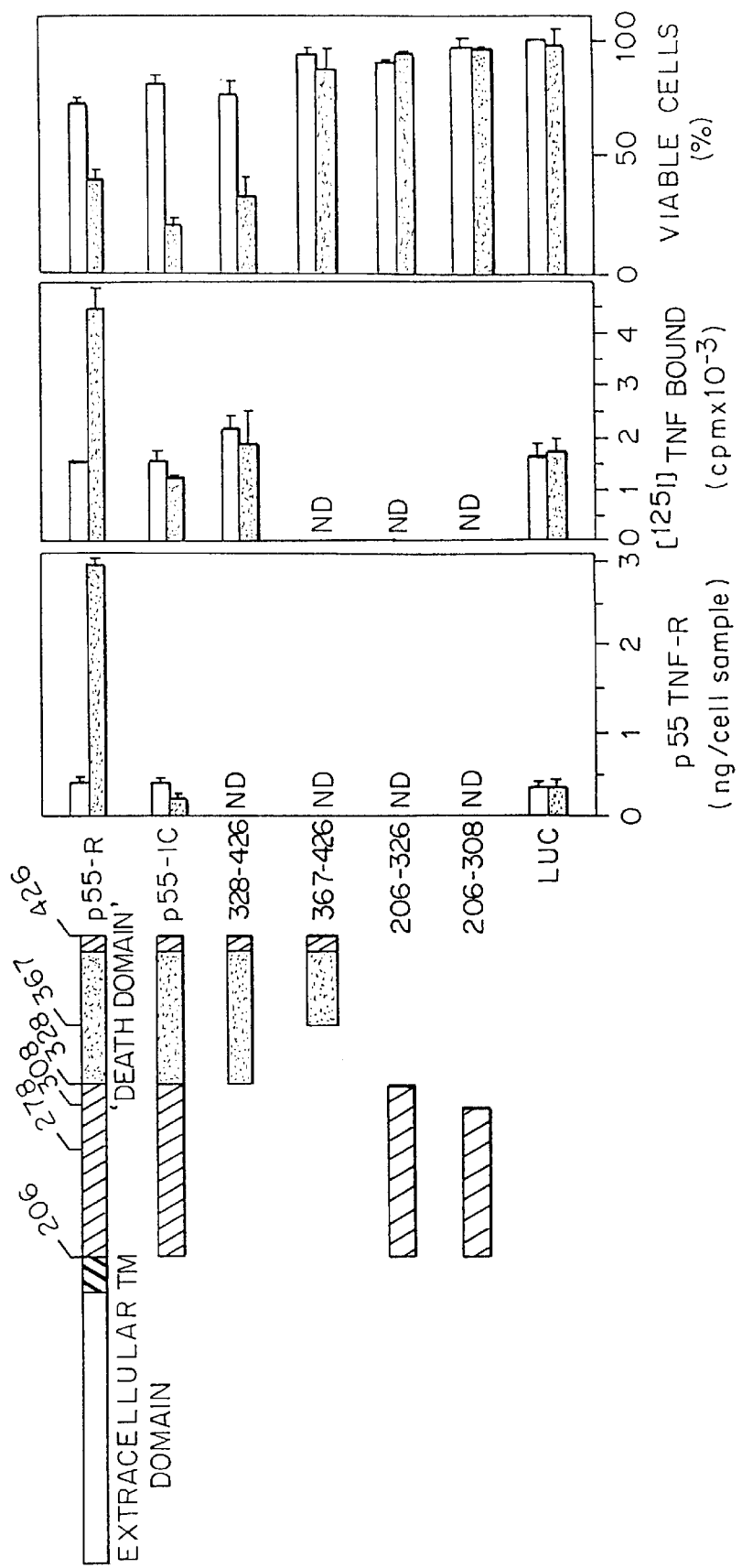
FIG. 7 depicts the ligand-independent triggering of the cytocidal effect in HeLa cells transfected with the full-length p55-R, its intracellular domain, or parts of the intracellular domain including the "death domain" where.

(i) at the extreme left hand side of FIG. 7 there is depicted schematically the various DNA molecules encoding the full-length p55-R, its intracellular domain and the portions of the intracellular domain which were inserted into the vector with which the HeLa cells were transfected.

(ii) the left and middle bar graphs show the TNF receptor expression in the HeLa cells of each of the types of receptor shown at the extreme left of FIG. 7, the left bar representing the amounts of receptor in ng/cell sample and the middle bar graph representing the amounts of receptor expressed in terms of radioiodinated TNF bound to the transfected cells; and (iii) the right bar graph showing the viability of the HeLa cells expressing the various kinds of the receptor;

and wherein in all of the bar graphs the open bars represent cells transfected in the presence of tetracy-cline and the closed bars represent cells transfected in the absence of tetracycline; all of the above being described herein in Example 2.

Figure 8A:
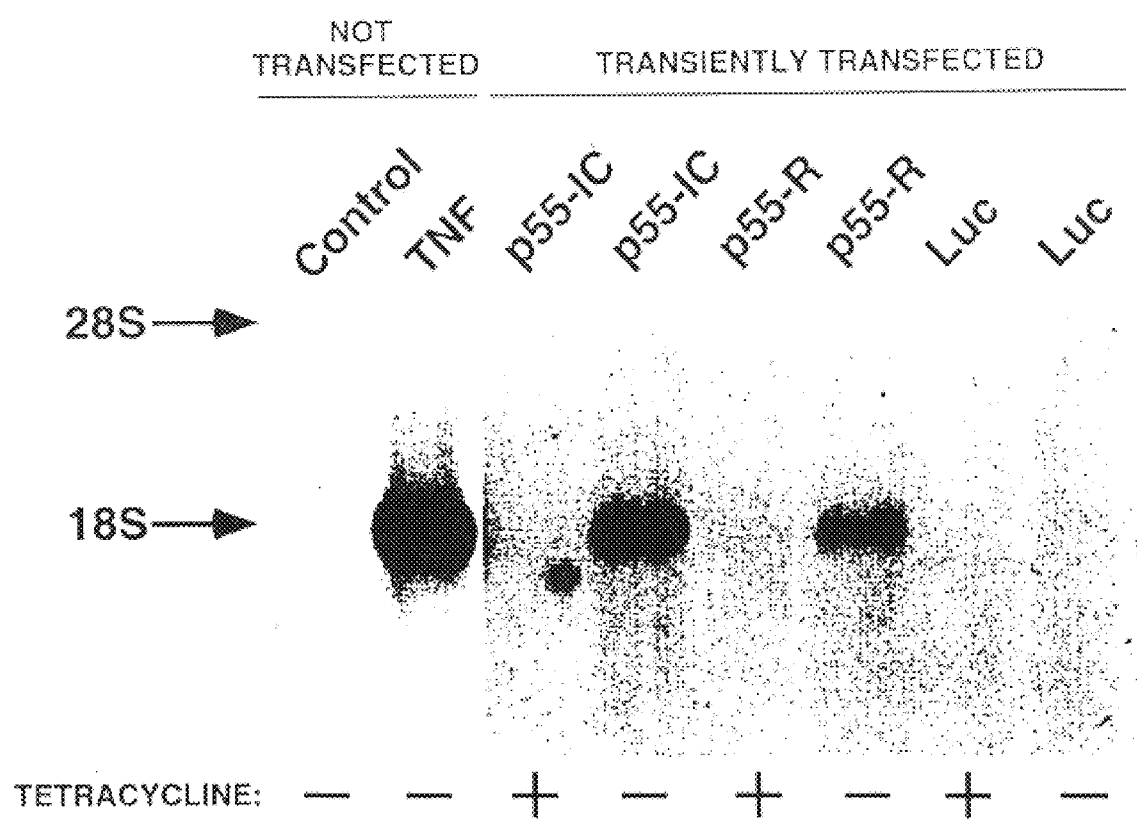
Figure 8B:

FIG. 8 depicts the ligand-independent induction of IL-8 gene expression in HeLa cells transfected with the full-length p55-R or its intracellular domain (p55IC), wherein in panel A there is shown a reproduction of a Northern blot representing the Northern analysis of RNA extracted from HeLa cells treated or untreated with TNF (two left hand lanes marked "control" and "TNF"), and of RNA extracted from HeLa cells transfected with vectors encoding the p55-R, p55-IC or the control protein, luciferase (the remaining lanes marked "p55-IC", "p55-R" and Luc, respectively), the cells having been transfected in the presence (+) or absence (−) of tetracycline in each case (hence two lanes per transfection); and wherein in panel B there is shown the methylene blue staining of 18S rRNA in each of the HeLa cell sample shown in panel A; all of the above being described in Example 2.

Figures 9A, 9B:
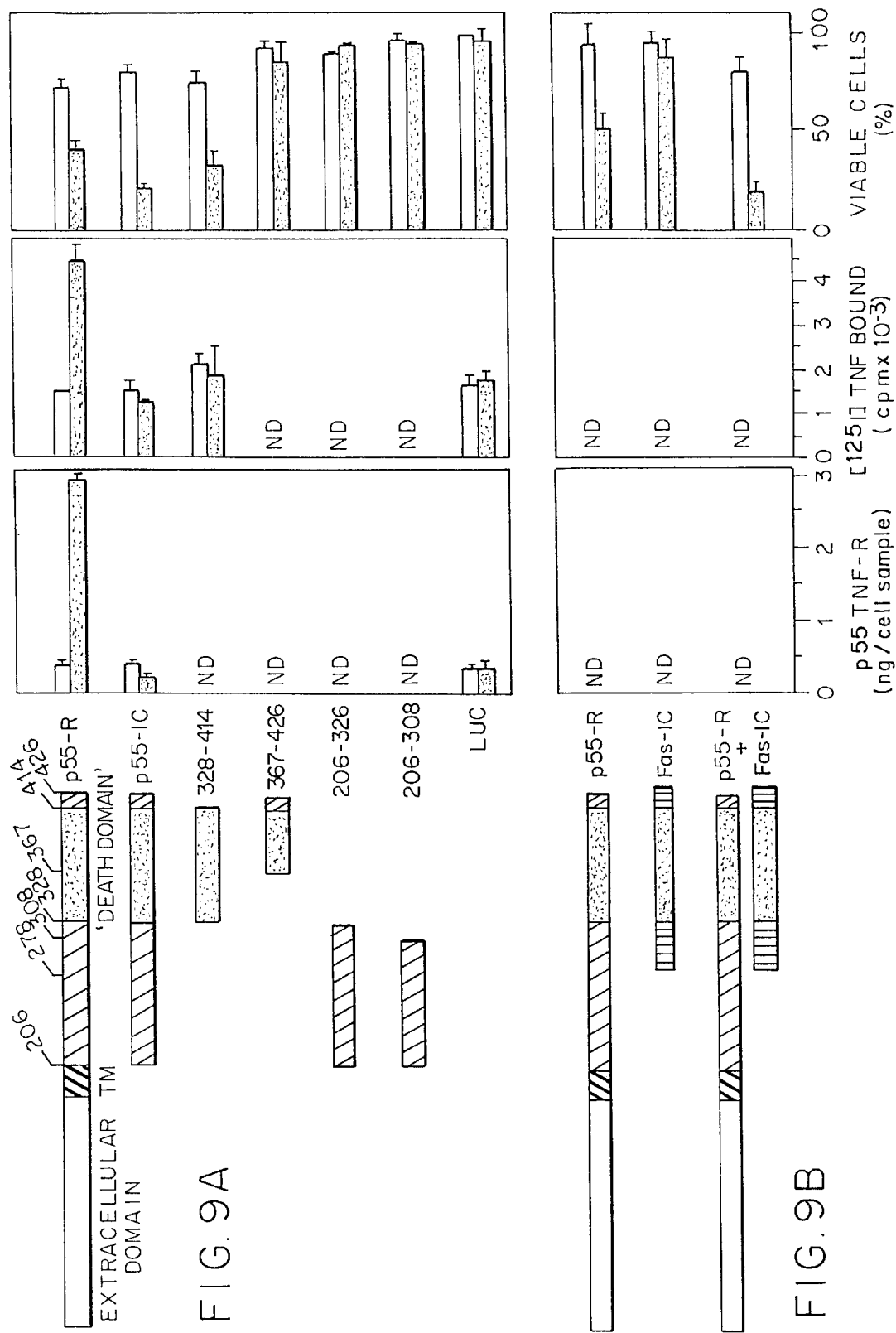

FIG. 9 (A and B) depicts graphically the ligand independent triggering of a cytocidal effect in HeLa cells transfected with p55R or parts thereof, or with FAS-IC, wherein in FIGS. 9A there is depicted the results with respect to the p55R or parts thereof and in FIG. 9B there is depicted the results with respect to the FAS-IC. In the left hand panels of both FIG. 9A and B there is depicted schematically the portion of the p55R or FAS-IC used in the transfections while the right hand panels depict graphically the experimental results, all as described in Example 2.

FIG. 10 depicts schematically the partial and preliminary nucleotide sequence (SEQ ID NOs:19 and 20) of a cDNA clone, called "F2", which encodes a protein capable of binding to the p55IC and FAS-IC, as described in Example 3.

FIG. 11 depicts schematically the partial and preliminary nucleotide sequence (SEQ ID NOs:21–23) of a cDNA clone, called F9, which encodes a protein capable of binding to the p55IC and FAS-IC, as described in Example 3.

FIG. 12 depicts schematically the partial and preliminary nucleotide sequence (SEQ ID NO:24) of a cDNA clone, called DD11, which encodes a protein capable of binding to the p55IC, especially the p55DD, and FAS-IC, as described in Example 3.

Figure 13:
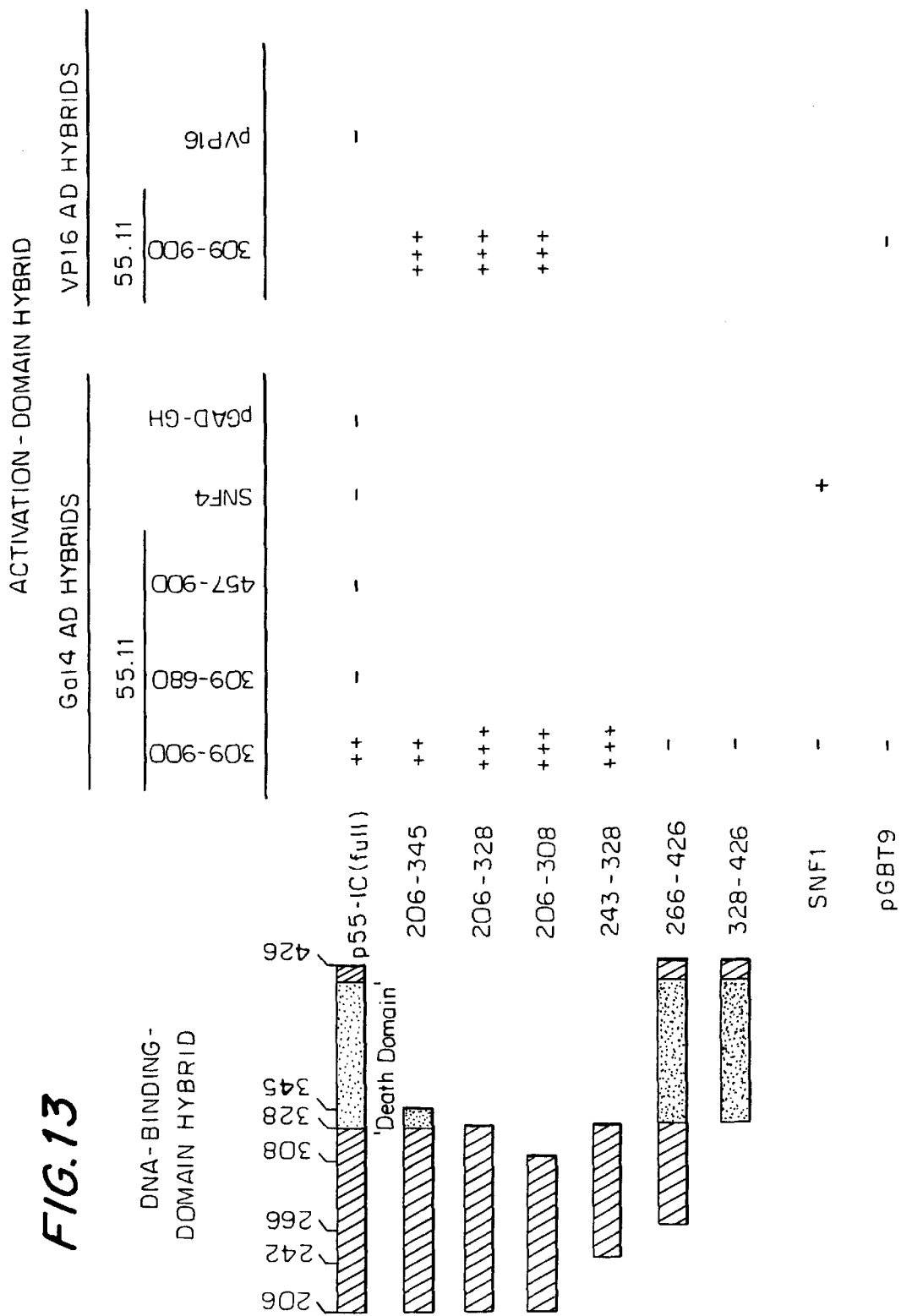

FIG. 13 is a table showing the binding of the 55.11 protein to p55-IC under transformed yeasts.

FIG. 14 is a table showing self-association of the intracellular domains of p55-R and FAS/APO1 within transformed yeasts. The assessment is by a two hybrid β-galactosidase expression test.

DETAILED DESCRIPTION OF THE INVENTION

The present invention relates, in one aspect, to novel proteins which are capable of binding to the intracellular domain of receptors belonging to the TNF/NGF superfamily, such as TNF-Rs and FAS-R and hence are considered as mediators or modulators of this superfamily of receptors, e.g. of the TNF-Rs and FAS-R, having a role in, for example, the signaling process that is initiated by the binding of TNF to the TNF-R and FAS ligand to FAS-R. Examples of these proteins are those which bind to the intracellular domain of the p55 TNF-R (p55IC), such as the proteins designated herein as 55.1, 55.3 and 55;11 (Example 1) as well as those encoded by cDNA clones F2, F9, DD11, 4, 65, 14v1, and 16v1 (Example 3); those which bind to the intracellular domain of the p75 TNF-R (p75IC), such as the proteins designated herein as 75.3 and 75.16 (Example 1), E3, E15, E19, and 230 (Example 3); and those which bind to the intracellular domain of FAS-R (FAS-IC), such as the proteins encoded by cDNA clones F2, F9 and DD11 (Example 3). Proteins 55.1 and 55.3 have been found to represent portions or fragments of the intracellular domain of the p55 TNF-R (p55IC); other proteins, 55.11, 75.3 and 75.16, represent proteins not described at all prior to the present invention (75.3, 75.16) or those that have been described (55.11, see Khan et al., 1992) but whose function and other characteristics, particularly, the ability to bind to a TNF-R, were not described in any way (see Example 1, below). The new proteins encoded by cDNA clones F2, F9 and DD11 as well as E15, E19, and 230 also represent proteins previously not described at all, i.e. their sequence is not in the "GENEBANK" or "PROTEIN BANK" data banks of DNA or amino acid sequences. The p75IC-binding protein E3 appears to be transcribed from a product of alternate splicing from a gene for HHR23A (Masutani et al., 1994).

Thus, the present invention concerns the DNA sequences encoding these proteins and the proteins encoded by these sequences.

Moreover, the present invention also concerns the DNA sequences encoding biologically active analogs and derivatives of these proteins, and the analogs and derivatives encoded thereby. The preparation of such analogs and derivatives is by standard procedure (see for example, Sambrook et al., 1989) in which in the DNA sequences encoding these proteins, one or more codons may be deleted, added or substituted by another, to yield analogs having at least a one amino acid residue change with respect to the native protein. Acceptable analogs are those which retain at least the capability of binding to the intracellular domain of the TNF/NGF receptor superfamily, such as FAS-R or TNF-R, e.g. the p55IC, p75IC or FAS-IC, or which can mediate any other binding or enzymatic activity, e.g. analogs which bind the p55, p75IC or FAS-IC but which do not signal, i.e. do not bind to a further downstream receptor, protein or other factor, or do not catalyze a signal-dependent reaction. In such a way analogs can be produced which have a so-called dominant-negative effect, namely, an analog which is defective either in binding to the, for example, p55IC, p75IC or FAS-IC, or in subsequent signaling following such binding. Such analogs can be used, for example, to inhibit the TNF- or FAS-ligand-effect by competing with the natural IC-binding proteins. Likewise, so-called dominant-positive analogs may be produced which would serve to enhance, for example, the TNF or FAS ligand effect. These would have the same or better IC-binding properties and the same or better signaling properties of the natural IC-binding proteins. Similarly, derivatives may be prepared by standard modifications of the side groups of one or more amino acid residues of the proteins, or by conjugation of the proteins to another molecule e.g. an antibody, enzyme, receptor, etc., as are well known in the art.

The new TNF-R and FAS-R intracellular domain-binding proteins, e.g. the proteins 55.1, 55.3, 55.11, 75.3, 75.16, E3, E15, E19, 230 as well as the proteins encoded by cDNA clones F2, F9, DD11, 4, 65, 14v1 and 16v1 (hereinafter, F2, F9, DD11, 4, 65, 14v1, 16v1) have a number of possible uses, for example:

(i) They may be used to mimic or enhance the function of TNF or FAS-R ligand, in situations where an enhanced TNF or FAS-R ligand effect is desired such as in anti-tumor, anti-inflammatory or anti-HIV applications where the TNF- or FAS-R ligand-induced cytotoxicity is desired. In this case the proteins, e.g. those binding to the p55IC such as 55.1, 55.3, as well as F2, F9, DD11, 4, 65, 14v1, 16v1 and the free p55IC itself (see below and Example 2), as well as the "death domain" of the p55IC (p55DD), which enhance the TNF effect; or proteins F2, F9 and DD11 as well as FAS-IC and FAS-DD which enhance the FAS-R ligand effect, i.e. cytotoxic effect, may be introduced to the cells by standard procedures known per se. For example, as the proteins are intracellular and it is desired that they be introduced only into the cells where the TNF or FAS-R ligand effect is wanted, a system for specific introduction of these proteins into the cells is necessary. One way of doing this is by creating a recombinant animal virus e.g. one derived from Vaccinia, to the DNA of which the following two genes will be introduced: the gene encoding a ligand that binds to cell surface proteins specifically expressed by the cells e.g. ones such as the AIDS (HIV) virus gp120 protein which binds specifically to some cells (CD4 lymphocytes and related leukemias) or any other ligand that binds specifically to cells carrying a TNF-R or FAS-R, such that the recombinant virus vector will be capable of binding such TNF-R- or FAS-R-carrying cells; and the gene encoding the new intracellular domain-binding protein or the p55IC, p55DD, FAS-IC or FAS-DD protein. Thus, expression of the cell-surface-binding protein on the surface of the virus will target the virus specifically to the tumor cell or other TNF-R- or FAS-R-carrying cell, following which the intracellular domain-binding protein encoding sequence or p55IC, p55DD, FAS-IC or FAS-DD encoding sequence will be introduced into the cells via the virus, and once expressed in the cells will result in enhancement of the TNF or FAS-R ligand effect leading to the death of the tumor cells or other TNF-R- or FAS-R-carrying cells it is desired to kill. Construction of such recombinant animal virus is by standard procedures (see for example, Sambrook et al., 1989). Another possibility is to introduce the sequences of the new proteins or the p55IC, p55DD, FAS-IC or FAS-DD in the form of oligonucleotides which can be absorbed by the cells and expressed therein.

(ii) They may be used to inhibit the TNF or FAS-R ligand effect, e.g. in cases such as tissue damage in septic shock, graft-vs.-host rejection, or acute hepatitis, in which case it is desired to block the TNF-induced TNF-R or FAS-R ligand induced FAS-R intracellular signaling. In this situation it is possible, for example, to introduce into the cells, by standard procedures, oligonucleotides having the anti-sense coding sequence for these new proteins, or the anti-sense coding sequence for p55IC, p55DD, FAS-IC or FAS-DD, which would effectively block the translation of mRNAs encoding these proteins and thereby block their expression and lead to the inhibition of the TNF- or FAS-R ligand-effect.

Such oligonucleotides may be introduced into the cells using the above recombinant virus approach, the second sequence carried by the virus being the oligonucleotide sequence. Another possibility is to use antibodies specific for these proteins to inhibit their intracellular signaling activity. It is possible that these new proteins have an extracellular domain as well as an intracellular one, the latter which binds to the TNF-R or FAS-R binding domain, and thus antibodies generated to their extracellular domains can be used to block their TNF- or FAS-R ligand-related functions.

Yet another way of inhibiting the TNF or FAS-R ligand effect is by the recently developed ribozyme approach. Ribozymes are catalytic RNA molecules that specifically cleave RNAs. Ribozymes may be engineered to cleave target RNAs of choice, e.g. the mRNAs encoding the new proteins of the invention or the mRNA encoding the p55IC, p55DD, FAS-IC or FAS-DD. Such ribozymes would have a sequence specific for the mRNA of choice and would be capable of interacting therewith (complementary binding) followed by cleavage of the mRNA, resulting in a decrease (or complete loss) in the expression of the protein it is desired to inhibit, the level of decreased expression being dependent upon the level of ribozyme expression in the target cell. To introduce ribozymes into the cells of choice (e.g. those carrying TNF-Rs or FAS-R) any suitable vector may be used, e.g. plasmid, animal virus (retrovirus) vectors, that are usually used for this purpose (see also (i) above, where the virus has, as second sequence, a cDNA encoding the ribozyme sequence of choice). Moreover, ribozymes can be constructed which have multiple targets (multi-target ribozymes) that can be used, for example, to inhibit the expression of one or more of the proteins of the invention and/or the p55IC, p55DD, FAS-IC or FAS-DD as well (For reviews, methods etc. concerning ribozymes see Chen et al., 1992; Zhao and Pick, 1993; Shore et al., 1993; Joseph and Burke, 1993; Shimayama et al., 1993; Cantor et al., 1993; Barinaga, 1993; Crisell et al., 1993 and Koizumi et al., 1993).

(iii) They may be used to isolate, identify and clone other proteins which are capable of binding to them, e.g. other proteins involved in the intracellular signaling process that are downstream of the TNF-R or FAS-R intracellular domain. In this situation, these options, namely, the DNA sequences encoding them may be used in the yeast two-hybrid system (see Example 1, below) in which the sequence of these proteins will be used as "baits" to isolate, clone and identify from cDNA or genomic DNA libraries other sequences ("preys") encoding proteins which can bind to these new TNF-R or FAS-R intracellular domain-binding proteins. In the same way, it may also be determined whether the specific proteins of the present invention, namely, those which bind to the $p^{55}IC$, p75IC, or FAS-IC, can bind to other receptors of the TNF/NGF superfamily of receptors. For example, it has recently been reported (Schwalb et al., 1993; Baens et al., 1993; Crowe et al., 1994) that there exist other TNF-Rs besides the p55 and p75 TNF-Rs. Accordingly, using the yeast two-hybrid system it may be specifically tested whether the proteins of the present invention are capable of specifically binding to these other TNF-Rs or other receptors of the TNF/NGF superfamily. Moreover, this approach may also be taken to determine whether the proteins of the present invention are capable of binding to other known receptors in whose activity they may have a functional role.

(iv) The new proteins may also be used to isolate, identify and clone other proteins of the same class i.e. those binding to TNF-R or FAS-R intracellular domains or to functionally related receptors, and involved in the intracellular signaling process. In this application the above noted yeast two-hybrid system may be used, or there may be used a recently developed (Wilks et al., 1989) system employing non-stringent southern hybridization followed by PCR cloning. In the wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequences of the new proteins to identify and clone those of related TNF-R, FAS-R or related receptor (TNF/NGF superfamily receptors) intracellular domain-binding proteins.

(v) Yet another approach to utilizing the new proteins of the invention is to use them in methods of affinity chromatography to isolate and identify other proteins or factors to which they are capable of binding, e.g. other receptors related to TNF-Rs (TNF/NGF receptor superfamily) or other proteins or factors involved in the intracellular signaling process. In this application, the proteins of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the new proteins of the invention, can be eluted, isolated and characterized.

(vi) As noted above, the new proteins of the invention may also be used as immunogens (antigens) to produce specific antibodies thereto. These antibodies may also be used for the purposes of purification of the new proteins either from cell extracts or from transformed cell lines producing them. Further, these antibodies may be used for diagnostic purposes for identifying disorders related to abnormal functioning of the TNF or FAS-R ligand system, e.g. overactive or underactive TNF- or FAS-R ligand-induced cellular effects. Thus, should such disorders be related to a malfunctioning intracellular signaling system involving the new proteins, such antibodies would serve as an important diagnostic tool.

It should also be noted that the isolation, identification and characterization of the new proteins of the invention may be performed using any of the well known standard screening procedures. For example, one of these screening procedures, the yeast two-hybrid procedure as is set forth in the following examples (Examples 1 and 3), was used to identify the new proteins of the invention. Likewise as noted above and below, other procedures may be employed such as affinity chromatography, DNA hybridization procedures, etc. as are well known in the art, to isolate, identify and characterize the new proteins of the invention or to isolate, identify and characterize additional proteins, factors, receptors, etc. which are capable of binding to the new proteins of the invention or to the receptors belonging to the TNF/NGF family of receptors.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature,* 256:495–497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene publishing Assoc. and Wiley Interscience N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066–1074 (1986); Robinson et al., International Patent Application No. WO8702671 (published May 7, 1987); Liu et al., *Proc. Natl. Acad. Sci USA* 84:3439–3443 (1987); Sun et al., *Proc. Natl. Acad. Sci USA* 84:214–218 (1987); Better et al., *Science* 240:1041–1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the IC-binding proteins, analogs or derivatives thereof, of the present invention or the p55IC, p55DD, FAS-IC, FAS-DD, analogs or derivatives thereof may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above IC-binding proteins, analogs or derivatives or p55IC, p55DD, FAS-IC or FAS-DD, analogs or derivatives.

The anti-Id mAbs thus have their own idiotypic epitopes, or "idiotopes" structurally similar to the epitope being evaluated, such as GRB protein-α.

The term "antibody" is also meant to include both intact molecules as well as fragments thereof, such as, for example, Fab and F(ab")$_2$, which are capable of binding antigen. Fab and F(ab")$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab")$_2$ and other fragments of the antibodies useful in the present invention may be used for the detection and quantitation of the IC-binding proteins or p55IC, p55DD, FAS-IC or FAS-DD according to the methods disclosed herein for intact antibody molecules. Such fragments are typically produced by proteolytic cleavage, using enzymes such as papain (to produce Fab fragments) or pepsin (to produce F(ab")$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the IC-binding proteins or p55IC, p55DD, FAS-IC, FAS-DD in a sample or to detect presence of cells which express the IC-binding proteins of the present invention or the p55IC, p55DD, FAS-IC, FAS-DD proteins. This can be accomplished by immunofluorescence techniques employing a fluorescently labeled antibody (see below) coupled with light microscopic, flow-cytometric, or fluorometric detection.

The antibodies (or fragments thereof) useful in the present invention may be employed histologically, as in immunofluorescence or immunoelectron microscopy, for in situ detection of IC-binding proteins of the present invention or the p55IC, p55DD, FAS-IC, FAS-DD. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the IC-binding proteins or the p55IC, p55DD, FAS-IC, FAS-DD, but also its distribution on the examined tissue. Using the present invention, those of ordinary skill will readily perceive that any of wide variety of histological methods (such as staining procedures) can be modified in order to achieve such in situ detection.

Such assays for IC-binding proteins of the present invention or the p55IC, p55DD, FAS-IC, FAS-DD, typically comprises incubating a biological sample, such as a biological fluid, a tissue extract, freshly harvested cells such as lymphocytes or leukocytes, or cells which have been incubated in tissue culture, in the presence of a detectably labeled antibody capably of identifying the IC-binding proteins or the p55IC, p55DD, FAS-IC, FAS-DD, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrin, pyocyanin, allopyocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and the contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncompleted labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The new proteins of the invention once isolated, identified and characterized by any of the standard screening procedures, for example, the yeast two-hybrid method, affinity chromatography, and any other well known method known in the art, may then be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs and derivatives, and thus the vectors encoding them also include vectors encoding analogs of these proteins, and the transformed hosts include those producing such analogs. The derivatives of these proteins are the derivatives produced by standard modification of the proteins or their analogs, produced by the transformed hosts.

In another aspect, the invention relates to the use of the free intracellular domain of the p55 TNF-R (p55IC) or FAS-R (FAS-IC) or their so-called "death domains" (p55DD or FAS-DD, respectively) as an agent for enhancing the TNF or FAS-R ligand effect on cells, on its own (see Example 2). Where it is desired to introduce a TNF- or FAS-R-ligand-induced cytotoxic effect in cells, e.g. cancer cells or HIV-infected cells, the p55IC, p55DD, FAS-IC or FAS-DD can be introduced into such cells using the above noted (see (i) above) recombinant animal virus (e.g. vaccinia) approach. Here too, the native p55IC, p55DD, FAS-IC or FAS-DD, biologically active analogs and derivatives or fragments may be used, all of which can be prepared as noted above.

Likewise, the present invention also relates to the specific blocking of the TNF-effect or FAS-R ligand-effect by blocking the activity of the p55IC, p55DD, FAS-IC or FAS-DD, e.g. anti-sense oligonucleotides may be introduced into the cells to block the expression of the p55IC, p55DD, FAS-IC or FAS-DD.

The present invention also relates to pharmaceutical compositions comprising recombinant animal virus vectors encoding the TNF-R or FAS-R intracellular domain binding proteins (including the p55IC, p55DD, FAS-IC and FAS-DD), which vector also encodes a virus surface protein capable of binding specific target cell (e.g. cancer cells) surface proteins to direct the insertion of the intracellular domain binding protein sequences into the cells.

In another aspect, the present invention also concerns, specifically, the effects of the self-associating intracellular domain of the p55 TNF receptor (p55-IC, see Example 2).

An example of such effects, which is an effect normally mediated by TNF binding to its receptor and which is mimicked by the signaling activity of the self-associating p55-IC or parts thereof, is the induction of expression of the gene encoding IL-8.

IL-8 is a cytokine belonging to the subclass of chemokines having primarily chemotactic activity, and has been shown to play a major role in the chemotaxis of granulocytes and other cell types associated with a number of pathological states (see for example, Endo et al., 1994; Sekido et al., 1993; Harada et al., 1993; Ferrick et al., 1991).

TNF has a beneficial activity, and is used as such, in treatments to destroy tumor cells and virus infected cells or to augment antibacterial activities of granulocytes. However, as noted above, TNF also has undesirable activities in which case it is desired to block its activity, including those situations where large doses of TNF are used in cancer therapy, antiviral therapy or antibacterial therapy.

Accordingly, it is desirable to be able to direct TNF or a substance capable of mimicking its beneficial activity to the cells or tissues that it is specifically desired to treat.

In accordance with the present invention it has been found that the self-associating intracellular domain of the p55-R (p55-IC) can, in a ligand-independent manner, mimic a number of effects of TNF, e.g. the "death domain" of p55-IC can induce cytotoxic effects on cells, and that the p55-IC can induce IL-8 gene expression. Thus, it is possible to utilize the p55-IC to mimic TNF function in a site-directed fashion, i.e. to introduce the p55-IC only to those cells or tissues it is desired to treat.

One example of the above approach, as mentioned above, is to specifically transfect (transform) tumor cells or malignant tissue with a DNA molecule encoding p55-IC or a portion thereof which can induce not only cytotoxic effects on such cells or tissue but also augment these effects by the co-induction of IL-8, which will result in the accumulation at the site of these cells or tissue of granulocytes and other lymphocytes, which, in turn, will serve to destroy the tumor cells or tissue. This approach obviates the need for administration of large doses of TNF with its associated deleterious side-effects.

Using conventional recombinant DNA technology, it is possible to prepare various regions of the p55-IC and to determine which region is responsible for each TNF-induced effect, e.g. we have determined that the "death domain" is responsible for cytotoxicity (Example 2), and we have already prepared various other constructs containing portions of the p55-IC, which portions (together with part or all of the death domain) may be responsible for other TNF-effects, and which may be used in a ligand-independent manner, once self-associated for activity, to induce these effects, e.g. IL-8 induction.

It should be noted that the sequence of the p55-IC involved in the induction of other TNF-associated effects (e.g. IL-8 induction) may be different to that involved in cytotoxicity, i.e. may include none or only part of the "death domain" and have other sequence motifs from other regions of the intracellular domain, or may be the same sequence, different features of the sequence (same sequence motif) being involved in the induction of different effects.

Accordingly, as detailed above and below, expression vectors containing these p55-IC portions, analogs or derivatives thereof may be prepared, expressed in host cells, purified and tested for their activity. In this way, a number of such p55-IC fragments having one or more TNF-associated activities may be prepared and used in a differential fashion for the treatment of any number of pathological conditions, e.g. viral infections, bacterial infections, tumors, etc. In all of these situations the specific activity can be augmented by incorporation (or co-transfection) with the p55-IC fragment responsible for IL-8 gene expression induction, permitting the desirable IL-8 chemotactic activity to enhance the destruction of the cells or tissues it is desired to destroy.

Thus, without administering systemically TNF, it is possible to induce its desirable effects by specifically introducing all or part of the p55-IC into the cells or tissues it is desired to treat.

The p55-IC may be introduced specifically into the cells or tissues it is wished to destroy by any one of the above-mentioned procedures. For example, one way of doing this is by creating a recombinant animal virus e.g. one derived from Vaccinia, to whose DNA the following two genes will be introduced: the gene encoding a ligand that binds to cell surface proteins specifically expressed by the cells e.g. ones such as the AIDS virus gp120 protein which binds specifically to some cells (CD4 lymphocytes and related leukemias) or any other ligand that binds specifically to cells carrying a TNF-R, such that the recombinant virus vector will be capable of binding such TNF-R-carrying cells; and the gene encoding the p55-IC or a portion thereof. Thus, expression of the cell-surface-binding protein on the surface of the virus will target the virus specifically to the tumor cell or other TNF-R-carrying cell, following which the p55-IC, or portion thereof, encoding sequence will be introduced into the cells via the virus, and once expressed in the cells will result in enhancement of the TNF effect leading to the death of the tumor cells or other TNF-R-carrying cells it is desired to kill or induction, for example, of IL-8 which will lead to cell death. Construction of such recombinant animal virus is by standard procedures (see for example, Sambrook et al., 1989). Another possibility is to introduce the sequences of the p55-IC or parts thereof in the form of oligonucleotides which can be absorbed by the cells and expressed therein.

The present invention thus also relates specifically to pharmaceutical compositions comprising the above recombinant animal virus vectors encoding the p55-IC or portions thereof, which vector also encodes a virus surface protein capable of binding specific target cell (e.g. cancer cells) surface proteins to direct the insertion of the p55-IC, or portions thereof, sequence into the cells.

The present invention relates, in yet another aspect, to new synthetic TNF receptors which are soluble and capable of oligomerization to form dimeric, and possibly also high order multimeric, TNF receptor molecules, each monomeric part of these receptors being capable of binding to a TNF monomer. TNF occurs naturally as a homotrimer containing three, active TNF monomers, each capable of binding to a single TNF receptor molecule, while TNF receptors occur naturally as monomers each capable of binding only one of the monomers of the TNF homotrimeric molecule. Thus, when TNF binds to TNF receptors on the cell surface, it is capable of binding to three receptor molecules resulting in the clustering of the TNF receptors, which is believed to be the start of the signaling process which ultimately triggers the observed TNF effects on the cells.

While TNF has many desirable effects such as its ability to destroy, for example, tumor cells or virus-infected cells and to augment antibacterial activities of granulocytes, TNF does however, have many undesirable effects such as, for example, in many severe diseases including autoimmune disorders, rheumatoid arthritis, graft-versus-host reaction (graft rejection), septic shock, TNF has been implicated as the major cause for pathological tissue destruction. TNF may also cause excessive loss of weight (cachexia) by suppressing the activities of adipocytes. Moreover, even when administered for its desirable activities, e.g. in the treatment of various malignant or viral diseases, the dosages of TNF used are often high enough to cause within the patient a number of undesirable cytotoxic side-effects, e.g. the destruction of healthy tissue.

Accordingly, in all of the above instances where TNF action is undesirable, an effective inhibitor of TNF has been sought. Many TNF-blocking agents have been proposed, including soluble proteins capable of binding TNF and inhibiting its binding to its receptors and hence also inhibiting the cytotoxic effects of TNF (see EP 308378, EP 398327 and EP 568925). However, these TNF binding proteins, or soluble TNF receptors are monomeric, each binding only one of the TNF monomers of the TNF homotrimer. Hence, the blocking of the TNF function may not be complete, each monomeric receptor-bound TNF molecule still having two TNF monomers free to be able to bind cell-surface TNF receptors and illicit its effects on the cells.

In order to overcome the above drawbacks in blocking TNF function, there has been developed in accordance with the present invention a means for constructing, as fusion proteins, soluble oligomeric TNF receptors which are capable of binding at least two TNF monomers of the naturally occurring TNF homotrimer molecule. As a consequence, these soluble oligomeric TNF receptors bind more avidly to their TNF ligand than the previously known monomeric soluble TNF binding proteins or receptors. For example, when the soluble TNF receptor of the invention is in the form of a dimer, it is capable of binding two TNF monomers of a TNF trimer and hence causes a more complete neutralization of the TNF, this neutralization being more sustained because of a lower dissociation rate of the dimeric soluble receptors from the TNF. Moreover, such soluble, oligomeric receptors are also larger than their monomeric counterparts and thus, pharmaceutically, they are also advantageous because of the likelihood of their having a slower clearance rate from the body.

The basis for the development of the soluble oligomeric TNF receptors of the invention, was the discovery that the intracellular domain of the p55-R TNF receptor was capable of self-association, and further, that within this intracellular domain (p55-IC) there exists a region, the so-called "death domain", which is also capable of self-association and as such, in a ligand-independent fashion, can cause cytotoxic effects on cells (see Example 2). Utilizing this self-association property of the p55-IC and its "death domain" it is thus possible to construct a fusion protein, using standard recombinant DNA technology, containing essentially all of the extracellular domain of a TNF receptor such as the p75-R or p55-R receptors, preferably the p55-R, and fused thereto, essentially all of the intracellular domain (p55-IC) or the death domain of the p55-IC. In this way a new fusion product is produced which has at one end the TNF binding domain i.e., the extracellular domain of the receptor, and at its other end the intracellular domain or the death domain thereof which is capable of self-association. Accordingly, such a product can oligomerize by self-association between two (and possible more) p55-IC or death domains thereof to yield oligomers (or at least dimers) having at least two TNF binding domains.

Furthermore, it has also been discovered in accordance with the present invention, that the FAS/APO1 receptor has a self-associating, intracellular domain inclusive of a self-associating "death domain" having certain homology to the p55-IC and death domain thereof (Example 2). Accordingly, it is possible to construct the soluble, oligomeric TNF receptors of the invention by fusing the extracellular domain of the TNF receptor (as noted above) to the intracellular domain or the "death domain" of the FAS/APO1 receptor.

In both of the above noted situations, the oligomeric TNF receptors of the invention are soluble by virtue of having only the soluble extracellular domain of the TNF receptor and the soluble intracellular domain or death domain thereof of either the p55-R TNF receptor or the FAS/APO1 receptor, i.e. they do not contain the transmembranal (insoluble) domain of either type of receptor.

The construction of the above oligomeric TNF receptors of the invention is detailed herein below in Example 4. It should however be noted that upon construction of the oligomeric TNF receptors of the invention, there may arise a situation, heretofore not reported, that the extracellular domain of the TNF receptor is capable of self-association, a situation that may not be desirable as it could interfere with the ability of the oligomeric receptor to bind to two or more TNF monomers of the TNF homotrimeric molecules or may lead to less than optimal binding of such TNF monomers. Accordingly, in such a situation, it is possible, by standard recombinant DNA procedures, to modify the extracellular domain of the TNF receptor by, for example, deleting or substituting one or more amino acid residues contained within the self-associating region to prevent such self-association. Such modifications of the extracellular domain of the TNF receptor are thus also part of the present invention and are designated herein as analogs or derivatives of the extracellular domain of the TNF receptor. In a similar fashion, the self-associating intracellular domain (IC) or death domain (DD) thereof of the p55-R receptor or the FAS/APO1 receptor used in the oligomeric TNF receptors of the invention, may also be analogs or derivatives thereof i.e. may be any modification of the p55-IC sequence or portions thereof including the death domain (p55DD) or any modification of the FAS/APO1 intracellular domain (FAS-IC) sequence or portions thereof including the death domain (FAS DD), providing that these modifications yield a self-associating product.

Similarly, once produced and purified, the soluble oligomeric TNF receptors, analogs or derivatives thereof, may be further modified by standard chemical means to provide salts and functional derivatives thereof for the purposes of preparing pharmaceutical compositions containing as active ingredients these TNF receptors of the invention.

For the production of the soluble, oligomeric TNF receptors of the invention, the DNA sequences encoding the extracellular domain of the TNF receptor are obtained from existing clones of the entire TNF receptor, as is the intracellular domain or death domain thereof, and as is also the intracellular domain or death domain of the FAS/APO1 receptor (see Example 2 and Example 5). In this way the DNA sequence of the desired extracellular domain is ligated to the DNA sequence of the desired intracellular domain or portion thereof including the death domain, and this fused product is inserted (and ligated) into a suitable expression vector under the control of the promoter and other expression control sequences. Once formed, the expression vector is introduced (transformation, transfection, etc.) into a suitable host cell, which then expresses the vector to yield the fusion product of the invention being the soluble self-associating TNF receptor molecules. These are then purified from the host cells by standard procedures to yield the final product being the soluble, oligomeric TNF receptors.

The preferred preparation of the fusion product encoding the extracellular domain and intracellular domain or portion thereof is by way of PCR technology using oligonucleotides specific for the desired sequences to be copied from the clones encoding the entire TNF receptor molecule. Other means are also possible, such as isolating the desired portions encoding the extracellular domain and the intracellular domain, by restriction endonucleases and then splicing these together in a known fashion, with or without modifications at the terminal ends of the restriction fragments to ensure correct fusion of the desired portions of the receptor (extracellular and intracellular domains or portions thereof). The so-obtained fusion products are then inserted into the expression vector of choice.

In a similar fashion, the present invention also concerns soluble, oligomeric FAS/APO1 (FAS) receptors containing the extracellular domain of the FAS/APO1 receptor and the self-associating intracellular domain of the p55-R (p55-IC), the death domain thereof (p55DD), or the self-associating intracellular domain of the FAS/APO1 receptor (FAS-IC) or the death domain thereof (FAS DD), or any analogs or derivatives thereof (see above). The construction of these soluble, oligomeric FAS receptors is detailed in Example 5 herein below, using an available cloned full-length FAS receptor-encoding sequence as starting material and the appropriate oligonucleotides for PCR production of the desired extracellular and intracellular domains, followed by ligation thereof to yield a fusion product, which is then inserted into a suitable expression vector. As detailed above and below, prokaryotic or eukaryotic vectors and host cells may be used to produce the desired soluble, oligomeric FAS receptors, which can then be purified and formulated, as active ingredient, into a pharmaceutical composition.

The above soluble, oligomeric FAS receptors of the invention are intended for effective blocking of the FAS ligand, which may also exist as a trimer (similar to TNF, see above), each oligomeric receptor of the invention capable of binding two or possible more FAS ligands and thereby neutralize their activity. The FAS ligand is known to be predominantly cell-surface associated but may also exist in a soluble form. In any event, the oligomeric FAS receptors of the invention can bind to at least two monomers of this ligand and thereby neutralize more effectively (than monomeric FAS receptors) the activity of the FAS ligand. The FAS ligand, and hence activation thereby of the FAS receptor, has been implicated in a number of pathological states, particularly those relating to liver damage (apoptosis of hepatocytes, for example), including liver damage associated with hepatitis, as well as in autoimmune conditions, including lymphocyte damage (apoptosis) in HIV-infected humans (see, for example Ogasawara et al., 1993; Cheng et al., 1994). Accordingly, the soluble, oligomeric FAS receptors of the invention are intended for blocking the activity of FAS ligand and may be used as active ingredient in pharmaceutical compositions for treating such FAS ligand-associated pathological states.

Likewise, the present invention also concerns soluble, oligomeric receptors which have binding affinity for both TNF and FAS-R ligand, the so-called "mixed" TNF-R/FAS-R oligomeric receptors. These mixed oligomeric receptors will contain at least one TNF-R extracellular domain and at least one FAS-R extracellular domain which are associated in the oligomeric receptor by virtue of each of these extracellular domains being fused to any one of the above-mentioned, self-associating, p55IC, p55DD, FAS IC or FAS DD.

These mixed oligomeric receptors may be prepared by:
(a) providing any of the above noted fusion products which contain the extracellular domain of a TNF-R (p75 TNF-R, or preferably, p55 TNF-R).fused to any one of the self-associating intracellular domains p55 IC and FAS IC or any one of the self-associating "death domain" p55DD and FAS DD, or any self-associating portions, analogs or derivatives of any thereof; (b) providing any of the above noted fusion products which contain the extracellular domain of FAS-R fused to any one of the self-associating p55IC, FAS-IC, p55DD, and FAS DD, or any self-associating portions, analogs or derivatives of any thereof; and (c) mixing any of the TNF-specific fusion products of (a) with any of the FAS-R ligand-specific fusion products of (b) to provide (following standard selection and purification procedures) oligomeric (dimeric or higher order oligomeric) receptors which have at least both the extracellular domains of a TNF-R and FAS-R that are associated by virtue of the self-association capability of their fused IC or DD regions.

Another possibility for the preparation of the above mixed oligomeric receptors is by co-transforming suitable host cells with the above-mentioned expression vectors, one of which encodes the TNF-specific TNF-R fusion products and one of which encodes the FAS-R ligand-specific FAS-R fusion products. Following the expression of these different fusion products in the host cells, the mixed oligomeric (TNF-R/FAS-R) receptors may be obtained by standard purification and selection procedures.

The utility of these mixed affinity oligomeric receptors is primarily for the neutralization of both TNF and FAS-R ligand when these are over-expressed endogenously or are at undesirably high levels following exogenous administration. Recent evidence points to a likelihood that there exists a synergism in function between the FAS-R ligand (usually cell-surface associated) and TNF-α (which may also be cell-surface associated). Accordingly, in some instances it is desired to neutralize both of these ligands at the same point on the cell surface, i.e. such a mixed-affinity receptor can block both the TNF binding to its receptor and the binding of FAS-R ligand to its receptor. Accordingly, these mixed-affinity receptors may be used as an active ingredient in pharmaceutical compositions for treating such conditions (see above) where both TNF and FAS-R ligand effects are undesirable.

Similarly, along the lines mentioned above concerning the soluble, oligomeric TNF-R and FAS-R, and mixed TNF-R/FAS-R oligomers of the invention, it is also possible to produce soluble, oligomeric receptors for other receptors, or any mixtures thereof, in particular those of any of the other members of the TNF/NGF super family. In this case, any of the extracellular domains of the various receptors can be fused to the above-mentioned self-associating intracellular domains or portions thereof or to any other intracellular domains of the super family members also capable of self-association.

Expression of any of the recombinant proteins of the invention as mentioned herein can be effected in eukaryotic cells (e.g. yeast, insect or mammalian cells), using the appropriate expression vectors. Any method known in the art may be employed.

For example, the DNA molecules coding for the proteins obtained by any of the above methods are inserted into appropriately constructed expression vectors by techniques well known in the art (see Sambrook et al., 1989). Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

In order to be capable of expressing the desired protein, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example the int promoter of bacteriophageΔ, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophageΔ ($P_L$ and $P_R$), the trp, recA, lacZ, lacI, ompF, and gal promoters of E. coli, or the trp-lac hybrid promoter, etc. (Glick, B. R. (1987). Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3"-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the fusion product proteins of the invention is inserted into a vector having the operably linked transcriptional and translational regulatory signals which is capable of integrating the desired gene sequences into the host cell. The cells which have been stably transformed by the introduced DNA can be selected by also introducing one or more markers which allow for selection of host cells which contain the expression vector. The marker may provide for prototrophy to an auxotrophic host, biocide resistance, e.g. antibiotics, or heavy metals, such as copper, or the like. The selectable marker gene can either be directly linked to the DNA gene sequences to be expressed, or introduced into the same cell by co-transfection. Additional elements may also be needed for optimal synthesis of proteins of the invention. These elements may include transcription promoters, enhancers, and termination signals. cDNA expression vectors incorporating such elements include those described by Okayama, H. (1983).

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli*, for example, pBR322, ColEl, pSC101, pACYC 184, etc. (see Maniatis et al., 1982; Sambrook et al., 1989); Bacillus plasmids such as pC194, pC221, pT127, etc. (Gryczan, T., (1982)); Streptomyces plasmids including pIJ101 (Kendall, K. J. et al., (1987)); Streptomyces bacteriophages such as ØC31 (Chater, K. F. et al., in: *Sixth International Symposium on Actinomycetales Biology,* (1986)), and Pseudomonas plasmids (John, J. F. et al., (1986), and Izaki, K. (1978)). Preferred eukaryotic plasmids include BPV, vaccinia, SV40, 2-micron circle, etc., or their derivatives. Such plasmids are well known in the art (Botstein, D. et al., (1982); Broach, J. R. in: *The Molecular Biology of the Yeast Saccharomyces: Life Cycle and Inheritance* (1981); Broach, J. R., (1982); Bollon, D. P. et al., (1980); Maniatis, T., in: *Cell Biology : A Comprehensive Treatise, Vol.* 3: *Gene Expression,* (1980); and Sambrook et al., 1989).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc.

Host cells to be used in the invention may be either prokaryotic or eukaryotic. Preferred prokaryotic hosts include bacteria such as *E. coli,* Bacillus, Streptomyces, Pseudomonas, Salmonella, Serratia, etc. The most preferred prokaryotic host is *E. coli.* Bacterial hosts of particular interest include *E. coli* K12 strain 294 (ATCC 31446), *E. coli* X1776 (ATCC 31537), *E. coli* W3110 (F-, lambda, prototrophic (ATCC 27325)), and other enterobacterium such as *Salmonella typhimurium* or *Serratia marcescens* and various Pseudomonas species. Under such conditions, the protein will not be glycosylated. The prokaryotic host must be compatible with the replicon and control sequences in the expression plasmid.

Preferred eukaryotic hosts are mammalian cells, e.g. human, monkey, mouse and Chinese hamster ovary (CHO) cells, because they provide post-translational modifications to protein molecules including correct folding or glycosylation at correct sites. Also yeasts cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector, the host cells are grown in a selective medium, which selects for the growth of vector-containing cells. Expression of the cloned gene sequence(s) results in the production of the desired proteins.

Purification of the recombinant proteins is carried out by any one of the methods known for this purpose, i.e. any conventional procedure involving extraction, precipitation, chromatography, electrophoresis, or the like. A further purification procedure that may be used in preference for purifying the protein of the invention is affinity chromatography using anti-TNF receptor monoclonal antibodies, which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

As used herein (see above), the term "salts" refers to both salts of carboxyl groups and to acid addition salts of amino groups of the protein molecule formed by means known in the art. Salts of a carboxyl group include inorganic salts, for example, sodium, calcium, and salts with organic bases as those formed, for example, with amines, such as triethanolamine, arginine or lysine. Acid addition salts include, for example, salts with mineral acids and salts with organic acids.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it. These derivatives include aliphatic esters or amides of the carboxyl groups, and N-acyl derivatives of free amino groups of O-acyl derivatives of free hydroxyl groups formed with acyl moieties (e.g. alkanoyl or carbocyclic aroyl groups).

"Fractions" as used herein refers to any part or portion of the receptor, (intracellular or extracellular domains thereof), or of the proteins binding to the intracellular domain of the receptor, provided it retains its biological activity.

As mentioned above, the present invention also relates to various pharmaceutical compositions comprising a pharmaceutically acceptable carrier and the various noted active ingredients of the invention or their salts, functional derivatives, or mixtures of any of the foregoing. These compositions may be used in any of the conditions as noted herein, for example, in conditions where there is an over production of endogenous TNF, such as in cases of septic shock, cachexia, graft-versus host reactions, autoimmune diseases like rheumatoid arthritis, etc. The way of administration can be via any of the accepted modes of administration for similar agents and will depend on the condition to be treated, e.g. when used to inhibit TNF effects they may be administered intravenously in case of septic shock or local injection in case of rheumatoid arthritis (for example, into the knee), or continuously by infusion, etc. The compositions may also be used, for example, in cases of TNF intoxication caused by exogenous administration of excessive amount (overdoses) of TNF, e.g. in the case of cancer therapy or viral disease therapy.

The pharmaceutical compositions of the invention are prepared for administration by mixing the protein or its derivatives with physiologically acceptable carriers, stabilizers and excipients, and prepared in dosage form, e.g. by lyophilization in dosage vials. The amount of active compound to be administered will depend on the route of administration, the disease to be treated and the condition of the patient. For example, local injection in case of inflammatory conditions of rheumatoid arthritis will require less active ingredient on a body weight basis than will intravenous infusion in case of septic shock.

Other aspects of the invention will be apparent from the following examples.

The invention will now be described in more detail in the following non-limiting examples and the accompanying drawings:

EXAMPLE 1

Cloning and Isolation of Proteins Which Bind to the Intracellular Domains of the p55 and p75 TNF Receptors To isolate proteins interacting with the intracellular domains of the p55 and p75 TNF receptors (p55IC and p75

IC), the yeast two-hybrid system was used (Fields and Song, 1989). Briefly, this two-hybrid system is a yeast-based genetic assay to detect specific protein-protein interactions in vivo by restoration of a eukaryotic transcriptional activator such as GAL4 that has two separate domains, a DNA binding and an activation domain, which domains when expressed and bound together to form a restored GAL4 protein, are capable of binding to an upstream activating sequence which in turn activates a promoter that controls the expression of a reporter gene, such as lacZ or HIS3, the expression of which is readily observed in the cultured cells. In this system the genes for the candidate interacting proteins are cloned into separate expression vectors. In one expression vector the sequence of the one candidate protein is cloned in phase with the sequence of the GAL4 DNA-binding domain to generate a hybrid protein with the GAL4 DNA-binding domain, and in the other vector the sequence of the second candidate protein is cloned in phase with the sequence of the GAL4 activation domain to generate a hybrid protein with the GAL4-activation domain. The two hybrid vectors are then co-transformed into a yeast host strain having a lacZ or HIS3 reporter gene under the control of upstream GAL4 binding sites. Only those transformed host cells (cotransformants) in which the two hybrid proteins are expressed and are capable of interacting with each other, will be capable of expression of the reporter gene. In the case of the lacZ reporter gene, host cells expressing this gene will become blue in color when X-gal is added to the cultures. Hence, blue colonies are indicative of the fact that the two cloned candidate proteins are capable of interacting with each other.

Using this two-hybrid system, the intracellular domains p55IC and p75IC were cloned, separately, into the vector pGBT9 (carrying the GAL4 DNA-binding sequence, provided by CLONTECH, USA, see below), to create fusion proteins with the GAL4 DNA-binding domain (similarly, the intracellular domain, FAS-IC and a portion of the 55IC, namely, the 55DD were also cloned into pGBT9 and used to isolate other IC-binding proteins, see Example 3 below). For the cloning of p55IC and p75IC into pGBT9, clones encoding the full-length cDNA sequences of p55 TNF-R (Schall et al., 1990) and p75 TNF-R (Smith et al., 1990) were used from which the intracellular domains (IC) were excised as follows: p55IC was excised using the enzymes EcoRI and SalI, the EcoRI-SalI fragment containing the p55IC sequence was then isolated by standard procedures and inserted into the pGBT9 vector opened, in its multiple cloning site region (MCS), with EcoRI and SalI. p75 IC was excised using the enzymes BspHI and SalI, the BspHI-SalI fragment containing the p75 IC sequence was then isolated by standard procedures and filled-in-with the Klenow enzyme to generate a fragment which could be inserted into the pGBT9 vector opened with SmaI and SalI.

The above hybrid (chimeric) vectors were then cotransfected (separately, one cotransfection with the p55IC hybrid and one with the p75 IC hybrid vector) together with a cDNA library from human HeLa cells. cloned into the pGAD GH vector, bearing the GAL4 activating. domain, into the HF7c yeast host strain (all the above-noted vectors, pGBT9 and pGAD GH carrying the HeLa cell cDNA library, and the yeast strain were purchased from Clontech Laboratories, Inc., USA, as a part of MATCHMAKER Two-Hybrid System, #PT1265-1). The co-transfected yeasts were selected for their ability to grow in medium lacking Histidine (His⁻medium), growing colonies being indicative of positive transformants. The selected yeast clones were then tested for their ability to express the lacZ gene, i.e. for their LAC Z activity, and this by adding X-gal to the culture medium, which is catabolized to form a blue colored product by β-galactosidase, the enzyme encoded by the lacZ gene. Thus, blue colonies are indicative of an active lacZ gene. For activity of the lacZ gene, it is necessary that the GAL4 transcription activator be present in an active form in the transformed clones, namely that the GAL4 DNA-binding domain encoded by one of the above hybrid vectors be combined properly with the GAL4 activation. domain encoded by the other hybrid vector. Such a combination is only possible if the two proteins fused to each of the GAL4 domains are capable of stably interacting (binding) to each other. Thus, the His⁺ and blue (LAC Z⁺) colonies that were isolated are colonies which have been cotransfected with a vector encoding p55IC and a vector encoding a protein product of human HeLa cell origin that is capable of binding stably to p55 IC; or which have been transfected with a vector encoding p75IC and a vector encoding a protein product of human HeLa cell origin that is capable of binding stably to p75 IC.

The plasmid DNA from the above His⁺, LAC Z⁺ yeast colonies was isolated and electroporated into *E. coli* strainHB101 by standard procedures followed by selection of Leu⁺ and Ampicillin resistant transformants, these transformants being the ones carrying the hybrid pGAD GH vector which has both the Amp$^R$ and Leu² coding sequences. Such transformants therefore are clones carrying the sequences encoding newly identified proteins capable of binding to the p55IC or p75IC. Plasmid DNA was then isolated from these transformed *E. coli* and retested by:

(a) retransforming them with the original intracellular domain hybrid plasmids (hybrid pGTB9 carrying either the p55IC or p75IC sequences) into yeast strain HF7 as set forth hereinabove. As controls, vectors carrying irrelevant protein encoding sequences, e.g. pACT-lamin or pGBT9 alone were used for cotransformation with the p55IC-binding protein or p75IC-binding protein encoding plasmids. The cotransformed yeasts were then tested for growth on His⁻ medium alone, or with different levels of 3-aminotriazole; and (b) retransforming the plasmid DNA and original intracellular domain hybrid plasmids and control plasmids described in (a) into yeast host cells of strain SFY526 and determining the LAC Z⁺ activity (effectivity of β-gal formation, i.e. blue color formation).

The results of the above tests revealed that the pattern of growth of colonies in His⁻ medium was identical to the pattern of LAC Z activity, as assessed by the color of the colony, i.e. His⁺ colonies were also LAC Z⁺. Further, the LAC Z activity in liquid culture (preferred culture conditions) was assessed after transfection of the GAL4 DNA-binding and activation-domain hybrids into the SFY526 yeast hosts which have a better LAC Z inducibility with the GAL4 transcription activator than that of the HF-7 yeast host cells.

The results of the above co-transfections are set forth in Table 1 below, from which it is apparent that a number of proteins were found that were capable of binding to the p55IC or the p75IC, namely, the proteins designated 55.11, which binds to the p55IC; and 75.3 and 75.16 which bind to the p75IC. All of these p55IC- and p75IC-binding proteins are authentic human proteins all encoded by cDNA sequences originating from the HeLa cell cDNA library, which were fused to the GAL4 activation-domain sequence in the plasmid pGAD GH in the above yeast two-hybrid analysis system.

Interestingly, it was also found that fragments of the p55IC, itself, namely, the proteins designated 55.1 and 55.3 were capable of binding to p55IC. These are discussed also in Example 2 below.

TABLE 1

SUMMARY OF THE CHARACTERISTICS OF SOME OF THE cDNA CLONES (SEE ALSO EXAMPLE 3) ISOLATED BY THE TWO-HYBRID SYSTEM APPROACH

| DNA-binding domain hybrid | Activation-domain hybrid | Colony color | Lac Z activity in liquid culture assay |
|---|---|---|---|
| pGBT9-IC55 | — | white | 0.00 |
| pGBT9-IC55 | 55.1 | blue | 0.65 |
| pGBT9-IC55 | 55.3 | blue | 0.04 |
| — | 55.1 | white | 0.00 |
| — | 55.3 | white | 0.00 |
| pACT-Lamin | 55.1 | white | 0.00 |
| pACT-Lamin | 55.3 | white | 0.00 |
| pGBT9 | 55.1 | white | 0.00 |
| pGBT9 | 55.3 | white | 0.00 |
| pGBT9-IC55 | 55.11 | blue | ND |
| — | 55.11 | white | ND |
| pACT-Lamin | 55.11 | white | ND |
| pGBT9 | 55.11 | white | ND |
| pGBT9-IC75 | 75.3 | blue | ND |
| pGBT9-IC75 | — | white | ND |
| — | 75.3 | white | ND |
| pACT-Lamin | 75.3 | white | ND |
| pGBT9 | 75.3 | white | ND |
| pGBT9-IC75 | 75.16 | blue | ND |
| — | 75.16 | white | ND |
| pACT-Lamin | 75.16 | white | ND |
| pGBT9 | 75.16 | white | ND |

In the above Table 1, the plasmids and hybrid encoding the GAL4 DNA-binding domain and GAL4 activation domain are as follows:
DNA-binding Domain Hybrids
pGBT9-IC55: full-length intracellular domain of the p55-TNF-R (p55IC)
pACT-Lamin: irrelevant protein—lamin.
pGBT9: vector alone
pGBT9-IC75: full-length intracellular domain of the p75-TNF-R (p75IC)
Activation-domain Hybrid
55.1 and 55.3 correspond to fragments of the intracellular domain of the p55-TNF-R.
55.11: is the novel protein associating with the p55-TNF-R
75.3 and 75.16 are the novel proteins associating with the p75-TNF-R.

Figure 1A:
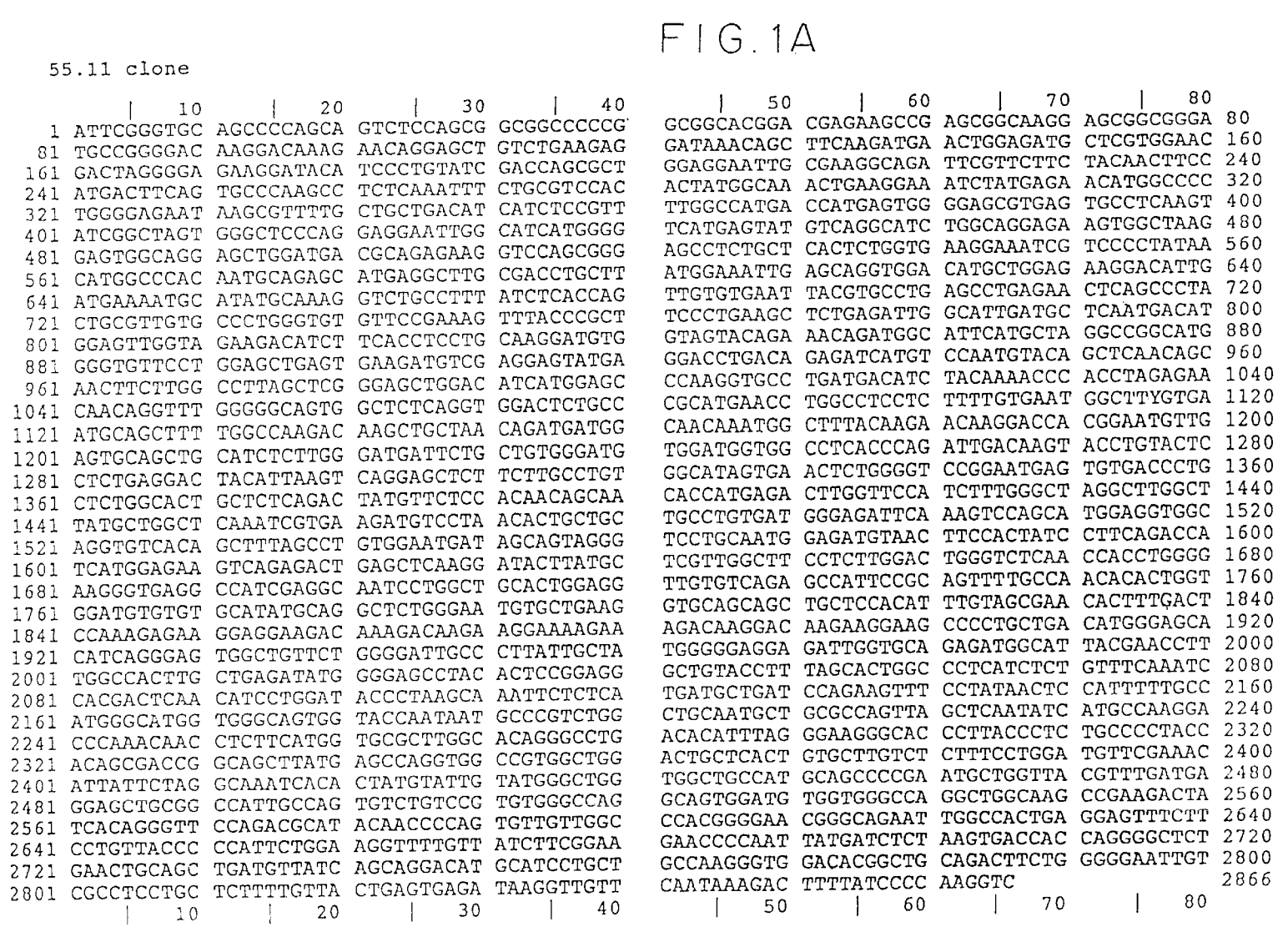

The above noted cloned cDNAs encoding the novel p55IC- and p75IC-binding proteins, 55.11, 75.3 and 75.16, were then sequenced using standard DNA sequencing procedures. The partial sequence of all of these protein-encoding sequences is set forth in FIGS. 1a–c, where FIG. 1(a) depicts the sequence of the cDNA encoding protein 55.11; FIG. 1(b) depicts the partial sequence of the cDNA encoding protein 75.3; and FIG. 1(c) depicts the partial sequence of the cDNA encoding protein 75.16. In FIG. 1(d) there is shown the deduced amino acid sequence of the protein 55.11, as deduced from the nucleotide sequence of FIG. 1(a).

It should be noted, however, that a partial sequence of the cDNA encoding the 55.11 protein has also been reported by Khan et al. (1992), in a study of human brain cDNA sequences, which study was directed at the establishment of a new rapid and accurate method for the sequencing and physical and genetic mapping of human brain cDNAs. However, Khan et al. did not provide any information as regards the function or any other characteristics of the protein encoded by the 55.11 cDNA sequence, such functional or other analysis not being the intention of Khan et al. in their study.

Analysis and Characterization of the 55.11 Protein
(a) General Procedures and Materials
    (i) Cloning of the cDNA of 55.11
    Upon the analysis (for example, Northern Analysis—see below) of the cDNA of protein 55.11, it was revealed that the above noted 55.11 cDNA cloned by the two-hybrid screen procedure represented only a partial cDNA of 55.11 having nucleotides 925–2863 (see FIG. 1(a)) which code for amino acids 309–900 (see FIG. 1(d)). The remaining part of the 55.11 cDNA [nucleotides 1–924 (FIG. 1(a)) which code for amino acids 1–308 (FIG. 1(d))] was obtained by standard procedures, namely, by cloning by PCR from a human fetal liver cDNA library (for more details, see below). The full nucleotide sequence of 55.11 (FIG. 1(a)) was determined in both directions by the dideoxy chain termination method.
    (ii) Two-hybrid β-galactosidase Expression Tests
    β-galactosidase expression tests were performed as described above, except that in some of the tests, the pVP16 vector, which contains the activation domain of VP16, was used instead of pGAD-GH, the Gal4 activation domain vector. Numbering of residues in the proteins encoded by the cDNA inserts are as in the Swiss-Prot data bank. Deletion mutants were produced by PCR, and point mutations by oligonucleotide-directed mutagenesis (Kunkel, 1994).
    (iii) Northern Analysis
    Total RNA was isolated using TRI REAGENT (Molecular Research Center, Inc., Cincinnati, Ohio, U.S.A.), denatured in formaldehyde/formamide buffer, electrophoresed through an agarose/formaldehyde gel, and blotted to a GeneScreen Plus membrane (Dupont, Wilmington, Del., U.S.A.) in 10×SSPE buffer, using standard techniques. The blots were hybridized with the partial cDNA of 55.11 (see above, nucleotides 925–2863), radiolabeled with the random-prime kit (Boehringer Mannheim Biochemica, Mannheim, Germany), and washed stringently. Autoradiography was performed for 1 week.
    (iv) Expression of 55.11 cDNA in HeLa Cells and Binding of the 55.11 Protein to Glutathione S-transferase Fusion Proteins of P55-IC
    Glutathione S-transferase (GST) fusions with p55-IC (GST-p55IC) and with p55-IC truncated below amino acid 345 (GST-p55IC345) were produced and adsorbed to glutathione-agarose beads as described in Example 2 below (see also Smith and Corcoran, 1994; Frangioni and Neel, 1993). The cDNAs of 55.11 (1–2863 nucleotides, i.e. the full-length 55.11 cDNA), of FLAG-55.11, and of luciferase were expressed in HeLa cells. FLAG-55.11 is the region extending between residues 309 and 900 in the 55.11 protein (the partial cDNA of 55.11 (nucleotides 925–2863), originally cloned by the two hybrid screen), N-linked to the FLAG octapeptide (Eastman Kodak, New Haven, Conn., U.S.A.). Expression of the fusion proteins was accomplished using a tetracycline-controlled expression vector (HtTA-1) in a HeLa cell clone that expresses a tetracycline-controlled transactivator (see Example 2 below, and Gossen and Bujard, 1992). Metabolic labeling of the expressed proteins with [$^{35}$S] Met and [$^{35}$S] Cys (Dupont, Wilmington, Del., U.S.A. and Amersham, Buckinghamshire, England), lysis of the HeLa cells, immunoprecipitation, and binding of the labeled proteins to the GST fusion proteins were performed as described below (Example 2), except that 0.5% rather than 0.1% Nonidet P-40 was present in the cell lysis buffer. The immunoprecipitations of 55.11 and FLAG-55.11 were achieved using a rabbit antiserum (diluted 1:500) raised against a GST fusion protein containing the region of 55.11 that extends between amino acids 309 and 900 and a mouse monoclonal antibody against the FLAG octapeptide (M2; Eastman Kodak; 5 µg/ml of cell lysate).

(b) Binding of the 55.11 Protein to p55-IC within Transformed Yeasts

In this study it was sought to ascertain the nature of the binding between 55.11 and p55IC, in particular, the regions of both of these proteins involved in this binding. For this purpose the above two-hybrid procedure was used in which various full-length and deletion mutants of p55IC (see also Example 2 below) in "DNA-binding domain" constructs were used as "baits" to bind the "preys", being the partial 55.11 protein encoded in constructs in which the partial 55.11 sequence (residues 309–900, as originally isolated) was fused to the "activation domain" in the vectors GAL4AD and VP16AD. Further, various deletion mutants of 55.11 were also constructed and fused to the "activation domain" in the GAL4AD vector (e.g. mutants of 55.11 having only residues 309–680 and 457–900). The binding of the various "binding domain" constructs to the various "activation domain" constructs was examined in transfected SFY526 yeast cells. The binding was assessed by a two-hybrid β-galactosidase expression filter assay. The non-relevant proteins SNF1 and SNF4 served as positive controls for the "binding domain" and "activation domain" constructs, respectively; the empty Gal4 (pGAD-GH) and VP16 (pVP16) vectors served as negative controls for the "activation domain" constructs; and the empty Gal4 (pGBT9) vector served as a negative control for the "binding domain" constructs. The results of the assay are set forth in FIG. 13 in which the symbols "+++" and "++" indicate the development of strong color within 20–60 min of initiation of the assay, respectively (positive binding results); and "−" indicates no development of color within 24 h of commencement of the assay (negative results). Blank spaces in FIG. 13 indicate binding assays not tested.

From the results presented in FIG. 13 above it may be concluded that 55.11 binds to p55-IC at a site which is distinct from the "death domain" (residues 328–426) of p55-IC.

The 55.11 protein bound to a truncated p55-IC from which the death domain had been deleted (construct 206–328 in FIG. 13), more effectively than to nontruncated p55-IC. It also bound to an even further C terminally truncated construct (construct 206–308) and to a construct from which both the death domain and a membrane proximal part were deleted (construct 243–328). However, the 55.11 protein did not bind to a construct that was N-terminally truncated down to amino acid 266 (FIG. 13). These findings indicate that the binding site for 55.11 is located in the region that extends between residues 243 and 308 of p55-IC and that the N terminus of this binding site is between residues 243 and 266.

Transfer of the cDNA for 55.11 from the originally cloned "prey" construct, which contained the Gal4 activation domain, to a prey construct containing the VP16 activation domain did not decrease the binding efficiency of the 55.11 protein to p55-IC (FIG. 13). Thus, the structure(s) involved in this binding appear to reside within the 55.11 molecule and not to involve the site of fusion of 55.11 with the activation domain.

However, binding of 55.11 to p55-IC was abolished by even limited truncations of the 55.11 protein at either its C (55.11 construct 309–680) or N terminus (55.11 construct 457–900) (residue 309 is the first residue in the 55.11 protein encoded by the partial cDNA clone originally isolated in the two hybrid screen).

The observed binding between 55.11 and p55-IC appeared to be specific since 55.11 did not bind to other proteins, including three receptors of the TNF/NGF receptor family (p75-R, FAS/APO1 and CD40) and other proteins such as lamin and cyclin D (data not shown). It should be noted that of the other TNF/NGF receptor proteins tested there was also tested portions thereof which include their intracellular domains: human FAS-R (residues 175–319), CD40 (residues 216–277) and p75-TNF-R (residues 287–461), none of which bound 55.11 (data not shown).

(c) Northern Analysis of the RNA from Several Cell Lines, Using the 55.11 cDNA as a Probe and Cloning of the Full-length 55.11 cDNA The cell lines examined were HeLa, CEM, Jurkat, and HepG2. cells derived from human epithelial carcinoma, an acute lymphoblastic T cell leukemia, an acute T cell leukemia, and a hepatocellular carcinoma, respectively. The 55.11 cDNA original isolated (nucleotides 925–2863) was used as a probe. Samples consisted of 10 g of RNA/lane. The results of the Northern analysis are shown in FIG. 2, which is a reproduction of a Northern blot.

Figure 2:
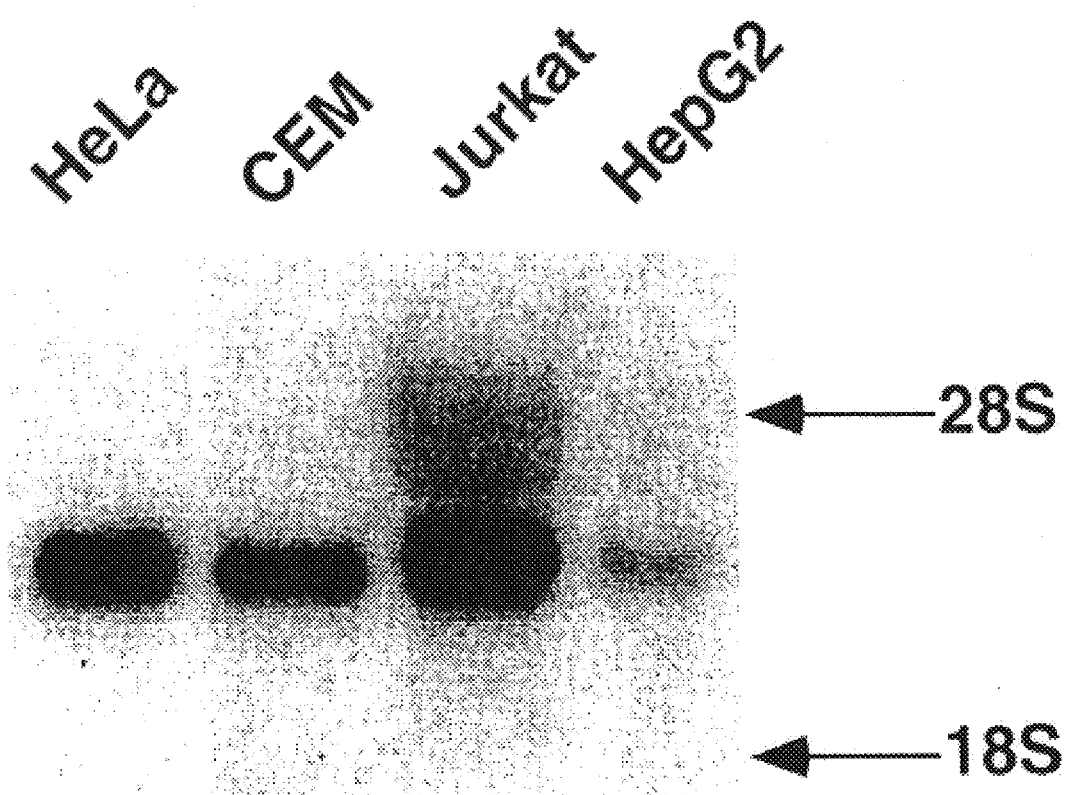
FIG. 2 is a reproduction of a Northern blot which shows the 55.11-specific mRNAs present in a number of tested cell lines, as described in Example 1.

From FIG. 2 it is thus apparent that the Northern analysis using the 55.11cDNA as a probe revealed, in several cell lines, a single hybridizing transcript of about 3 kB, which is larger than the cDNA (2 kB) of the originally isolated 55.11 cDNA. Using oligonucleotide primers that correspond to the 55.11 sequence, we cloned by PCR a 5" extending sequence whose length was about 1 kB. The sum of the length of this 5" extending sequence with that of the originally cloned cDNA approximates the length of the 55.11 transcript. The 3 kB cDNA that encompassed both these portions was effectively expressed in transfected HeLa cells (see below) yielding a protein of about 84 kDa, which suggests that the 3 kB cDNA contains a translational start site.

(d) In vitro Binding of the 55.11 Protein to GST-fusion Proteins Containing Portions of p55-IC To ascertain that 55.11 can indeed bind to p55-IC and to exclude involvement of yeast proteins in this binding, the in vitro interaction of GST p55-IC fusion proteins, produced by bacteria, with the protein encoded by the 3 kB 55.11 cDNA (55.11-full), produced by transfected HeLa cells, was examined. In this study the cDNAs for the full-length 55.11, FLAG-55.11 (residues 309–900 of 55.11 encoded by the originally cloned partial cDNA and fused at the N terminus with the FLAG octapeptide), and luciferase (control) were expressed in transfected HeLa cells and metabolically labeled with [$^{35}$S] Met and [$^{35}$S] Cys. The following proteins were fused with GST: full-length p55-IC (GST-p55-IC) and p55-IC C-terminally truncated up to amino acid 345 (GST-p55-IC345) to remove most of the "death domain" (see FIG. 13). GST alone served as a control. Lysates of the transfected cells were immunoprecipitated with antibodies against the 55.11 protein when the full-length 55.11 protein was used for binding the GST-fusion proteins, or with antibodies against the FLAG octapeptide when the FLAG-55.11 fusion product was used for binding the GST-fusion proteins. The proteins were analyzed by SDS-polyacrylamide gel electrophoresis (SDS-PAGE; 10% acrylamide), followed by autoradiography.

Figure 3A:
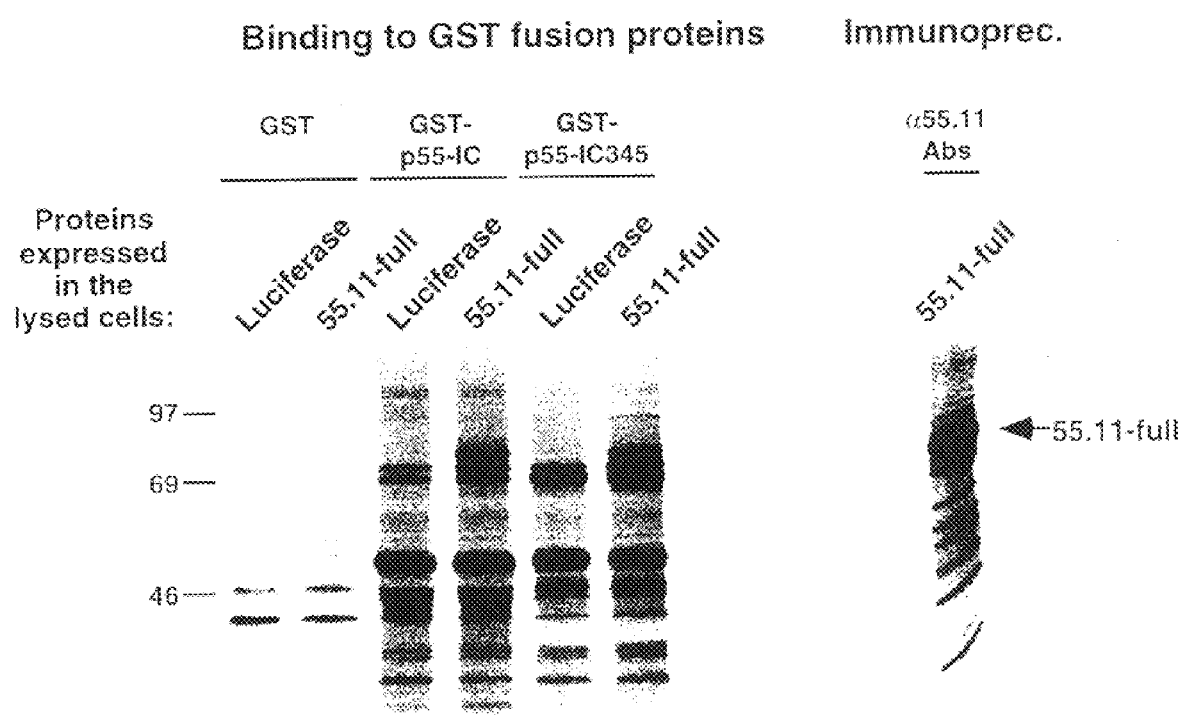
FIGS. 3A and B are reproductions of autoradiograms depicting the in vitro binding of the protein encoded for by the 55.11 cDNA to GST fusion proteins containing portions of p55-IC, wherein in FIG. 3A there is depicted the binding of the full-length 55.11 protein (55.11 full) to the various GST fusion proteins; and in FIG. 3B there is depicted the binding of a portion of 55.11 fused to the FLAG octapeptide to the various GST fusion proteins, all as described in Example 1.

In FIGS. 3A and B are shown reproductions of the autoradiograms of the above SDS-PAGE gels, in which FIG. 3A depicts the binding of the full-length 55.11 protein (55.11-full) to the various GST-fusion proteins; and in which FIG. 3B depicts the binding of the Flag-55.11 fusion product to the various GST-fusion proteins. In FIG. 3A there is shown in the extreme right hand lane a control immunoprecipitate of lysates of cells transfected with only the full-length 55.11 and immunoprecipitated with the anti-55.11 antibodies (α55.11 Abs). In FIG. 3B there is shown in the extreme right hand lane a control immunoprecipitate of lysates of cells transfected with only the FLAG-55.11 and immunoprecipitated with the anti-FLAG antibodies (FLAG Abs).

Thus, it is apparent from FIGS. 3A and B that the protein encoded by the full-length 55.11 cDNA can be expressed in HeLa cells and it binds to fusion proteins that contained the full p55-IC (GST-p55IC) or a truncated p55-IC that lacked most of the death domain (GST-p55IC345) (FIG. 3A). The full-length 55.11 protein did not bind to GST alone (control). Similarly, the HeLa cell-expressed protein encoded by the initially cloned partial cDNA of 55.11 in fusion with the FLAG octapeptide (FLAG-55.11) bound in vitro to GST-p55IC and GST-p55IC345, but not to GST (FIG. 3B). The above results also therefore provide additional evidence (see (b) above) that the 55.11 binds to a region of the p55IC upstream of the "death domain", i.e. in the region of the p55-IC that is more proximal to the transmembrane domain.

Moreover, the above study also demonstrates that, in accordance with the present invention, antibodies to 55.11 have been successfully produced (FIG. 3A).

(e) Comparison of the Deduced Amino Acid Sequence of Human 55.11 to that of Related Proteins Present in Lower Organisms, and Sequence Features of the 55.11 Protein As mentioned above, in accordance with the present invention, the full-length 55.11 cDNA has been cloned and sequenced (see nucleotide sequence in FIG. 1(*a*)) and the full amino acid sequence of 55.11 has been deduced from the cDNA sequence (see amino acid sequence in FIG. 1(*d*)). Data bank (GenBank™/EMBL DataBank) searches revealed that parts of the sequence of the human 55.11 cDNA (accession numbers T03659, Z19559, and F09128) and its mouse homologue (accession numbers X80422 and Z31147) have already been determined during arbitrary sequencing of cDNA libraries. A cDNA sequence (accession number U18247) that encodes for a human protein of 596 amino acids present in cultures of human hepatoma HC10 cells is similar to that of 55.11. This hepatoma protein, however, lacks an N terminal portion (amino acids 1–297) corresponding to that of 55.11 and also differs from 55.11 at the regions that correspond to residues 297–377 and residues 648–668 in 55.11. The searches of the data bank also revealed that proteins with very high sequence homology to 55.11 exist in *Saccharomyces cerevisiae* (yeasts), *Arabidopsis thaliana* (plants) and *Caenorhabditis elegans* (worms). Thus, 55.11 appears to fulfill an evolutionary conserved function. In the yeasts, there are two known proteins (the open reading frame YHR027c and SEN3) whose DNA sequences resemble that of 55.11. The sizes of both are close to that of 55.11. YHR027c is known only by the sequencing of a genomic clone while SEN3 has been cloned as a cDNA. The sites within 55.11 that are similar to those in SEN3 correlate to the sites of its similarity to YHR027c, although much more similarity is evident between 55.11 and YHR027c than between 55.11 and SEN3. The DNA sequence information available for the *Arabidopsis thaliana* and *Caenorhabditis elegans* proteins, although only partial, clearly shows that these proteins are as similar to 55.11 as the YHR027c protein of yeast. The only one of these four proteins whose nature has been elucidated so far is the yeast SEN3, whose homology to 55.11 is limited. SEN3 has been identified as the yeast equivalent of the p112 subunit of an activator of the 20S proteasome (the proteolytic core of the 26S proteasome [Rechsteiner et al., 1993; DeMartino et al., 1994]) (M. R. Culbertson and M. Hockstrasser, personal communication).

In FIG. 4 there is shown schematically a comparison of the deduced amino acid sequence of human 55.11 to that of the above-mentioned, related proteins present in lower organisms. In FIG. 4 the sequences that are compared are the sequences of amino acids predicted for: the 55.11 cDNA (see FIG. 1(*d*); SEQ ID NO:14); an open reading frame (YHR027c) within a cosmid derived from the 8th chromosome of *Saccharomyces cerevisiae* (nucleotides 21253–24234, accession number U10399; SEQ ID NO:15); SEN3, the cDNA of a Saccharomyces cerevisiae protein (accession number L06321; SEQ ID NO:16); a partial cDNA of a protein of the plant *Arabidopsis thaliana* (accession number T21500; SEQ ID NO:17); and a partial cDNA of a protein of the nematode *Caenorhabditis elegans* (accession number D27396; SEQ ID NO:18). The "KEKE" sequence in 55.11 is marked with a solid line and the sequence AYAGS(x)$_8$LL (SEQ ID NO:38) with broken lines. The sequences were aligned using the PILEUP and PRETTYBOX programs of the GCG package. Gaps introduced to maximize alignments are denoted by dashes.

As regards the various sequence features or motifs present in the human 55.11 sequence the following has been observed: Conserved amino acid sequence motifs were not discerned within the protein encoded for by 55.11, except for a repetitive "KEKE" sequence that extends between Lys 614 and Glu 632 (underlined in FIG. 4). Such "KEKE" sequences, which are present in many proteins, including proteasonal subunits and chaperonins, may promote association of protein complexes (Realini et al., 1994). A sequence AYAGS(x)$_8$LL (SEQ ID NO:38) appears twice in the 55.11 protein (at sites 479, 590, see FIG. 4); no functional significance for this sequence has yet been described.

(f) Sequence Features of the p55IC Region Involved in Binding to the 55.11 Protein As described above (see (b) and (d)), the 55.11 protein binds to a region of the p55-IC between residues 243 and 308 (the N terminus of this binding site being between residues 243 and 266), this region is upstream of the "death domain" and more proximal to the transmembrane domain of the p55-TNF-R. This region within p55-IC to which 55.11 binds has a high content of proline, serine, and threonine residues. However, this region does not contain the RPM1 and RPM2 proline-rich motifs present in several other cytokine receptors (O'Neal and Yu-Lee, 1993). In the region that extends between residues 243 and 266, whose deletion abolishes the binding of p55-R to 55.11 (see (b) and (d) above and FIG. 13), two of the serines and two of the threonines are followed by proline residues, which makes them potential sites for phosphorylation by MAP kinase, CDC2, and other proline-dependent kinases (Seger and Krebs, 1995). Phosphorylation of this site in the receptors might affect its binding to the 55.11 protein.

In view of all of the aforementioned with regards to protein 55.11 and its binding to p55-IC it can be concluded that in accordance with the present invention, a new protein has been found which binds to a distinct region upstream to the "death domain" of p55-IC. Such binding could affect TNF-mediated activities other than induction of cell death. The region to which 55.11 binds has previously been shown to be involved in induction of nitric oxide synthase (Tartaglia et al., 1993), and appears to be involved in the activation of the neutral sphingomyelinase by TNF (Wiegmann et al., 1994). It is thus possible that association (binding) of 55.11 with the intracellular domain of p55-TNF-R (p55 IC) affects or is involved in: (i) the signaling for these above noted or other TNF effects, (ii) the folding or processing of the protein (as suggested by the similarity of 55.11 to a subunit of the 26S proteasome), or (iii) the regulation of the activity or expression of p55-TNF-R.

EXAMPLE 2

Self-association Ability of the Intracellular Domain of the p55 TNF Receptor (p55IC) and its Capability to Cause Cell Death and Other Features and Activities Thereof, and a Related FAS/APO1 Receptor"s Intracellular Domain As set forth in Example 1 above, it was discovered that the intracellular domain of p55 TNF-R (p55IC) is capable of binding to itself, and further that fragments of p55IC, namely proteins 55.1 and 55.3, are also capable of binding to p55IC.

It is known that the binding of TNF to p55 TNF-R leads to a cytocidal effect on the cells carrying this receptor. Further, antibodies against the extracellular domain of this receptor can themselves trigger this effect, in correlation with the effectivity of receptor cross-linking by them.

In addition, mutational studies (Tartaglia et al., (1993); Brakebusch et al., (1992)) showed that the function of the p55-R depends on the integrity of its intracellular domain. It was therefore suggested that the initiation of signaling for the cytocidal effect of TNF occurs as a consequence of association of two or more intracellular domains of the p55-R (p55-IC), imposed by receptor aggregation. The results in accordance with the present invention provide further evidence for this notion, showing that expression of the intracellular domain of the p55-R within cells, without the transmembrane or intracellular domain, triggers their death. Such free intracellular domains of the p55-R are shown to self associate, which probably accounts for their ability to function independently of TNF. The fact that the signaling by the full length p55-R does depend on TNF stimulation is suggested to reflect activiti(es) of the trans-membrane or extracellular domain of the receptor which decrease or prevent this self association.

The ability of the intracellular domain of the p55-R (p55-IC) to self associate was found serendipitously, in the attempts to clone effector proteins which interact with this receptor (see Example 1 above). We applied for that purpose the above mentioned "two hybrid" technique. In addition to the novel protein, 55.11 found to associate (bind) to the p55IC, it was also found that three other cloned HeLa cell cDNAs contained cDNA sequences encoding for parts of the intracellular domain of the p55-R, implying that the p55-IC is capable of self-association. Two of these clones were identical, containing an insert which encodes for amino acids 328–426 (designated as clone 55.1 encoding protein fragment 55.1 of the p55IC). The third contained a longer insert, encoding for amino acids 277–426 (designated as clone 55.3 encoding protein fragment 55.3 of the p55IC).

In addition, we assessed the in vitro interaction between two bacterially produced chimeras of the p55IC, one, in which it was fused to the maltose binding protein (MBP) and the other in which is was fused to the glutathione-S-transferase (GST). These chimeras were constructed, cloned and expressed by standard methods. Following their expression, the assessment of the self-interaction of the p55-R intracellular domain (p55IC) by determining the interaction of the above bacterially-produced chimeric proteins GST-IC55 (Mr—51 kD) and MBP-IC55 (Mr—67 kD) with each other. Equal amounts of the GST-IC55 chimera (samples of lanes 1–4 in FIG. 5) or GST alone (samples of lanes 5–8 in FIG. 5) were bound to glutathione-agarose beads (Sigma) and were then incubated with the same amount of MBP-IC55 fusion protein in one of the following buffer solutions:

(i) buffer I (20 mM Tris-HCl, pH 7.5, 100 mM KCl, 2 mM CaCl$_2$, 2 mM MgCl$_2$, 5 mM DTT, 0.2% Triton X100, 0.5 mM PMSF, 5% Glycerol). This was done for the samples of Lanes 1 and 5 of FIG. 5.

(ii) buffer I containing 5 mM EDTA instead of MgCl$_2$. This was done for the samples of Lanes 2 and 6 of FIG. 5.

(iii) buffer I containing 250 mM instead of 100 mM KCl. This was done for the samples of Lanes 3 and 7 of FIG. 5.

(iv) buffer I containing 400 mM instead of 100 mM KCl. This was done for the samples of Lanes 4 and 8 of FIG. 5.

After incubation with rotation for 2 h at 4° C., the beads were washed with the same buffers and then boiled in SDS-PAGE buffer followed by electrophoresis by PAGE. The proteins on the gel were then Western blotted to a nitrocellulose membrane which was then stained with polyclonal antiserum against MBP. A reproduction of this stained Western blot is shown in FIG. 5, the samples in lanes 1–8 being those noted above.

Figure 5:
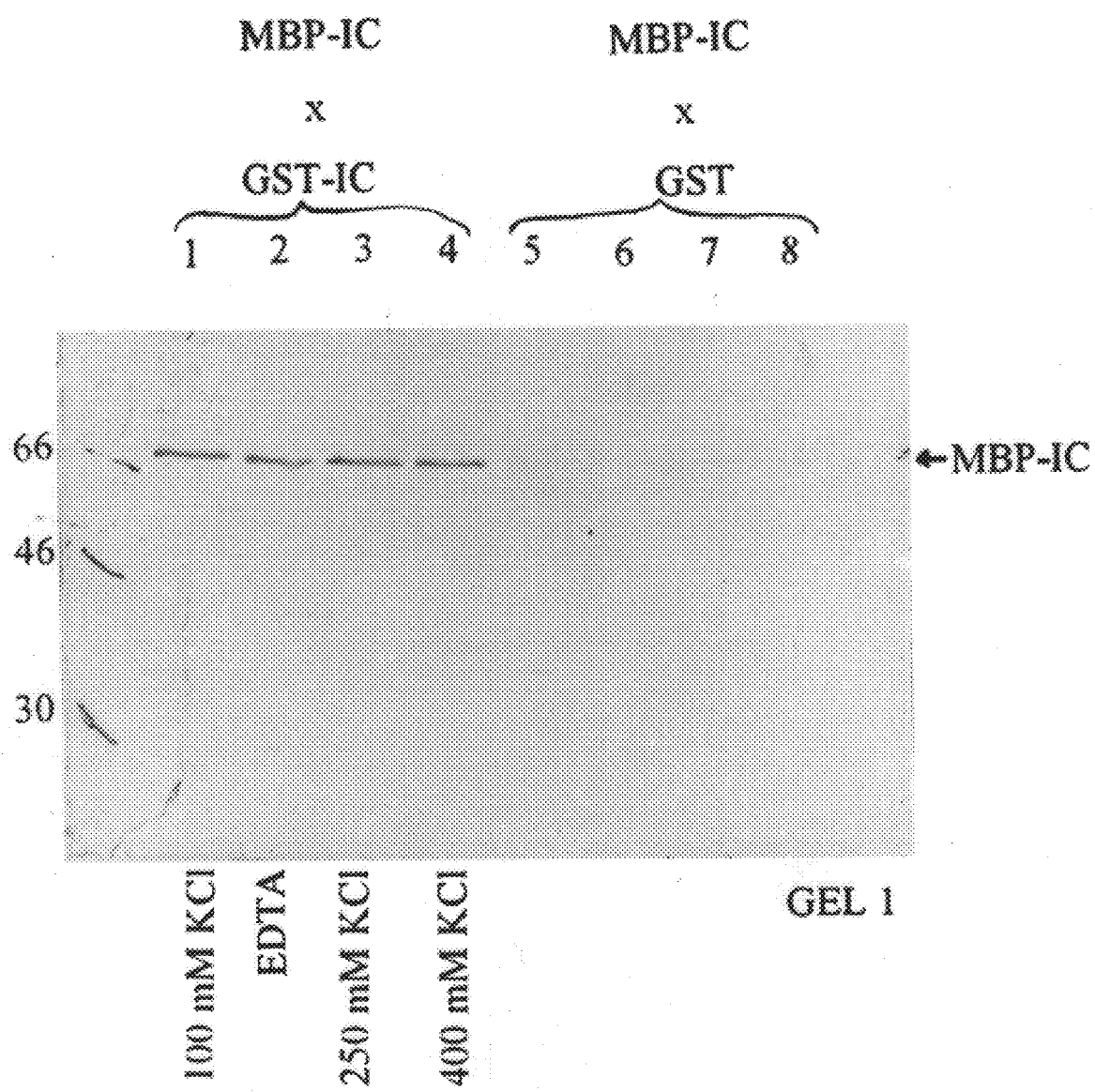
FIG. 5 is a reproduction of a Western blot stained with anti-MBP polyclonal antiserum, showing the self association of the p55IC, the Western blot derived from an SDS-PAGE gel on which were electrophoresed the interacting bacterially-produced chimeric proteins p55IC-MBP and p55IC-GST (lanes 1–4) or the control interaction between the chimeric protein p55IC-MBP and GST alone (lanes 5–8), the interactions between the chimeric proteins (and control) being carried out on glutathione-agarose beads prior to SDS-PAGE, as described in Example 2.

From FIG. 5 it is apparent that the p55IC-MBP chimera binds to the p55IC-GST chimera (lanes 1–4) independently of divalent cations and even at a rather high salt concentration (0.4M KCl). Thus, it is concluded that the p55IC is able to avidly self-associate.

Figure 6A:
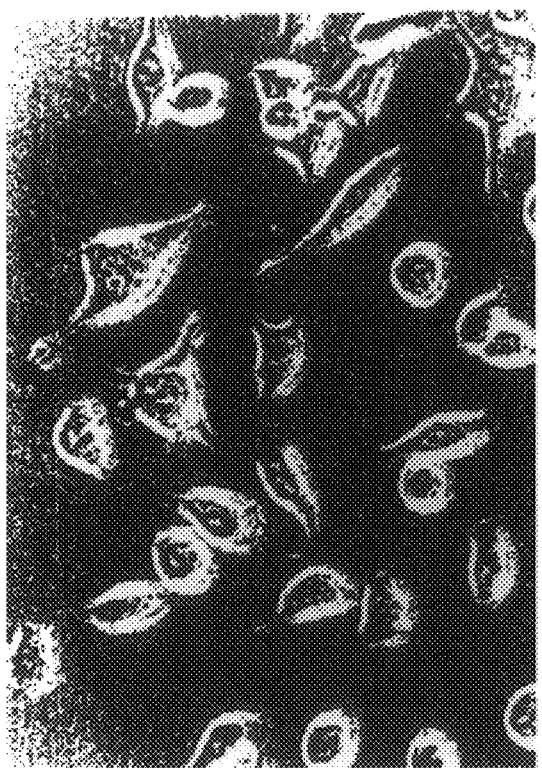
FIG. 6 is a reproduction of phase contrast micrographs showing the cytotoxic effect of the full-length p55IC in HTta1 cells transfected with an expression vector encoding this p55IC (right panel); and the inhibition of this cytotoxic effect when expression of the vector is blocked by treating the cells with tetracycline (left panel), as described in Example 2.
Figure 6B:
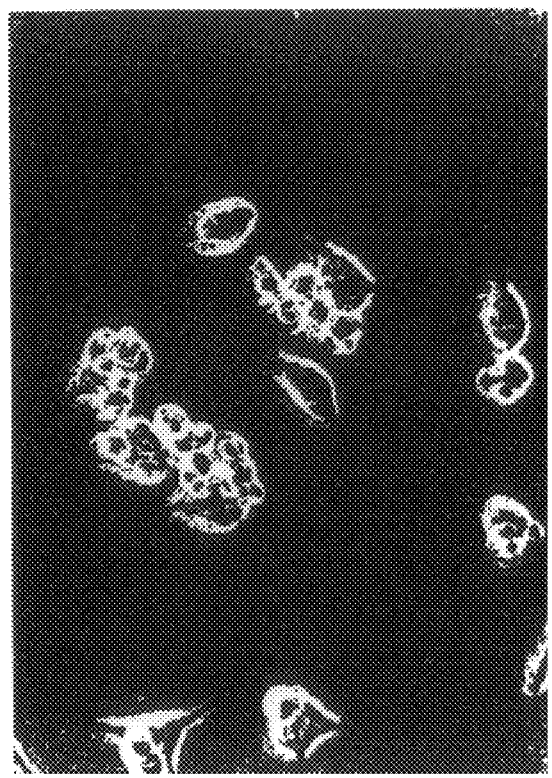

To evaluate the functional implications of the propensity of the p55-IC to self associate, we attempted to express the p55-IC within the cytoplasm of cells which are sensitive to the cytocidal effect of TNF. Considering the possibility that the p55-IC will turn to be cytotoxic, we chose to express it in an inducible manner, using the recently developed, tightly regulated tetracycline-controlled mammalian expression system (Gossen and Boujard, 1992). Expression of the p55-IC resulted in massive cell death (FIG. 6, right panel). The dying cells displayed cell surface blabbing as observed in the killing of the cells by TNF. Transfection of the p55-IC construct to the cells in the presence of tetracycline, which reportedly decreases the expression of pHD10-3 regulated constructs by as much as $10^5$ fold, still resulted in some cell death, although significantly less than that observed in the absence of tetracycline (FIG. 6, left panel). In contrast, cells transfected with a control construct, containing the luci-pherase cDNA, showed no signs of death (results not shown).

The ability of the p55-IC to trigger cell death, when expressed without the transmembrane or extracellular domains of the receptor, provides further evidence for the involvement of this domain in signaling. Furthermore, it indicates that no other part of the receptor plays a direct role in such signaling. Studies of the effects of mutations, including those mutations studied in the present invention, on the function of the p55-IC, indicated that the region extending between amino acid residues 326 and 407 is most critical for its function. This region shows marked resemblance to sequences within the intracellular domains of two other receptors, evolutionarily related to the p55 TNF-R—namely, the FAS receptor (Itoh et al., 1991; Oehm et al., 1992), which can also signal for cell death and CD40-a receptor (Stamenkovic et al., 1989) which enhances cell growth; this sequence therefore seems to constitute a conserved motif which plays some kind of general role in signaling. Since it does not resemble known motives characteristic of enzymatic activities, it seems plausible that it signals in indirect manner, i.e. possibly by serving as a docking site for signaling enzymes or for proteins which transmit stimulatory signals to them. The p55-IC, the FAS receptor and CD 40 can all be stimulated by antibodies against their extracellular domain. Their stimulation could be shown to correlate with the ability of the antibodies to cross-link the receptors. It therefore seems that the signaling is initiated as a consequence of interaction of two or more intracellular domains imposed by aggregation of the extracellular domains. Involvement of such interaction in the initiation of signaling of these receptors was also indicated by studies (Brakebusch et al., 1992) showing that expression of receptors made nonfunctional by mutation of their intracellular domain, had a "dominant negative" effect on the function of co-expressed normal receptors. Aggregation of the p55-R in response to TNF was suggested to occur in a passive manner, merely due to the fact that each of the TNF molecules, which occur as homotrimers, can bind two or three receptor molecules. However, the findings of the present invention suggest that this process occurs somewhat differently.

The propensity of the p55-IC to self associate indicates that this domain plays an active role in its induced aggregation. Moreover, this activity of the p55-IC seems to suffice for initiating its signaling, since when expressed independently of the rest of the receptor molecule, it can trigger cell death in the absence of TNF or any other exterior stimuli. Nevertheless, when expressed as the full length receptor, the p55-TNF-R does not signal, unless stimulated by TNF. One must, therefore, assume that when activating the p55-TNF-R, TNF actually overcomes some inhibitory mechanisms, which prevent spontaneous association of the intracellular domains, and this inhibition is due to the linkage of the p55-IC to the rest of the receptor molecule. The inhibition may be due to the orientation imposed on the intracellular domain by the transmembrane and extracellular domain, to association of some other proteins with the receptor or perhaps just due to restriction of the amounts of receptors that are allowed to be placed in the plasma membrane. Of note, this control mechanism should be rather effective, since according to some estimations, the binding of even just one TNF molecule to a cell suffices for the triggering of its death.

Spontaneous signaling, independent of ligand can result in extensive derangement of the process controlled by this receptor. The best known example is the deregulation of growth factor receptors. Mutations due to which they start signaling spontaneously, for example those that cause them to aggregate spontaneously, play an important role in the deregulated growth of tumor cells. TNF effects, when induced in excess, are well known to contribute to the pathology of many diseases. The ability of free intracellular domains (p55ICs) of the p55-TNF-R to signal independently of TNF may contribute to such excessive function. It seems possible, for example, that some of the cytopathic effects of viruses and other pathogens result, not from their direct cytocidal function, but from proteolytic detachment of the intracellular domain of the p55-TNF-R and the resulting TNF-like cytotoxic effect.

To further elucidate the region(s) within p55IC which is responsible for its self-association capability and hence its ligand-independent cell cytotoxicity, and also to determine whether other related members of the TNF/NGF receptor family (e.g. FAS-R) also have intracellular domains with self-association capabilities and ligand-independent effects, the following detailed study was performed:

(a) General Procedures and Materials (i) Two Hybrid Screen and Two-hybrid β-galactosidase Expression Test cDNA inserts, encoding the p55-IC and its deletion mutants, the FAS-IC and various other proteins (see FIG. 14), were cloned by PCR, either from the full-length cDNAs cloned previously in our laboratory, or from purchased cDNA libraries. β-galactosidase expression in yeasts (SFY526 reporter strain (Bartel et al., 1993)) transformed with these cDNAs in the pGBT-9 and pGAD-GH vectors (DNA binding domain (DBD) and activation domain (AD) constructs, respectively) was assessed by a liquid test (Guarente, 1983); it was also assessed by a filter assay, yielding qualitatively the same results (not shown). Two-hybrid screening (Fields and Song, 1989) of a purchased Gal4 AD-tagged HeLa cell cDNA library (Clontech, Palo Alto, Calif., U.S.A.) for proteins that bind to the intracellular domain of the p55-R (p55-IC), was performed using the HF7c yeast reporter strain according to the recommendation of the producer. Positivity of the isolated clones was assessed by (a) prototrophy of the transformed yeasts for histidine when grown in the presence of 5 mM 3-aminotriazole, (b) β-galactosidase expression (c) specificity tests (interaction with SNF4 and lamin fused to Gal4 DBD).

(ii) In vitro Self-association of Bacterially Produced p55-IC Fusion Proteins

Glutathione S-transferase (GST) and glutathione S-transferase-p55-IC fusion protein (GST-p55-IC) were produced as described elsewhere (Frangioni and Neel, 1993; Ausubel et al., 1994). Maltose binding protein (MBP) fusion proteins were obtained using the pMalcRI vector (New England Biolabs) and purified on an amylose resin column. The interaction of the MBPP and GST fusion proteins was investigated by incubating glutathione-agarose beads sequentially with the GST and MBPP fusion proteins (5 μg protein/20 1 beads; first incubation for 15 min, and the second for 2 h, both at 4° C.). Incubation with MBP fusion proteins was carried out in a buffer solution containing 20 mM Tris-HCl, pH 7.5, 100 mM KCl, 2 mM $CaCl_2$, 2 mM $MgCl_2$, 5 mM dithiothreitol, 0.2% Triton X100, 0.5 mM phenyl-methyl-sulphonyl-fluoride and 5% (v/v) glycerol or, when indicated, in that same buffer containing 0.4 M KCl, or 5 mM EDTA instead of $MgCl_2$. Association of the MBP fusion proteins was assessed by SDS polyacrylamide gel electrophoresis (10% acrylamide) of the proteins associated with the glutathione-agarose beads, followed by Western blotting. The blots were probed with rabbit antiserum against MBP (produced in our laboratory) and with horseradish-peroxidase-linked goat-anti-rabbit immunoglobulin.

(iii) Induced Expression in HeLa Cells of the P55-R and Fragments Thereof

HeLa cells expressing the tetracycline-controlled transactivator developed by Gossen and Bujard (the HtTA-1 clone (Gossen and Bujard, 1992)), were grown in Dulbecco's modified Eagle's medium, containing 10% fetal calf serum, 100 u/ml penicillin, 100 g/ml streptomycin and 0.5 mg/ml neomycin. cDNA inserts encoding the p55-R or parts thereof were introduced into a tetracycline-controlled expression vector (pUHD 10-3, kindly provided by H. Bujard). The cells were transfected with the expression construct (5 μg DNA/6 cm plate) by the calcium phosphate precipitation method (Ausubel et al., 1994). Effects of transient expression of the transfected proteins were assessed at the indicated times after transfection in the presence or absence of tetracycline (1 μg/ml). Clones of cells stably transfected with the human p55-IC cDNA in the pUHD 10-3 vector were established by transfecting the cDNA to HtTA-1 cells in the presence of tetracycline together with a plasmid conferring resistance to hygromycin, followed by selected for clones resistant hygromycin (200 μg/ml). Expression of the cDNA was obtained by removal of tetracycline which was otherwise maintained constantly in the cell growth medium.

(iv) Assessment of TNF-like Effects, Triggered by Induced Expression of the p55-R and Fragments Thereof Effects of induced expression of the receptor and of TNF on cell viability were assessed by the neutral-red uptake method (Wallach, 1984). Induction of IL-8 gene expression was assessed by Northern analysis. RNA was isolated using TRI REAGENT (Molecular Research Center, Inc.), denatured in formaldehyde/formamide buffer, electrophoresed through an agarose/formaldehyde gel and blotted to a Gene-Screen Plus membrane (Du Pont) in 10×SSPE buffer, using standard techniques. Filters were hybridized with an IL-8 cDNA probe (Matsushima et al., 1988), nucleotides 1–392), radiolabeled by the random-prime kit (Boehringer Mannheim Biochemica, Mannheim, Germany) and washed stringently according to the protocol of manufacturer. Autoradiography was performed for 1–2 days.

(v) Assessment of TNF Receptor Expression

TNF receptor expression in samples of $1\times10^6$ cells was assessed by measuring the binding of TNF, labeled with $^{125}I$ by the chloramine-T method, as previously described (Holtmann and Wallach, 1987). It was also assessed by ELISA, performed as described for the quantification of the soluble TNF receptors (Aderka et al., 1991), except for the use of RIPA buffer (10 mM Tris-HCl, pH 7.5, 150 mM NaCl, 1% NP-40, 1% deoxycholate, 0.1% SDS and 1 mM EDTA) to lyse the cells (70 $\mu l/10^6$ cells) and to dilute the tested samples. The soluble form of the p55-R, purified from urine, served as the standard.

(b) Mutational Analysis of the Intracellular Domain of the p55-R (p55-IC) to Determine the Regions of the p55-IC Involved in Its Self-association As noted above, p55-IC can self-associate and trigger cytotoxic effects on cells, and there are portions of the p55-IC, which themselves were capable of binding to the full-length p55-IC. In particular, one of the portions of the p55-IC (designated as protein fragment 55.1 in Example 1 above) was identified that was capable of binding strongly to the full length p55-IC, this portion was sequenced and was observed to contain the amino acid residues 328–426 of the p55-TNF-R, which are within the p55-IC. It has further been discovered (see below) that the above portion, protein fragment 55.1, is itself capable of self-association and of triggering cytotoxic effects on cells. Hence this portion of the p55-IC has been called the "death domain", and is located in the region between amino acid residues 328–426 of the human p55-R, most likely consisting of amino acid residues between about residue 328 and 414 thereof.

The fact that the "death domain" in the p55-IC self-associates was found by happenstance. On screening a HeLa cell cDNA library by the two-hybrid technique (see Example 1 above) for proteins that bind to the intracellular domain of this receptor, we detected among the cDNAs whose products bound specifically to the intracellular domain-GAL4 DBD fusion-protein, several clones (e.g. 55.1 and 55.3) that themselves encoded for parts of the p55-R intracellular domain (p55-IC; marked with asterisks in FIG. 14).

Applying the two-hybrid test to evaluate the extent of specificity in the self-association of p55-IC and to define more accurately the region involved led to the following findings (FIG. 14): (a) The self-association of p55-IC is confined to a region within the "death domain". Its N terminus is located between residues 328 and 344 and its C terminus, close to residue 404, somewhat upstream of the reported C terminus of this domain (residue 414). (b) Deletion of the membrane-proximal part of p55-IC upstream of the "death domain" enhanced self-association, suggesting that this region has an inhibitory effect on the association. (c) Mouse p55-IC self-associates, and also associates with the "death domain" of human p55-R. (d) Examination of the self-association of the intracellular domains of three other receptors of the TNF/NGF receptor family: FAS/APO1 (FAS-R), CD40 (Fields and Song, 1989) and the p75 TNF receptor (Smith et al., 1990), showed that FAS-IC, which signals for cell death by a sequence motif related to the p55-R "death domain", self-associates, and associates to some extent with the p55-IC. However, CD40-IC, that provides growth stimulatory signals (even though also containing a sequence resembling the "death domain"), and p75-IC, that bears no structural resemblance to p55-IC, do not self associate, nor do they bind p55-IC or FAS-IC.

FIG. 14 above shows the quantitative assessment of the interaction of Gal4 hybrid constructs encompassing the following proteins: the intracellular domain of human p55-R and its various deletion mutants (residues numbered as in (Loetscher et al., 1990)); the intracellular domains of mouse p55-R (residues 334–454, numbered as in (Goodwin et al., 1991)); mouse FAS/APO1 (FAS-IC, 166–306, numbered as in (Watanabe-Fukanaga et al., 1992)); human CD40 (CD40-IC, 216–277, numbered as in (Stamenkovic et al., 1989)); and human p75 TNF receptor (p75-IC, 287–461, numbered as in (Smith et al., 1990)). SNF1 and SNF4 were used as positive controls for association (Fields-and Song, 1989), and lamin as a negative control (Bartel et al., 1993). Proteins encoded by the Gal4 DBD constructs (pGBT9) are listed vertically; those encoded by the Gal4 AD constructs (pGAD-GH), horizontally. The two deletion mutants denoted by asterisks were cloned in a two-hybrid screen of a HeLa cell cDNA library (Clontech, Palo Alto, Calif., U.S.A.) using p55-IC cloned in pGBT9 as "bait". In that screen, four of about $4\times10^6$ cDNA clones examined were positive. Three of these clones were found to correspond to parts of human p55-R cDNA (two were identical, encoding residues 328–426 and one encoding residues 277–426). The fourth was found to encode an unknown protein. The β-galactosidase expression data are averages of assays of two independent transformants and are presented as amount of β-galactosidase product; (a unit of activity being defined as $OD_{420}$ times $10^3$ divided by $OD_{600}$ of the yeast culture and reaction time, in minutes). The detection limit of the assay was 0.05 units. Variation between duplicate samples was in all cases less that 25% of the average (not tested).

An in vitro test of the interaction of a p55-IC-glutathione-S-transferase (GST) bacterial fusion protein with a p55-IC-maltose binding protein (MBP) fusion protein confirmed that p55-R self-associates and ruled out involvement of yeast proteins in this association (see above). The association was not affected by increased salt concentration, or by EDTA (see above).

To evaluate the functional implications of the self-association of the death domain, we examined the way in which induced expression of p55-R, or of parts of it, affect cells sensitive to TNF cytotoxicity. The results of this analysis are set forth in FIG. 7 which depicts the ligand-independent triggering of a cytocidal effect in HeLa cells transfected with p55-R, its intracellular domain (p55-IC) or parts thereof (including the "death domain").

In FIG. 7 there is shown schematically, the various DNA molecules encoding the different types of TNF receptors included in the vectors with which the HeLa cells were transfected (extreme left hand side of FIG. 7); and the expression (left and middle bar graphs) and the viability (right bar graph) in HeLa cells expressing transiently the various full-length p55-R (p55-R), p55-IC or parts of p55-IC or, as a control, luciferase (LUC) (each being depicted at the extreme left side of FIG. 7), using a tetracycline-controlled expression vector. The open bar graphs (left, middle and right) represent cells transfected in the presence of tetracycline (1 µg/ml), which inhibits expression; and the filled bar graphs (left, middle and right) represent cells transfected in the absence of tetracycline. TNF receptor expression was assessed 20 h after transfection, both by ELISA, using antibodies against the receptor's extracellular domain (see schematic illustration on the left side of FIG. 7), and by determining the binding of radiolabeled TNF to the cells (middle). The cytocidal effect of the transfected proteins was assessed 48 h after transfection. Data shown are from one of three experiments with qualitatively similar results, in which each construct was tested in duplicate. ND—not determined.

Thus, from FIG. 7 it is apparent that by using an expression vector that permits strictly controlled expression of transfected cDNAs by a tetracycline regulated transactivator (Gossen and Bujard, 1992), a mere increase of p55-R expression in HeLa cells by expression of transiently transfected cDNA for the full-length receptor resulted in quite extensive cell death. An even greater cytotoxicity was observed when expressing just p55-IC. Significant cytotoxicity was also observed when expressing just a part of p55-IC comprising essentially the "death domain" (residues 328–426) in the HeLa cells. On the other hand, expression of parts of p55-IC that lacked the "death domain" or contained just part of it (or expression of the luciferase gene, used as an irrelevant control) had no effect on cell viability. The cytotoxicity of p55-IC was further confirmed using cells stably transformed with its cDNA; these cells continued to grow when p55-IC expression was not induced, but died when p55-IC was expressed (see above).

(c) Other Effects of the Intracellular Domain of the P55-TNF-R

To examine whether other activities of TNF are triggered by the self-association of the intracellular domain, including the "death domain" thereof, we examined the effect of increased expression of the full-length receptor (p55-R) and of the expression of the intracellular domain of the receptor (p55-IC), on the transcription of interleukin 8 (IL-8), known to be activated by TNF (Matsushima et al., 1988). The results are shown in FIG. 8, which depicts the ligand-independent induction of IL-8 gene expression in HeLa cells transfected with p55-R or p55-IC, using a tetracycline-controlled construct (see also "General Procedures and Materials" and Example 1 above). In panel A of FIG. 8 there is shown a reproduction of a Northern blot representing the Northern blot analysis (see "General Procedures and Materials" above) of RNA (7 g/lane) extracted from HeLa (HTta-1) cells, untreated ("control") or treated ("TNF") with TNF (500/ml for 4 h), or the HTta-1 cells 24 h after transfection (in the presence or absence of tetracycline) with p55-IC ("p55-IC"), the p55-R ("p55-R"), or luciferase ("Luc") cDNA. In panel B of FIG. 8 there is shown a reproduction of a Northern blot representing the methylene blue staining of 18S rRNA in each of the samples shown in panel A of FIG. 8.

Thus, as is apparent from FIG. 8, transfection of HeLa cells with a tetracycline-controlled construct encoding the p55-R cDNA induced IL-8 transcription. An-even stronger induction was observed in cells transfected with the cDNA for p55-IC. In both cases, the induction occurred only when tetracycline was excluded from the cell growth medium, indicating that it occurs as a consequence of expression of the transfected p55-R or p55-IC. Transfection with luciferase cDNA, as a control, had no effect on IL-8 transcription.

Accordingly, from the above results (FIG. 8), it appears that a mere increase in p55-R expression, or even expression of just the intracellular domain (p55-IC) thereof is sufficient to trigger, in a ligand (TNF)-independent fashion, cytotoxicity and other effects as well, including that of an increase in the expression of the IL-8 gene within cells. The triggering of these effects is most likely due to the self-association of the intracellular domain of the p55-R (p55-IC). As is set forth above, it appears that, upon self-association of the p55-IC, the "death domain" thereof is primarily responsible for signaling the induction of the intracellular processes leading to the triggering of cytotoxicity within the cells, whilst the other effects, e.g. the signaling leading to the induction of IL-8 gene expression, are likely due to other regions of the p55-IC as well, following the self-association thereof. It is therefore possible that different regions of the p55-IC are responsible for the different TNF-induced effects (e.g. cytotoxicity, IL-8 induction) within cells, these effects being a consequence of the intracellular signaling upon self-association of the p55-IC.

The fact that the p55-IC, can induce in a ligand (TNF)-independent fashion, the triggering of other intracellular effects e.g. IL-8 induction, means that the p55-IC or specific portions thereof may be used as a highly specific tool for bringing about such effects in cells or tissues that it is desired to treat, without the need for treating such cells or tissues with TNF. In many pathological conditions (e.g. malignancies), treatment with TNF, especially at high dosages can lead to undesirable side-effects due to the number of intracellular effects induced systemically by TNF following its binding to its receptors. By way of the discovery in accordance with the present invention that the p55-IC can mimic specific other TNF-induced effects (besides cytotoxicity), e.g. IL-8 induction, opens the way for introducing in a cell- or tissue-specific manner, p55-IC or specific portions thereof, which will be capable of signaling for the induction of specific desired intracellular effects, e.g. IL-8 induction, and thereby overcome the systemic side-effects often observed during TNF treatment.

(d) Ligand-independent Triggering of Cytocidal Effects in HeLa Cells by the Intracellular Domains and the "Death Domains" Thereof of p55 TNF-R and FAS-R (FAS/APO1)

As regards the cytotoxic activity of the intracellular domains of the p55 TNF-R and FAS-R (p55IC and FAS-IC) it has now also been further elucidated that both the p55IC, its "death domain" (p55DD) and the FAS-IC are capable of a ligand-independent triggering of a cytocidal effect in HeLa cells. In this study, HeLa cells were transfected with expression vectors containing various constructs of either the full-length p55-TNF-R, portions thereof including the p55IC and p55DD or the FAS-IC. In one set of experiments HeLa cells were co-transfected with constructs containing the p55 TNF-R (p55-R) and the FAS-IC (for details of the constructs, their preparation, etc. see above). The results of this study are depicted in FIG. 9 (A and B), wherein in both FIGS. 9A and B the constructs used for transfecting the HeLa cells are shown schematically in the left hand panels; the results of the TNF or FAS receptor expression are shown graphically in the two middle panels (second and third panels from the left); and the results of transfected cell viability are shown graphically in the right hand panels. In FIG. 9A there is shown the results of transfected HeLa cells transiently expressing the full-length p55-R, p55-IC or parts thereof, or as a control, luciferase (LUC), in all cases using a tetracycline-controlled expression vector. In FIG. 9B there is shown the results of transfected HeLa cells transiently expressing FAS-IC alone or together with the p55-R, using a tetracycline-controlled expression vector. In the graphic representation of the results in FIGS. 9A and B, the open bars represent cells transfected in the presence of tetracycline (1 µg/ml), which inhibits expression, and the closed bars represent cells transfected in the absence of tetracycline. TNF receptor expression was assessed 20 h after transfection, both by ELISA using antibodies against the extracellular domain of the receptor (see left hand panels), and by determining the binding of radiolabeled TNF to the cells (middle panels). The cytocidal effect of the transfected proteins was assessed 48 h after transfection. The data shown are from one of three experiments with qualitatively similar results in which each construct was tested in duplicate. The designation "ND" in FIGS. 9A and B means not determined. From the results shown in FIGS. 9A and B it is apparent that expression of only the p55IC results in even greater cytotoxicity. Significant cytotoxicity also occurs when expressing just the death domain (p55DD). In contrast, expression of parts of p55IC lacking the death domain or containing only part thereof, had no effect on cell viability. Expression of the FAS-IC did not result in significant cytotoxicity, yet it significantly enhanced the cytotoxicity of co-expressed p55-R.

EXAMPLE 3

Additional Proteins Capable of Binding to the Intracellular Domains of p55 TNF-R or FAS-R, OR P75 TNF-R Using the same approach and technology set forth in Example 1 above, many more proteins have been isolated and identified which are capable of binding to the p55IC, FAS-IC, or p75IC.

In FIGS. 10–12, the partial and preliminary nucleotide sequence of cDNA clones, designated F2, F9 and DD11, respectively, are shown schematically.

Clones F2 and F9 were isolated by screening a murine (mouse) embryonic library using the murine FAS-IC as "bait". In FIG. 10, there is shown schematically the partial nucleotide sequence from the F2 cDNA that has been sequenced. In FIG. 11, there is shown schematically the partial nucleotide sequence of 1724 bases from the F9 cDNA that has been sequenced. Analysis of the binding capability of the protein encoded by clones F2 and F9 (F2 and F9, respectively) has shown that:

(a) F2 interacts strongly with human p55IC and p55DD and with murine FAS-IC, while it interacts weakly with non-relevant (control) proteins SNF1 and Lamin as well as relevant protein, human FAS-IC.

(b) F9 interacts strongly with human p55-IC and murine FAS-IC, while it interacts weakly with human FAS-IC (relevant protein) and irrelevant proteins SNF1 and Lamin.

(c) Neither F2 nor F9 interacted at all with human p75IC, pGBT9 (empty bait vector), or human CD-40.

Further, from "Gene Bank" and "Protein Bank" searches it was revealed that F2 and F9 represent new proteins.

Thus, F2 and F9 represent new proteins having binding specificity for both FAS-IC and p55IC.

Clone DD11 was isolated by screening a human HeLa library using the human p55DD as "bait". In FIG. 12 there is shown schematically the partial nucleotide sequence of 425 bases from the DD11 cDNA that has been sequenced.

The DD11 clone has an approx. length of 800 nucleotides. The full length of the transcript is about 1.2 kb, the transcript having been probed using the clone. Analysis of the binding capability of the protein encoded by clone DD11 has shown that DD11 interacts strongly with the p55DD (a.a. 326–414) (see FIG. 9) and does not interact with deletion mutants of this domain, e.g., a.a. 326–404. DD11 also interacts with mouse and human FAS-IC and to some extent also with Lamin. DD11 does not interact at all with SNF1 or with pGBT9 (empty bait vector). DD11 is also not found in the "Gene Bank" and "Protein Bank" databases. Thus DD11 represents a p55 IC (p55DD) and FAS-IC specific binding protein.

Additional p55IC-binding clones were isolated by screening a human peripheral blood lymphocyte (PBL) library with human p55IC as "bait" in the same manner as described in Example 1 for screening a HeLa library using the yeast two-hybrid system. Of 270 cDNA clones analyzed from the PBL library, the four sets of clones, designated 4 (four individual clones having the same approximately 1 kb length insert), 65 (a single clone having an approximately 1.5 Kb length insert), 14v1 (two individual clones having the same approximately 1.5 Kb length insert), and 16v1 (six individual clones having the same approximately 1 Kb length insert), were identified. The results of analyzing which "baits" or portions of the p55IC "bait" can be bound by the four novel clones 4, 65, 14v1 and 16v1, as determined by blue color development, is shown in Table 2. Preliminary and partial nucleotide sequences for clones 4, 65, 14v1 and 16v1 are presented as SEQ ID NOs:33, 34, 35 and 36, respectively.

TABLE 2

Binding of Clones from a PBL Library to Various Baits

| BAIT | 14 vl | 16 vl | 65 | 4 |
|---|---|---|---|---|
| a.a. 226–326 p55 | | | | |
| a.a. 326–426 p55 | | slight blue in 5 h | | 2.5 h |
| a.a. 226–426 p55 | 1 h | <30 min. | <30 min. | <30 min. |
| a.a. 266–426 p55 | 2.5 h | | 2.5 h | |
| L351N p55 | | | | |
| hFAS IC | | | | |
| hFAS DD | | | | |
| CD40 | | | | |
| MORT1 | | | | |
| SNF | | | slight in 10 h | |
| p75 IC | | | | |
| LAMIN | | | | |
| CYC D | | | slight in 10 h | |
| GBT | | | | |
| TRADD | | | | |

Additional clones encoding for novel p75IC-associated proteins were obtained from HeLa cDNA library (Clontech) with pGAD-GH as the vector in the yeast two hybrid system described in Example 1, and using a fusion between lexA protein and the intracellular part of human p75 TNF-R as "bait". His+ clones were selected in yeast strain L40 and checked for LacZ (β-galactosidase activity). Plasmid DNA from His+LacZ+ clones were then extracted and tested for specificity to different "baits" in strain SFY526. Four clones that reacted specifically with p75IC, namely E3, E15, E19 and 230 were selected.

Table 3 presents a summary of the characteristics of the p75IC-binding proteins encoded by the clones E3, E15, E19 and 230. The cDNA insert size of clone E3 is approximately 0.5 Kb (SEQ ID NO:25). The E3 transcript may possibly be a product of alternate splicing as it has a sequence that is identical to part of a known gene, HHR23A (GenBank accession number D21235), reported in Masutani et al. (1994). Thus, E3 contains a nearly complete ubiquitin moiety (69 amino acid residues) of HHR23A within its amino acid sequence (SEQ ID NO:26) and specifically binds to p75IC, though not strongly. The E3 protein also does not coprecipitate with p75 in HeLa cells transfected with both E3 and p75 on a tetracycline-inducible vector pUHD10-3.

transcription is its enhancing effect on transcription of the HIV virus as mediated by NFkB. This enhancing effect is believed to play a critical role in the progression of AIDS. In this regard, drugs designed to interfere with the binding of proteins that enhance NFkB activity such as E15 and E19 on the basis of their structure will inhibit the progression of AIDS. Similarly, dominant negative mutants of the E15 and E19 protein would also help inhibit the progression of AIDS.

TABLE 3

Characteristics of Additional p75-R-Associated Proteins

| Clone | Insert (Kb) | ORF | Transcript (Kb) | Motifs | Homologous | Specificity | Binding Region in p75 | Coprecip. from HeLa |
|---|---|---|---|---|---|---|---|---|
| E3 | 0.5 | 126 | 1.7 | STPA rich | Ubiquitine Repair | Binds Lamin | 265–402 | no |
| E15 | 0.9–1.0 | 235 | 1.2 | HLH | PNPP | Specific | 265–402 346-439 (346–402) | + |
| E19 | 1.4 | 159 | 2.4–2.5 | | | Specific | 346–439 | ++ |
| 230 | 0.6–0.7 | 114 | | | | Specific | 346–439 | +++ |

The cDNA insert size of clone E15 is approximately 1 Kb (SEQ ID NO:27) with a mRNA transcript that appears to be approximately 1.2 Kb by Northern hybridization. "GenBank" and "Protein Bank" searches indicate that this is a novel gene which encodes a protein with a deduced amino acid sequence (SEQ ID NO:28) having homology with the proteins encoded by C. elegans gene Z49909 and the yeast gene G7587, with sites for CK-2 and PKC kinases and for myristoilation have similarity with the helix-turn-helix motif of the LysR family of bacterial proteins. The E15 protein coprecipitates with p75 in transfected HeLa cells.

The partial and preliminary nucleotide sequence (SEQ ID NO:29) obtained for the E19 clone reveals that its deduced amino acid sequence (SEQ ID NO:30) shares homology with the E15 clone as well as with the proteins encoded by C. elegans Z49909 gene and the yeast G7587 gene. Like the E15, E19 is a novel gene whose DNA and protein sequences were not found during searches of sequence databases and which encodes a protein that binds specifically to p75IC in yeast and coprecipitates with p75 in transfected HeLa cells.

The fourth additional clone identified as encoding a p75 IC-binding protein is clone 230, which has a cDNA insert of approximately 0.6–0.7 Kb, where the nucleotide sequence (SEQ ID NO:31) appears to encode a protein having 114 amino acid residues (SEQ ID NO:32). The protein encoded by the 230 clone specifically binds to p75 in yeast and coprecipitates well with p75 in transfected HeLa cells.

Table 4. presents the results of tests for binding of E3, E15, E19 and 230 to various baits. The results presented in Table 4 show that these proteins are very specific for p75IC and do not appear to significantly bind to the various other proteins tested. Proteins E15 and E19, found to have homology with a C. elegans and a yeast sequence, were also observed to be able to induce transcription factor NFKb when either the E15 or E19 gene was introduced into mammalian cells by transfection. It is believed that the region of p75IC located around residues 346–439 may be involved in regulation of the NFkB transcription factor and a transcription factor designated "Jun", and as such may well account for the effects of TNF on transcription regulation. Interference of the interaction between the E15 or E19 protein and p75-R is suspected to greatly interfere with the various proinflammatory effects of TNF. For instance, one of the best studied consequences of the effects of TNF on

TABLE 4

Binding of p75IC-Associated Proteins with Various Baits

| Binding | E15 | E19 | 230 | E3 |
|---|---|---|---|---|
| 75IC | + | + | + | + |
| 55IC | – | – | – | – |
| 326A | – | – | ND | – |
| 326S | – | – | ND | – |
| LAMIN | – | – | – | ± |
| SNF | – | – | – | – |
| CYCD | – | – | ND | – |
| CD40 | – | – | – | – |
| hFAS-IC | – | – | – | ± |
| coIP with p75 | + | ++ | +++ | – |

Note: ND = not done

EXAMPLE 4

Construction of Soluble Dimeric TNF Receptors

Based on the findings set forth in Example 2 above, that the intracellular domain of the p55-R (p55-IC) and a portion thereof (the "death domain"), and that the intracellular domain of the FAS/APO1 and a portion thereof (also called the "death domain") which resembles the p55-IC "death domain", are capable of self-association, it is possible to construct new TNF receptors which are capable of self-association (aggregation) and which are soluble. Such TNF receptors will be fusion proteins having essentially all of the extracellular domain of the p55-R fused to essentially all of the intracellular domains or "death domains" thereof of the p55-R or FAS/APO1. Thus, such fusion constructs will be devoid of the transmembranal domain of the p55-R (or FAS/APO1) and hence will be soluble. Moreover, by virtue of the self-association capability of the intracellular domains or "death domains" thereof, these fusion constructs will be capable of oligomerization to provide at least dimers (and possibly also higher order multimers) of the p55-R. Consequently, such dimeric TNF receptors (p55-R) will be capable of binding to at least two TNF monomers of the naturally-occurring TNF homotrimer to provide a soluble TNF receptor which binds more avidly to its ligand (homotrimeric TNF).

Accordingly, at least four types of p55 TNF receptor fusion proteins will be constructed each of which will be capable of oligomerization and will be soluble:
  (i) A fusion product between the extracellular domain of p55-R (EC55) and the intracellular domain of p55-R (p55-IC);
  (ii) A fusion product between the EC55 and the "death domain" of p55-IC (DD55);
  (iii) A fusion product between the EC55 and the intracellular domain of FAS/APO1 (ICFAS); and
  (iv) A fusion product between the EC55 and the "death domain" of ICFAS (DDFAS).

In each of the above fusion proteins the TNF monomer binding capability is provided by the EC55 portion while the oligomerization (or at least dimerization) of each kind of fusion protein is provided by its "tail" region being any of the p55IC, DD55, ICFAS or DDFAS portions.

For construction of the above fusion proteins, standard techniques of recombinant DNA technology will be employed that are now well established in the art (see for example Sambrook et al., (1989) Molecular Cloning: A Laboratory Manual, Cold Spring Harbor Laboratory Press, Cold Spring Harbor, N.Y.). Briefly, any suitable bacterial, bacteriophage, or animal virus expression vector (cloning vehicle or plasmid designed for expression of the inserted DNA of choice) may be employed into which will be inserted in one or more stages the DNA encoding the EC55 and one of the "tails" being the p55-IC, DD55, ICFAS or DDFAS. The so-inserted DNA encoding each of the fusion proteins will be placed under the control of the various expression control sequences of the cloning vehicle or plasmid such as promoters, ribozyme binding sites, transcriptional factor binding sites, etc. These expression control sequences will be chosen depending on the type of expression vector chosen and hence the type of host cell (eukaryotic or prokaryotic) in which it is desired to express the fusion proteins of the invention. Preferred host cells (and hence expression vectors) are eukaryotic, in particular, mammalian.

The DNA molecule encoding each of the above noted fusion proteins will be prepared and inserted into the expression vector by the following procedure:

(a) Firstly, a set of oligonucleotides for use in PCR will be constructed by standard means, the oligonucleotides being:
1) ACC ATG GGC CTC TCC ACC GTG (EC55, sense; SEQ ID NO:1)
2) ACGC GTC GAC TGT GGT GCC TGA GTC CTC (EC55, antisense; SEQ ID NO:2)
3) ACGC GTC GAC CGC TAC CAA CGG TGG AAG (IC55, sense; SEQ ID NO:3)
4) TCA TCT GAG AAG ACT GGG (IC55, antisense; SEQ ID NO:4)
5) ACGC GTC GAC AAG AGA AAG GAA GTA CAG (IC FAS, sense; SEQ ID NO:5)
6) CTA GAC CAA GCT TTG GAT (IC FAS, antisense; SEQ ID NO:6)
7) ACGC GTC GAC CCC GCG ACG CTG TAC GCC (DD55, sense; SEQ ID NO:7)
8) ACGC GTC GAC GAT GTT GAC TTG AGT AAA (DD FAS, sense; SEQ ID NO:8)

(b) Plasmids containing the cloned full-length p55-R and FAS/APO1 receptors which we have in our laboratory (see also co-pending EP568925 and Examples 1–3 above) will be subjected to the following manipulations to yield the DNA fragments encoding each of the fusion proteins, which DNA fragments are then ligated into the above noted expression vector of choice:

(i) To produce the DNA fragment coding for EC55 which is a component of all 4 fusion proteins, PCR is performed on a plasmid bearing cDNA of human p55 using the above oligonucleotide nos. 1 and 2 (size of fragment 640 bp).
  (ii) To get a fusion product EC55-IC55, PCR is performed on a plasmid bearing cDNA for human p55 using oligonucleotide nos. 3 and 4, to obtain a DNA fragment coding for IC55 (size 677 bp) which is then mixed with EC55 digested by Sal I and ligated by blunt end ligation into any expression vector for mammalian cells under the control of an appropriate promoter. The orientation of the inserted EC55-IC55 in the vector is verified by restriction digestion and by sequencing.
  (iii) To get a fusion product EC55-IC FAS, IC FAS is produced by PCR on a plasmid with cDNA for FAS using oligonucleotide nos. 5 and 6, to obtain a fragment (size 448 bp) which is then cut by Sal I and mixed with EC55 cut by SalI, and subsequently is blunt ligated into a mammalian expression vector under the control of an appropriate promoter. The orientation of the inserted EC55-IC FAS in the vector is verified by restriction digestion and by sequencing.
  (iv) To get a fusion product EC55-DD55, a DNA fragment is produced with the DD55 sequence by PCR in cDNA for human p55 using oligonucleotide nos. 7 and 4. The product with a size of 314 bp is cut by SalI and mixed with EC55 cut by SalI, and subsequently blunt ligated into the mammalian expression vector. Orientation of the inserted EC55-DD55 in the vector is verified by restriction digestion and by sequencing.
  (v) To get a fusion product EC55-DD FAS, a DNA fragment with DD FAS is produced by PCR on cDNA for FAS using oligonucleotide nos. 6 and 8. The product with a size of 332 bp is cut with SalI, and mixed with EC55 cut by Sal I and subsequently blunt ligated into the mammalian expression vector. Orientation of the EC55-DD FAS is then verified by restriction digestion and sequencing.

Once the above expression vectors have been constructed, they will then be introduced by standard methods into suitable mammalian cells (e.g. Chinese Hamster Ovary (CHO) or Monkey Kidney (COS) cells) for the purposes of expression. The so-expressed fusion proteins will then be purified by standard methods (see co-pending EP308378; EP398327; and EP568925). The purified fusion proteins will then be analyzed for their ability to oligomerize (and the extent thereof, i.e. whether they form dimers or higher order multimers) and for their ability to bind TNF (and the affinity or avidity of binding thereof).

EXAMPLE 5

Construction of Soluble Dimeric FAS/APO1 Receptors

In a similar fashion to that set forth in Example 4 above, it is possible to produce the following four kinds of FAS/APO1 fusion products, each of which will be capable of oligomerization and will be soluble:
  (i) Fusion product between the extracellular domain of FAS/APO1 (EC FAS) and the intracellular domain of p55-IC;
  (ii) Fusion product between the EC FAS and the "death domain" of p55-IC (DD55);
  (iii) Fusion product between the EC FAS and the intracellular domain of FAS/APO1 (IC FAS); and
  (iv) Fusion product between the EC FAS and the "death domain" of IC FAS (DD FAS).

In each of the above fusion proteins the FAS ligand binding capability is provided by the EC FAS portion, while the oligomerization (or at least dimerization) of each kind of fusion protein is provided by its "tail" region being any of the p55-IC, DD55, IC FAS or DD FAS portions.

The construction of the DNA fragments encoding the above fusion proteins and expression vectors containing them will be as detailed in Example 4, except different appropriate oligonucleotides (not shown) will be used for the preparation of the EC FAS fragment to be ligated to any of the above noted "tail" regions. Subsequently, the expression vectors will be introduced into the suitable host cells, and the resulting expressed fusion proteins will be purified and tested for their ability to oligomerize (and the extent thereof, i.e. whether they form dimers or higher order multimers) and for their ability to bind the FAS ligand (and the affinity or avidity of binding thereof).

EXAMPLE 6

Construction of Soluble Oligomeric "Mixed" TNF/ FAS Receptors

To prepare oligomeric receptors having "mixed" affinity, i.e. affinity for both TNF and the FAS-R ligand, the above-mentioned (Examples 4 and 5) fusion products may be utilized in the following procedure:

i) Providing a fusion product as set forth in Example 4, which contains the extracellular domain of a TNF-R (p75 TNF-R or p55 TNF-R) fused to any one of: the p55 IC, FAS-IC, p55 DD or FAS DD;

(ii) Providing a fusion product as set forth in Example 5, which contains the extracellular domain of FAS-R fused to any one of: p55 IC, FAS-IC, p55 DD or FAS-DD; and iii) mixing any one of the fusion products of i) with any one of the fusion products of ii) to provide a new dimeric (or higher order oligomeric) receptor which has both the extracellular domains of a TNF-R and FAS-R that are joined by their -IC or -DD regions.

In the above procedure the fusion products of i) and ii) may be provided separately, namely, from their purification from transformed cells in which they were produced, and then mixed in vitro to obtain the mixed affinity receptors. Alternatively, the host cells may be co-transfected with vectors carrying sequences encoding both types of fusion products, in which case, the mixed affinity receptors may be obtained directly from the co-transfected cells. The actual oligomerization of the fusion products into oligomeric receptors may take place within the cells or during or following the purification procedure to obtain the fusion products expressed in the cells. To specifically select for the mixed affinity receptors any standard method may be utilized, for example, affinity chromatography procedures in which antibodies against the TNF-R and FAS-R extracellular domains are used in sequential chromatographic steps to select for those receptors having both types of extracellular domain.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aderka, D., Englemann, H., Hornik, V., Skornick, Y., Levo, Y., Wallach, D. and Kushtai, G. (1991) Cancer Res. 51, 5602–5607.

Baens et al. (1993) Genomics 16:214–218.

Barinaga, M. (1993) Science 262:1512–4.

Bartel, P. L., Chien, C. T., Sternglanz, R. and Fields, S. (1993) Bio Techniques 14, 920–924.

Berger, J., Hauber, J., Hauber, R., Geiger, R. and Cullen, B. R. (1988) Gene 66, 1–10.

Beutler, B. and Cerami, C. (1987) NEJM, 316:379–385.

Boldin, M. P. et al. (1995) J. Biol. Chem. 270, 337–341.

Bollon, D. P. et al. (1980) J. Clin. Hematol. Oncol. 10, 39–48.

Botstein, D. et al. (1982) Miami Wint. SYMP. 19, 265–274.

Brakebusch, C. et al. (1992) EMBO J., 11:943–950.

Broach, J. R. (1981) in : *The Molecular Biology of the Yeast Saccharomyces: Life Cycle and Inheritance*. Cold Spring Harbor Laboratory, Cold Spring Harbor, N.Y. 445–470.

Broach, J. R. (1982) Cell 28, 203–204.

Brockhaus, M. et al. (1990) Proc. Natl. Acad. Sci. USA, 87:3127–3131.

Cantor, G. H. et al. (1993) Proc. Natl. Acad. Sci. USA 90:10932–6.

Chater, K. F. et al. (1986) in : *Sixth International Symposium on Actinomycetales Biology*, Akademiai Kaido, Budapest, Hungary, 45–54.

Chen, C. J. et al. (1992) Ann N. Y. Acad. Sci. 66b:271–3.

Cheng, J., Zhou, T., Liu, C. Shapiro, J. P. Brauer, M., Kiefer, M. C., Barr, P. J. and Mountz, J. D. (1994) Science 263, 1759–1762.

Crisell, P. et al., (1993) Nucleic Acids Res. (England) 21 (22):5251–5.
Crowe, P. D. et al., (1994) Science, 264:707–709.
Current protocols in molecular biology (Ausubel, F. M., Brent, R., Kingston, et al.), (1994) pp. 8.1.1–8.1.6 and 16.7–16.7.8, Greene Publishing Associates, Inc. and Wiley & Sons, Inc., New York.
DeMartino, G. N., et al. (1994) J. Biol. Chem. 269, 20878–20884.
Dirks, W., Wirth, M. and Hauser, H. (1993) Gene 128, 247–249.
Endo, H., et al. (1994) Clin. Exp. Immunol. 96, 31–35.
Engelmann, H. et al. (1990) J. Biol. Chem., 265:1531–1536.
Ferrick, M. R., et al. (1991) Invest. Ophthalmol. Vis. Sci. 32, 1534–1539.
Fields, S. and Song, O. (1989) Nature, 340:245–246.
Frangioni, J. V. and Neel, B. G. (1993) Anal. Biochem. 210, 179–187.
Glick, B. R. (1987) J. Ind. Microbiol. 1, 277–282.
Goodwin, R. G., et al. (1991) Mol. Cell Biol. 11, 3020–3026.
Gossen, M. and Boujard, H. (1992) Proc. Natl. Acad. Sci. USA, 89:5547–5551.
Gryczan, T. (1982) *The Molecular Biology of the Bacilli*, Academic Press, N.Y. 307–329.
Guarente, L. (1983) in Methods Enzymol. 101, 181–191.
Harada, A., Sekido, N., Kuno, A., Akiyama, M., Kasahara, T., Nakanishi, I., Mukaid, and Matsushima, K. (1993) Int. Immunol. 5, 681–690.
Heller, R. A. et al. (1990) Proc. Natl. Acad. Sci. USA, 87:6151–6155.
Hohmann, H.-P. et al. (1989) J. Biol. Chem., 264:14927–14934.
Holtmann, H. and Wallach, D. (1987) J. Immunol. 139, 1161–1167.
Itoh, N. et al. (1991) Cell 66:233.
Itoh, N. and Nagata, S. (1993) J. Biol. Chem. 268, 10932–7.
Izaki, K. (1978) Jpn. J. Bacteriol. 33, 729–742.
John, J. F. et al. (1986) Rev. Infect. Dis. 8, 693–704.
Joseph, S. and Burke, J. M. (1993) J. Biol. Chem. 268:24515–8.
Kendall, K. J. et al (1987) J. Bacteriol 169, 4177–4183.
Khan, A. S. et al. (1992) Nature Genetics, 2: 180–185.
Koizumi, M. et al. (1993) Biol. Pharm. Bull (Japan) 16 (9):879–83.
Kunkel, T. A. (1994) in: Current protocols in molecular biology, pp. 8.1.1–8.1.6 (Ausubel, F. M. et al., eds.) Greene Publishing Associates, Inc. and Wiley & Sons, Inc., New York.
Loetscher, H., Pan, Y-C. E., Lahm, H.-W, Gentz, R., Brockhaud, M., Tabuchi, H. and Lesslauer, W. (1990) Cell, 61:351–359.
Maniatis, T. et al. (1982) *Molecular Cloning: A Laboratory Manual*, Cold Spring Harbor Laboratory, Cold Spring Harbor.
Maniatis, T. (1980) in: *Cell Biology: A Comprehensive Treatise Vol. 3: Gene Expression*, Academic Press, N.Y. 563–608.
Matsutani, C. et al. (1994) EMBO J. 13:1831–1843.
Matsushima, K., et al. (1988) J. Exp. Med. 167:1883–1893.
Nophar, Y. et al. (1990) EMBO J., 9:3269–3278.
Oehm, A. et al. (1992) J. Biol. Chem. 267:10709.
Ogasawara, J., et al. (1993) Nature 364, 806–809.
Okayama, H. (1983) Mol. Cell Biol. 3, 280.
O'Neal, K. D. and Yu-Lee, L. Y. (1993) Lymphokine Cytokine Res. 12, 309–312.
Piquet, P. F. t al. (1987) J. Exp. Med., 166:1280–89.
Realini, C., Rogers, S. W. and Rechsteiner, M. (1994) FEBS Lett 348, 109–113.
Rechsteiner, M., et al. (1993) J. Biol. Chem. 268, 6065–6068.
Sambrook et al. (1989) *Molecular Cloning: A Laboratory Manual*, Cold Spring Harbor Laboratory Press, Cold spring Harbor, N.Y.
Schall, T. J. et al. (1990) Cell, 61:361–370.
Schwalb et al. (1993) J. Biol. Chem. 268 (14):9949–54.
Seger, R. and Krebs, E. G. (1995) FASEB J. 9:726–735.
Sekido, N., Mujaida, N., Harada, A., Nakanishi, I., Watanabe, Y., Matsushima, K. (1993) Nature 365, 654–657.
Shimayama, T. et al., (1993) Nucleic Acids Symp. Ser. 29:177–8
Shore, S. K. et al. (1993) Oncogene 8:3183–8.
Smith, C. A., David, T., Anderson, D., Solam, L., Beckmann, M. P., Jerzy, R., Dower, S. K., Cosman, D. and Goodwin, R. G. (1990) Science, 248:1019–1023.
Smith, D. B. and Corcoran, L. M. (1994) in: Current protocols in molecular biology, pp. 16.7.1–16.7.8 (Ausubel, F. M. et al., eds.) Greene Publishing Associates, Inc. and Wiley & Sons, Inc. New York.
Song, H. Y. et al. (1994) J. Biol. Chem. .269, 22492–22495.
Stamenkovic, I., Clark, E. A. and Seed, B. (1989) Embo J. 8:1403–1410.
Tartaglia, L. A., Ayres, T. M., Wong, G. H. and Goeddel, D. V. (1993) Cell, 74:845–853.
Tracey, J. T. et al. (1987) Nature, 330:662–664.
Wallach, D. (1984) J. Immunol. 132, 2464–9.
Wallach, D. (1986) in: Interferon 7 (Ion Gresser, ed.), pp. 83–122, Academic Press, London
Wallach, D. et al. (1994) Cytokine 6, 556.
Watanabe-Fukanaga, R., Brannan, C. I., Itoh, N., Yonehara, S., Copeland, N. G., Jenkins, N. A. and Nagata, S. (1992) J. Immunol. 148, 1274–1279.
Watanabe-Fukunaga, R. et al. (1992) Nature, 356, 314–317.
Wiegmann, K., Schutze, S., Machleidt, T., Witte, D. and Kronke, M. (1994) Cell 78, 1005–1015.
Wilks, A. F. et al. (1989) Proc. Natl. Acad. Sci. USA, 86:1603–1607.
Zhao, J. J. and Pick, L. (1993) Nature (England) 365:448–51.

What is claimed is:

1. An isolated DNA molecule encoding a polypeptide capable of binding to an intracellular domain of a p55 TNF receptor, comprising:
   (a) a DNA sequence encoding a polypeptide of residues 202–426 of SEQ ID NO:37; or
   (b) a DNA sequence encoding a fraction of a polypeptide encoded by the DNA of (a), which fraction maintains the capability of the polypeptide of which it is a fraction to bind to an intracellular domain of a p55 TNF-R, wherein the sequence of said DNA molecule encodes no more of SEQ ID NO:37 than is found in residues 202–426 of SEQ ID NO:37.

2. An isolated DNA molecule according to claim 1, encoding a protein selected from the group consisting of the herein designated proteins 55.1 and 55.3.

3. An isolated DNA molecule according to claim 2, encoding the protein 55.1 having the amino acid sequence corresponding to amino acid residue 328 to residue 426 of SEQ ID NO:37.

4. An isolated DNA molecule according to claim 2, encoding the protein 55.3 having the amino acid sequence corresponding to amino acid residue 277 to residue 426 of SEQ ID NO:37.

5. A vector comprising a DNA molecule according to claim 2.

6. Transformed eukaryotic or prokaryotic host cells containing a vector according to claim 5.

7. A method for producing a protein encoded by the DNA molecule of claim 2, said protein being capable of binding to an intracellular domain of a p55 TNF receptor, comprising growing host cells transformed with an expression vector comprising the DNA molecule of claim 5, under conditions suitable for the expression of said protein and extracting said protein from the culture medium of said transformed cells or from cell extracts of said transformed cells.

8. An isolated DNA molecule in accordance with claim 1, wherein said DNA sequence of (a) is that of a cDNA obtainable from a human cDNA library and including a sequence encoding the herein designated proteins 55.1 or 55.3.

9. A vector comprising a DNA molecule according to claim 8.

10. Transformed eukaryotic or prokaryotic host cells containing a vector according to claim 9.

11. A method for producing a protein encoded by the DNA molecule of claim 8, said protein being capable of binding to an intracellular domain of a p55 TNF receptor, comprising growing host cell transformed with an expression vector comprising the DNA molecule of claim 8, under conditions suitable for the expression of said protein, and extracting said protein form the culture medium of said transformed cells or from cell extracts of said transformed cells.

12. A vector comprising a DNA molecule according to claim 1.

13. Transformed eukaryotic or prokaryotic host cells containing a vector according to claim 12.

14. A method for producing a protein encoded by the DNA molecule of claim 1, said protein being capable of binding to an intracellular domain of a p55 TNF receptor, comprising growing host cells transformed with an expression vector comprising the DNA molecule of claim 1, under conditions suitable for the expression of said protein, and extracting said protein from the culture medium of said transformed cells or from cell extracts of said transformed cells.

* * * * *